(12) United States Patent
Gao et al.

(10) Patent No.: US 11,920,168 B2
(45) Date of Patent: *Mar. 5, 2024

(54) COMPOSITIONS AND METHODS FOR TRANSIENT DELIVERY OF NUCLEASES

(71) Applicant: University of Massachusetts, Boston, MA (US)

(72) Inventors: Guangping Gao, Worcester, MA (US); Phillip D. Zamore, Worcester, MA (US); Dan Wang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 618 days.

This patent is subject to a terminal disclaimer.

(21) Appl. No.: 16/775,311

(22) Filed: Jan. 29, 2020

(65) Prior Publication Data

US 2020/0231953 A1     Jul. 23, 2020

Related U.S. Application Data

(63) Continuation of application No. 15/550,452, filed as application No. PCT/US2016/017886 on Feb. 12, 2016, now Pat. No. 10,584,321.

(60) Provisional application No. 62/115,928, filed on Feb. 13, 2015.

(51) Int. Cl.
| | | |
|---|---|---|
| *C12N 9/22* | (2006.01) | |
| *A61K 38/00* | (2006.01) | |
| *A61K 48/00* | (2006.01) | |
| *C07K 14/005* | (2006.01) | |
| *C12N 7/00* | (2006.01) | |
| *C12N 15/11* | (2006.01) | |
| *C12N 15/90* | (2006.01) | |

(52) U.S. Cl.
CPC ............ *C12N 9/22* (2013.01); *A61K 48/005* (2013.01); *C07K 14/005* (2013.01); *C12N 7/00* (2013.01); *C12N 15/11* (2013.01); *C12N 15/907* (2013.01); *A61K 38/00* (2013.01); *C07K 2319/735* (2013.01); *C12N 2310/20* (2017.05); *C12N 2750/14121* (2013.01); *C12N 2750/14122* (2013.01); *C12N 2750/14142* (2013.01); *C12N 2750/14143* (2013.01)

(58) Field of Classification Search
CPC ...... C12N 2310/20; C12N 2750/14142; C12N 15/907; C12N 2750/14122; C12N 9/22; C12N 2750/14143; C12N 7/00; C12N 15/11; C12N 2750/14121; A61K 48/005; A61K 38/00; C07K 14/005; C07K 2319/735

See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,001,650 A | 12/1999 | Colosi |
| 6,156,303 A | 12/2000 | Russell et al. |
| 6,177,403 B1 | 1/2001 | Stedman |
| 6,251,677 B1 | 6/2001 | Wilson et al. |
| 6,399,575 B1 | 6/2002 | Smith et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,238,526 B2 | 7/2007 | Wilson et al. |
| 7,282,199 B2 | 10/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |

(Continued)

FOREIGN PATENT DOCUMENTS

| | | |
|---|---|---|
| EP | 2261242 A1 | 12/2010 |
| EP | 2453923 A2 | 5/2012 |

(Continued)

OTHER PUBLICATIONS

In vitro | definition of in vitro by Medical dictionary. https://medical-dictionary.com/in vitro, 2 (two) pages downloaded on Sep. 4, 2022. (Year: 2022).*

(Continued)

*Primary Examiner* — Ganapathirama Raghu
(74) *Attorney, Agent, or Firm* — Wolf, Greenfield & Sacks, P.C.

(57) ABSTRACT

The disclosure in some aspects relates to recombinant adeno-associated viruses having nuclease grafted to one or more capsid proteins. In some aspects, the disclosure relates to isolated AA V capsid proteins having terminally grafted nucleases and isolated nucleic acids encoding the same. Recent approaches to delivering nucleases to cells for gene editing have focused on delivering of expression vectors engineered to express the nucleases in target cells. However, these approaches have proved to be problematic in many instances due to genotoxicity resulting from to prolonged expression of gene editing system in vivo. To prevent such off-target genotoxicity due to prolonged presence of a gene editing system, several studies explored delivery of mRNA or protein instead of delivering the gene coding for the nucleases in cell culture.

11 Claims, 8 Drawing Sheets

Specification includes a Sequence Listing.

(56) References Cited

U.S. PATENT DOCUMENTS

| | | |
|---|---|---|
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 9,701,984 B2 | 7/2017 | Gao et al. |
| 10,370,432 B2 | 8/2019 | Esteves et al. |
| 10,584,321 B2 * | 3/2020 | Gao .................. C12N 7/00 |
| 2001/0016355 A1 | 8/2001 | Samulski et al. |
| 2002/0019050 A1 | 2/2002 | Gao et al. |
| 2002/0164783 A1 | 11/2002 | Feldhaus |
| 2002/0192823 A1 | 12/2002 | Bartlett |
| 2003/0040101 A1 | 2/2003 | Wilson et al. |
| 2003/0103939 A1 | 6/2003 | Engelhardt et al. |
| 2003/0110526 A1 | 6/2003 | Brown et al. |
| 2003/0119191 A1 | 6/2003 | Gao et al. |
| 2003/0138772 A1 | 7/2003 | Gao et al. |
| 2003/0207259 A1 | 11/2003 | Gao et al. |
| 2003/0228282 A1 | 12/2003 | Gao et al. |
| 2004/0101514 A1 | 5/2004 | Liu et al. |
| 2004/0219528 A1 | 11/2004 | Morris et al. |
| 2005/0014262 A1 | 1/2005 | Gao et al. |
| 2005/0032219 A1 | 2/2005 | Aubourg et al. |
| 2005/0037988 A1 | 2/2005 | Zamore et al. |
| 2005/0137153 A1 | 6/2005 | McSwiggen et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189515 A1 | 8/2006 | Beliveau et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0004042 A1 | 1/2007 | Gao et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2007/0292410 A1 | 12/2007 | Cashman et al. |
| 2008/0042783 A1 | 2/2008 | Makinen et al. |
| 2008/0075737 A1 | 3/2008 | Gao et al. |
| 2008/0075740 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0239240 A1 | 9/2009 | Chu |
| 2010/0104561 A1 | 4/2010 | Zhong et al. |
| 2010/0186103 A1 | 7/2010 | Gao et al. |
| 2010/0227909 A1 | 9/2010 | Cleary et al. |
| 2010/0323001 A1 | 12/2010 | Pachuk |
| 2011/0015256 A1 | 1/2011 | Sadek |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2011/0306550 A1 | 12/2011 | Vitek et al. |
| 2012/0041048 A1 | 2/2012 | Weinberg et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2013/0310443 A1 | 11/2013 | Srivastave et al. |
| 2013/0323226 A1 | 12/2013 | Wilson et al. |
| 2014/0010861 A1 | 1/2014 | Bancel et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0205599 A1 | 7/2014 | Willemsen et al. |
| 2014/0335054 A1 | 11/2014 | Gao et al. |
| 2014/0364338 A1 * | 12/2014 | Schaffer ............. A61K 38/1709 435/5 |
| 2015/0065560 A1 | 3/2015 | Bjorklund et al. |
| 2015/0258180 A1 | 9/2015 | Mahuran et al. |
| 2016/0000794 A1 | 1/2016 | Chiorini et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |
| 2018/0179501 A9 | 6/2018 | Gao et al. |
| 2018/0265863 A1 | 9/2018 | Esteves et al. |
| 2019/0038773 A1 | 2/2019 | Esteves et al. |

FOREIGN PATENT DOCUMENTS

| | | |
|---|---|---|
| EP | 2468891 A2 | 6/2012 |
| JP | 2008-538286 A | 10/2008 |
| WO | WO 2003/042397 A2 | 5/2003 |
| WO | WO 2003/093460 A1 | 11/2003 |
| WO | WO 2004/108922 A2 | 12/2004 |
| WO | WO 2005/033321 A2 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2007/127264 A2 | 11/2007 |
| WO | WO 2008/091703 A2 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/043936 A1 | 4/2009 |
| WO | WO 2009/109665 A1 | 9/2009 |
| WO | WO 2009/137006 A2 | 11/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/008823 A2 | 1/2011 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 A1 | 10/2015 |
| WO | WO 2015/168666 A2 | 11/2015 |
| WO | WO 2016/054554 A1 | 4/2016 |
| WO | WO 2016/065001 A1 | 4/2016 |
| WO | WO 2017/023724 A1 | 2/2017 |
| WO | WO 2017/136536 A1 | 8/2017 |
| WO | WO 2018/226785 A1 | 12/2018 |

OTHER PUBLICATIONS

Couzin et al., As Gelsinger case ends, Gene therapy suffers another blow. Science, 2005, vol. 307: 1028. (Year: 2005).*

(56) References Cited

OTHER PUBLICATIONS

Juengst ET., What next for human gene therapy? BMJ., 2003, vol. 326:1410-1411. (Year: 2003).*
Kimmelman J., Recent developments in gene transfer: risk and ethics. BMJ, 2005, vol. 350; 79-82. (Year: 2005).*
Raper SE., Gene therapy: The good, the bad, and the ugly. Surgery, 2005, vol. 137(5): 487-492. (Year: 2005).*
Rosenberg et al., Gene therapist, heal thyself. Science, 2000, vol. 287: 1751. (Year: 2000).*
Wolf JA., The "grand" problem of synthetic delivery. Nat. Biotechnol., 2002, vol. 20: 768-769. (Year: 2002).*
Touchette et al., Gene therapy: Not ready for prime time. Nat. Med., 1996, vol. 2(1 ): 7-8. (Year: 1996).*
International Search Report and Written Opinion dated Jun. 3, 2016, for Application No. PCT/US2016/017886.
International Preliminary Report on Patentability dated Aug. 24, 2017, for Application No. PCT/US2016/017886.
[No Author Listed], Definition of "nuclease" from Encyclopedia Britannica [online]. Retrieved on Jul. 7, 2019. https://www.britannica.com/science/nuclease. 1 page.
Adachi et al., Drawing a high-resolution functional map of adeno-associated virus capsid by massively parallel sequencing. Nat Commun. Jan. 17, 2014;5:3075. doi: 10.1038/ncomms4075.
Afione et al., In vivo model of adeno-associated virus vector persistence and rescue. J Virol. May 1996;70(5):3235-41.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.
Arbuthnot et al., Hepatic delivery of RNA interference activators for therapeutic application. Curr Gene Ther. Apr. 2009;9(2):91-103.
Asokan et al., The AAV vector toolkit: poised at the clinical crossroads. Mol Ther. Apr. 2012;20(4):699-708. doi: 10.1038/mt.2011.287. Epub Jan. 24, 2012.
Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.
Bals et al., Transduction of well-differentiated airway epithelium by recombinant adeno-associated virus is limited by vector entry. J Virol. Jul. 1999;73(7):6085-8.
Berns et al., Biology of adeno-associated virus. Curr Top Microbiol Immunol. 1996;218:1-23.
Berns et al., Detection of adeno-associated virus (AAV)-specific nucleotide sequences in DNA isolated from latently infected Detroit 6 cells. Virology. Dec. 1975;68(2):556-60.
Beutler et al., AAV for pain: steps towards clinical translation. Gene Ther. Apr. 2009;16(4): 461-9. Epub Mar. 5, 2009.
Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.
Borel et al., Recombinant AAV as a platform for translating the therapeutic potential of RNA interference. Mol Ther. Apr. 2014;22(4):692-701. doi:10.1038/mt.2013.285. Epub Dec. 19, 2013.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.
Buning et al., Receptor targeting of adeno-associated virus vectors. Gene Ther. Jul. 2003;10(14):1142-51.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Cloning and characterization of adeno-associated virus type 5. J Virol. Feb. 1999;73(2):1309-19.
Chirmule et al., Humoral immunity to adeno-associated virus type 2 vectors following administration to murine and nonhuman primate muscle. J Virol. Mar. 2000;74(5):2420-5.
Choi et al., Effects of adeno-associated virus DNA hairpin structure on recombination. J Virol. Jun. 2005;79(11):6801-7.
Choudhury et al., Identification of Novel vectors capable of CNS transduction in adult mice after single round selection using DNA shuffled AAV capsid library. Mol Ther. May 1, 2013;21(1):S1.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human α-1 Anti-Trypsin. Mol. Therapy. May 1, 2004;9:S333. Abstract 875.
Conrad et al., Safety of single-dose administration of an adeno-associated virus (AAV)-CFTR vector in the primate lung. Gene Ther. Aug. 1996;3(8):658-68.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.

(56) References Cited

OTHER PUBLICATIONS

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Ehlert et al., Cellular toxicity following application of adeno-associated viral vector-mediated RNA interference in the nervous system. BMC Neurosci. Feb. 18, 2010;11:20.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fischer et al., Successful transgene expression with serial doses of aerosolized rAAV2 vectors in rhesus macaques. Mol Ther. Dec. 2003;8(6):918-26.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.

Foust et al., Intravascular AAV9 preferentially targets neonatal-neurons and adult-astrocytes. Nature Biotechnology. Jan. 2009; 27(1): 59-65.

Foust et al., Over the barrier and through the blood: to CNS delivery we go. Cell Cycle. Dec. 15, 2009;8(24):4017-8.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Fu et al., Self-complementary adeno-associated virus serotype 2 vector: global distribution and broad dispersion of AAV-mediated transgene expression in mouse brain. Mol Ther. Dec. 2003;8(6):911-7.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gaj et al. ZFN, TALEN, and CRISPR/Cas-based methods for genome engineering. Trends Biotechnol. Jul. 1, 2013; 31(7): 397-405.

Gao et al., Adeno-associated viruses undergo substantial evolution in primates during natural infections. Proc Natl Acad Sci U S A. May 13, 2003;100(10):6081-6. Epub Apr. 25, 2003.

Gao et al., Adeno-associated virus-mediated gene transfer to nonhuman primate liver can elicit destructive transgene-specific T cell responses. Hum Gene Ther. Sep. 2009;20(9):930-42. doi: 10.1089/hum.2009.060.

Gao et al., Biology of AAV serotype vectors in liver-directed gene transfer to nonhuman primates. Mol Ther. Jan. 2006;13(1):77-87. Epub Oct. 10, 2005.

Gao et al., Clades of Adeno-associated viruses are widely disseminated in human tissues. J Virol. Jun. 2004;78(12):6381-8.

Gao et al., Erythropoietin gene therapy leads to autoimmune anemia in macaques. Blood. May 1, 2004;103(9):3300-2. Epub Dec. 24, 2003.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., New recombinant serotypes of AAV vectors. Curr Gene Ther. Jun. 2005;5(3):285-97.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., Purification of recombinant adeno-associated virus vectors by column chromatography and its performance in vivo. Hum Gene Ther. Oct. 10, 2000;11(15):2079-91.

Gao et al., RAAV-mediated targeting in adult mice and its potential in generating animal models of tissue-specific somatic transgenics or knock down. Molecular Therapy. May 2008;16(1):S118-S119. Abstract 316.

GENBANK Submission; Accession No. ADZ26851; Wilson et al.; Jun. 30, 2005.

GENBANK Submission; Accession No. AF028705.1; Rutledge et al.; Jan. 12, 1998.

GENBANK Submission; NCBI, Accession No. AAB95450; Rutledge et al.; Jan. 12, 1998.

GENBANK Submission; NCBI, Accession No. AAS99264; Gao et al.; Jun. 24, 2004.

GENBANK Submission; NCBI, Accession No. ABA71701; Schmidt et al.; May 10, 2006.

GENBANK Submission; NCBI, Accession No. ACB55301; Vandenberghe et al.; Jul. 31, 2008.

GENBANK Submission; NCBI, Accession No. ACB55310; Vandenberghe et al.; Jul. 31, 2008.

GENBANK Submission; NCBI, Accession No. AY530579.10; 2004.

GENBANK Submission; NCBI, Accession No. NP_049542; Xiao et al.; Mar. 11, 2010.

GENBANK Submission; NCBI, Accession No. YP_680426; Ruffing et al.; Nov. 19, 2010.

Grimm et al., Fatality in mice due to oversaturation of cellular microRNA/short hairpin RNA pathways. Nature. May 25, 2006;441(7092):537-41.

Grimm, Small silencing RNAs: state-of-the-art. Adv Drug Deliv Rev. Jul. 25, 2009;61(9):672-703. doi: 10.1016/j.addr.2009.05.002. Epub May 7, 2009.

Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.

Hernandez et al., Latent adeno-associated virus infection elicits humoral but not cell-mediated immune responses in a nonhuman primate model. J Virol. Oct. 1999;73(10):8549-58.

Hildinger et al., Hybrid vectors based on adeno-associated virus serotypes 2 and 5 for muscle-directed gene transfer. J Virol. Jul. 2001;75(13):6199-203.

Iida et al., Systemic Delivery of Tyrosine-Mutant AAV Vectors Results in Robust Transduction of Neurons in Adult Mice. BioMed Res Int. 2013;2013.

Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.

Jakobsson et al., Lentiviral vectors for use in the central nervous system. Mol Ther. Mar. 2006;13(3):484-93. Epub Jan. 3, 2006.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kotin et al., Organization of adeno-associated virus DNA in latently infected Detroit 6 cells. Virology. Jun. 1989; 170(2):460-7.

(56) References Cited

OTHER PUBLICATIONS

Kotin et al., Site-specific integration by adeno-associated virus. Proc Natl Acad Sci U S A. Mar. 1990;87(6):2211-5.

Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.

Lebherz et al., Gene therapy with novel adeno-associated virus vectors substantially diminishes atherosclerosis in a murine model of familial hypercholesterolemia. J Gene Med. Jun. 2004;6(6):663-72.

Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Li et al., Protein trans-splicing as a means for viral vector-mediated in vivo gene therapy. Hum Gene Ther. Sep. 2008;19(9):958-64. doi: 10.1089/hum.2008.009.

Lin et al., Impact of preexisting vector immunity on the efficacy of adeno-associated virus-based HIV-1 Gag vaccines. Hum Gene Ther. Jul. 2008;19(7):663-9.

Liu et al., Biological Differences in rAAV Transduction of Airway Epithelia in Humans and in Old World Non-human Primates. Mol Ther. Dec. 2007;15(12):2114-23. Epub Jul. 31, 2007.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Loiler et al., Targeting recombinant adeno-associated virus vectors to enhance gene transfer to pancreatic islets and liver. Gene Ther. Sep. 2003;10(18):1551-8.

Lowenstein, Crossing the rubicon. Nat Biotechnol. Jan. 2009;27(1):42-4.

Lux et al., Green fluorescent protein-tagged adeno-associated virus particles allow the study of cytosolic and nuclear trafficking. J Virol. Sep. 2005;79(18):11776-87.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Maguire et al., Directed evolution of adeno-associated virus for glioma cell transduction. J Neurooncol. Feb. 2010;96(3):337-47. doi:10.1007/s11060-009-9972-7. Epub Jul. 19, 2009.

Maguire et al., Gene therapy for the nervous system: challenges and new strategies. Neurotherapeutics. Oct. 2014;11(4):817-39. doi: 10.1007/s13311-014-0299-5.

Manfredsson et al., AAV9: a potential blood-brain barrier buster. Mol Ther. Mar. 2009;17(3):403-5.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Matalon et al., Adeno-associated virus-mediated aspartoacylase gene transfer to the brain of knockout mouse for canavan disease. Mol Ther. May 2003;7(5 Pt 1):580-7.

McCarty et al., Adeno-associated virus terminal repeat (TR) mutant generates self-complementary vectors to overcome the rate-limiting step to transduction in vivo. Gene Ther. Dec. 2003;10(26):2112-8.

McCarty et al., Integration of adeno-associated virus (AAV) and recombinant AAV vectors. Annu Rev Genet. Dec. 15, 2004;38:819-45.

McCarty et al., Self-complementary recombinant adeno-associated virus (scAAV) vectors promote efficient transduction independently of DNA synthesis. Gene Ther. Aug. 2001;8(16):1248-54.

McCarty, Self-complementary AAV vectors; advances and applications. Mol Ther. Oct. 2008;16(10):1648-56. Epub Aug. 5, 2008.

McCurdy et al., Sustained normalization of neurological disease after intracranial gene therapy in a feline model. Sci Transl Med. Apr. 9, 2014;6(231):231ra48. doi: 10.1126/scitranslmed.3007733.

Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.

Meister et al., Sequence-specific inhibition of microRNA- and siRNA-induced RNA silencing. RNA. Mar. 2004;10(3):544-50.

Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi: 10.1089/hum.2015.050. Epub Aug. 6, 2015.

Mingozzi et al., CD8(+) T-cell responses to adeno-associated virus capsid in humans. Nat Med. Apr. 2007;13(4):419-22. Epub Mar. 18, 2007.

Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.

Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

Mueller et al., In Vivo AAV Delivered Allele Specific shRNA for the Knockdown of Alpha-1 Antitrypsin. Molecular Therapy May 2010;18(1):S22. Abstract 53.

Mueller et al., In Vivo Allele Specific Knockdown of Mutant Alpha-1 Antitrypsin Using Recombinant AAV Delivered shRNA. Molecular Therapy May 2009;17(1):S313. Abstract 817.

Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.

Mueller et al., The pros and cons of immunomodulatory IL-10 gene therapy with recombinant AAV in a Cftr-/--dependent allergy mouse model. Gene Ther. Feb. 2009;16(2):172-83. Epub Sep. 25, 2008.

Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.

NCBI BLAST Protein Sequence. RID-09JSKF33114. Alignment of Seq ID Nos. 87, 179. 2016.

O'Reilly et al., RNA interference-mediated suppression and replacement of human rhodopsin in vivo. Am J Hum Genet. Jul. 2007;81(1):127-35. Epub May 23, 2007.

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.

Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.

Schaefer et al., Unexpected mutations after CRISPR-Cas9 editing in vivo. Nat Methods. May 30, 2017; 14(6): 547-8.

(56) References Cited

OTHER PUBLICATIONS

Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi: 10.4049/jimmunol.1501048.

Schnepp et al., Characterization of adeno-associated virus genomes isolated from human tissues. J Virol. Dec. 2005;79(23):14793-803.

Seiler et al., Adeno-associated virus types 5 and 6 use distinct receptors for cell entry. Hum Gene Ther. Jan. 2006;17(1):10-9.

Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.

Sondhi et al., Enhanced survival of the LINCL mouse following CLN2 gene transfer using the rh. 10 rhesus macaque-derived adeno-associated virus vector. Mol Ther. Mar. 2007;15(3):481-91. Epub Dec. 19, 2006.

Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.

Stoica et al., Targeting Human SOD1 Using AAV mediated RNAi in a mouse model of amyotrophic lateral sclerosis. Mol ther. Jun. 2013;21(1):S149.

Storek et al., Intrathecal long-term gene expression by self-complementary adeno-associated virus type 1 suitable for chronic pain studies in rats. Mol Pain. Jan. 30, 2006;2:4.

Storkebaum et al., Treatment of motoneuron degeneration by intracerebroventricular delivery of VEGF in a rat model of ALS. Nat Neurosci. Jan. 2005;8(1):85-92. Epub Nov. 28, 2004.

Suckau et al., 851. The Effect of Genome Size and Design of scAAV Vectors on Efficiency of shRNA Expression and Gene Knockdown. May 1, 2007;15(1):S325.

Tenenbaum et al., Recombinant AAV-mediated gene delivery to the central nervous system. J Gene Med. Feb. 2004;6 Suppl 1:S212-22.

Tomar et al., Use of adeno-associated viral vector for delivery of small interfering RNA. Oncogene. Aug. 28, 2003;22(36):5712-5.

Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

VandenBerghe et al., Heparin binding directs activation of T cells against adeno-associated virus serotype 2 capsid. Nat Med. Aug. 2006;12(8):967-71. Epub Jul. 16, 2006.

VandenBerghe et al., Tailoring the AAV vector capsid for gene therapy. Gene Ther. Mar. 2009;16(3):311-9. Epub Dec. 4, 2008.

VandenDriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

Virella-Lowell et al., Enhancing rAAV vector expression in the lung. J Gene Med. Jul. 2005;7(7):842-50.

Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.

Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The design of vectors for RNAi delivery system. Curr Pharm Des. May 1, 2008;14(13):1327-40.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Wu et al., Alpha2,3 and alpha2,6 N-linked sialic acids facilitate efficient binding and transduction by adeno-associated virus types 1 and 6. J Virol. Sep. 2006;80(18):9093-103.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Yan et al., Unique biologic properties of recombinant AAV1 transduction in polarized human airway epithelia. J Biol Chem. Oct. 6, 2006;281(40):29684-92. Epub Aug. 9, 2006.

Zabner et al., Adeno-associated virus type 5 (AAV5) but not AAV2 binds to the apical surfaces of airway epithelia and facilitates gene transfer. J Virol. Apr. 2000;74(8):3852-8.

Zhang et al., Characterization of 12 AAV vectors for intravascular delivery to target CNS and detarget non-CNS tissues by mirna regulation: implications in treatment of canavan disease. Molecular Therapy. May 2010;18(1):S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

(56) References Cited

OTHER PUBLICATIONS

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.
PCT/US2016/017886, Jun. 3, 2016, International Search Report and Written Opinion.
PCT/US2016/017886, Aug. 24, 2017, International Preliminary Report on Patentability.
Extended European Search Report for Application No. 16750031.3, dated Jun. 29, 2018.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

\* cited by examiner

SEQUENCE LISTING

<160> NUMBER OF SEQ ID NOS: 20

<210> SEQ ID NO 1
<211> LENGTH: 4197
<212> TYPE: DNA
<213> ORGANISM: Artificial Sequence
<220> FEATURE:
<223> OTHER INFORMATION: Synthetic Polynucleotide

<400> SEQUENCE: 1

```
atgtacccat acgatgttcc agattacgct tcgccgaaga aaaagcgcaa ggtcgaagcg      60
tccgacaaga agtacagcat cggcctggac atcggcacca actctgtggg ctgggccgtg     120
atcaccgacg agtacaaggt gcccagcaag aaattcaagg tgctgggcaa caccgaccgg     180
cacagcatca agaagaacct gatcggagcc ctgctgttcg acagcggcga aacagccgag     240
gccacccggc tgaagagaac cgccagaaga agatacacca gacggaagaa ccggatctgc     300
tatctgcaag agatcttcag caacgagatg gccaaggtgg acgacagctt cttccacaga     360
ctggaagagt ccttcctggt ggaagaggat aagaagcacg agcggcaccc catcttcggc     420
aacatcgtgg acgaggtggc ctaccacgag aagtacccca ccatctacca cctgagaaag     480
aaactggtgg acagcaccga caaggccgac ctgcggctga tctatctggc cctgcccac      540 atgatcaagt tccggggcca cttcctgatc gagggcgacc tgaaccccga caacagcgac     600
gtggacaagc tgttcatcca gctggtgcag acctacaacc agctgttcga ggaaaacccc     660
atcaacgcca gcggcgtgga cgccaaggcc atcctgtctg ccagactgag caagagcaga     720
cggctggaaa atctgatcgc ccagctgccc ggcgagaaga agaatggcct gttcggcaac     780
ctgattgccc tgagcctggg cctgaccccc aacttcaaga gcaacttcga cctggccgag     840
gatgccaaac tgcagctgag caaggacacc tacgacgacg acctggacaa cctgctggcc     900
cagatcggcg accagtacgc cgacctgttt ctggccgcca agaacctgtc cgacgccatc     960
ctgctgagcg acatcctgag agtgaacacc gagatcacca ggcccccct gagcgcctct    1020 atgatcaaga gatacgacga gcaccaccag gacctgaccc tgctgaaagc tctcgtgcgg    1080
cagcagctgc ctgagaagta caaagagatt ttcttcgacc agagcaagaa cggctacgcc    1140
ggctacattg acggcggagc cagccaggaa gagttctaca agttcatcaa gcccatcctg    1200
gaaaagatgg acggcaccga ggaactgctc gtgaagctga acagagagga cctgctgcgg    1260
aagcagcgga ccttcgacaa cggcagcatc ccccaccaga tccacctggg agagctgcac    1320
```

```
gccattctgc ggcggcagga agattttac ccattcctga aggacaaccg ggaaaagatc      1380
gagaagatcc tgaccttccg catccctac tacgtgggcc ctctggccag ggaaacagc       1440
agattcgcct ggatgaccag aaagagcgag gaaaccatca ccccctggaa cttcgaggaa     1500
gtggtgaca agggcgcttc cgcccagagc ttcatcgagc ggatgaccaa cttcgataag     1560
aacctgccca cgagaaggt gctgcccaag cacagcctgc tgtacgagta cttcaccgtg     1620
tataacgagc tgaccaaagt gaaatacgtg accgagggaa tgagaaagcc cgccttcctg    1680
agcggcgagc agaaaaaggc catcgtggac ctgctgttca agaccaaccg gaaagtgacc    1740
gtgaagcagc tgaaagagga ctacttcaag aaaatcgagt gcttcgactc cgtggaaatc    1800
tccggcgtgg aagatcggtt caacgcctcc ctgggcacat accacgatct gctgaaaatt    1860
atcaaggaca aggacttcct ggacaatgag gaaaacgagg acattctgga agatatcgtg    1920
ctgaccctga cactgtttga ggacagagag atgatcgagg aacggctgaa aacctatgcc    1980
cacctgttcg acgacaaagt gatgaagcag ctgaagcggc ggagatacac cggctggggc    2040
aggctgagcc ggaagctgat caacggcatc cgggacaagc agtccggcaa gacaatcctg    2100
gatttcctga gtccgacgg cttcgccaac agaaacttca tgcagctgat ccacgacgac    2160
agcctgacct ttaaagagga catccagaaa gcccaggtgt ccggccaggg cgatagcctg    2220
cacgagcaca ttgccaatct ggccggcagc cccgccatta agaagggcat cctgcagaca    2280
gtgaaggtgg tggacgagct cgtgaaagtg atgggccggc acaagcccga acatcgtg     2340
atcgaaatgg ccagagagaa ccagaccacc cagaagggac agaagaacag ccgcgagaga    2400
atgaagcgga tcgaagaggg catcaaagag ctgggcagcc agatcctgaa agaacacccc   2460
gtggaaaaca cccagctgca gaacgagaag ctgtacctgt actacctgca gaatgggcgg    2520
gatatgtacg tggaccagga actggacatc aaccggctgt ccgactacga tgtggaccat    2580
atcgtgcctc agagctttct gaaggacgac tccatcgaca caaggtgct gaccagaagc    2640
gacaagaacc ggggcaagag cgacaacgtg ccctccgaag aggtcgtgaa aagatgaag    2700
aactactggc ggcagctgct gaacgccaag ctgattaccc agagaaagtt cgacaatctg    2760
accaaggccg agagaggcgg cctgagcgaa ctggataagg ccggcttcat caagagacag    2820
ctggtggaaa cccggcagat cacaaagcac gtggcacaga tcctggactc ccggatgaac    2880
actaagtacg acgagaatga caagctgatc cgggaagtga agtgatcac cctgaagtcc    2940
aagctggtgt ccgatttccg gaaggatttc cagttttaca agtgcgcga tcaacaac      3000
taccaccacg cccacgacgc ctacctgaac gccgtcgtgg aaccgccct gatcaaaaag    3060
taccctaagc tggaaagcga gttcgtgtac ggcgactaca aggtgtacga cgtgcggaag    3120
atgatcgcca gagcgagca ggaaatcggc aaggctaccg ccaagtactt cttctacagc    3180
aacatcatga cttttcaa gaccgagatt accctggcca acggcgagat ccggaagcgg    3240
cctctgatcg agacaaacgg cgaaaccggg gagatcgtgt gggataaggg ccgggatttt   3300
gccaccgtgc ggaaagtgct gagcatgccc caagtgaata tcgtgaaaaa gaccgaggtg    3360
cagacaggcg gcttcagcaa agagtctatc ctgcccaaga ggaacagcga taagctgatc    3420
gccagaaaga aggactggga ccctaagaag tacgcggct cgacagccc caccgtggcc    3480
tattctgtgc tggtggtggc caaagtggaa aagggcaagt ccaagaaact gaagagtgtg    3540
aaagagctgc tggggatcac catcatggaa agaagcagct cgagaagaa tcccatcgac    3600
tttctggaag ccaagggcta caagaagtg aaaaaggacc tgatcatcaa gctgcctaag    3660
```

```
tactccctgt cgagctgga aaacggccgg aagagaatgc tggcctctgc cggcgaactg    3720
cagaagggaa acgaactggc cctgccctcc aaatatgtga acttcctgta cctggccagc    3780
cactatgaga agctgaaggg ctcccccgag gataatgagc agaaacagct gtttgtggaa    3840
cagcacaagc actacctgga cgagatcatc gagcagatca gcgagttctc caagagagtg    3900
atcctggccg acgctaatct ggacaaagtg ctgtccgcct acaacaagca ccgggataag    3960
cccatcagag agcaggccga gaatatcatc cacctgttta ccctgaccaa tctgggagcc    4020
cctgccgcct tcaagtactt tgacaccacc atcgaccgga gaggtacac cagcaccaaa    4080 gaggtgctgg acgccaccct gatccaccag agcatcaccg gcctgtacga gacacggatc    4140
gacctgtctc agctgggagg cgacagcccc aagaagaaga gaaaggtgga ggccagc        4197
```

<210> SEQ ID NO 2
<211> LENGTH: 1399
<212> TYPE: PRT
<213> ORGANISM: Artificial Sequence
<220> FEATURE:
<223> OTHER INFORMATION: Synthetic Polypeptide

<400> SEQUENCE: 2

```
Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Asp Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Tyr Thr Arg Arg Lys
                85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
        195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270
```

-continued

```
Lys Ser Asn Phe Asp Leu Ala Glu Asp Ala Lys Leu Gln Leu Ser Lys
            275                 280                 285

Asp Thr Tyr Asp Asp Leu Asp Asn Leu Leu Ala Gln Ile Gly Asp
290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
                340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
                420                 425                 430

Gln Ile His Leu Gly Glu Leu His Ala Ile Leu Arg Arg Gln Glu Asp
            435                 440                 445

Phe Tyr Pro Phe Leu Lys Asp Asn Arg Glu Lys Ile Glu Lys Ile Leu
            450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
                500                 505                 510

Glu Arg Met Thr Asn Phe Asp Lys Asn Leu Pro Asn Glu Lys Val Leu
            515                 520                 525

Pro Lys His Ser Leu Leu Tyr Glu Tyr Phe Thr Val Tyr Asn Glu Leu
530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
                580                 585                 590

Glu Cys Phe Asp Ser Val Glu Ile Ser Gly Val Glu Asp Arg Phe Asn
            595                 600                 605

Ala Ser Leu Gly Thr Tyr His Asp Leu Leu Lys Ile Ile Lys Asp Lys
            610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
                660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
```

```
                690                 695                 700
Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                725                 730                 735

Gly Asp Ser Leu His Glu His Ile Ala Asn Leu Ala Gly Ser Pro Ala
                740                 745                 750

Ile Lys Lys Gly Ile Leu Gln Thr Val Lys Val Val Asp Glu Leu Val
                755                 760                 765

Lys Val Met Gly Arg His Lys Pro Glu Asn Ile Val Ile Glu Met Ala
770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                805                 810                 815

Lys Glu His Pro Val Glu Asn Thr Gln Leu Gln Asn Glu Lys Leu Tyr
                820                 825                 830

Leu Tyr Tyr Leu Gln Asn Gly Arg Asp Met Tyr Val Asp Gln Glu Leu
                835                 840                 845

Asp Ile Asn Arg Leu Ser Asp Tyr Asp Val Asp His Ile Val Pro Gln
                850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                885                 890                 895

Lys Lys Met Lys Asn Tyr Trp Arg Gln Leu Leu Asn Ala Lys Leu Ile
                900                 905                 910

Thr Gln Arg Lys Phe Asp Asn Leu Thr Lys Ala Glu Arg Gly Gly Leu
                915                 920                 925

Ser Glu Leu Asp Lys Ala Gly Phe Ile Lys Arg Gln Leu Val Glu Thr
                930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
                965                 970                 975

Thr Leu Lys Ser Lys Leu Val Ser Asp Phe Arg Lys Asp Phe Gln Phe
                980                 985                 990

Tyr Lys Val Arg Glu Ile Asn Asn Tyr His His Ala His Asp Ala Tyr
                995                 1000                1005

Leu Asn Ala Val Val Gly Thr Ala Leu Ile Lys Lys Tyr Pro Lys
1010                1015                1020

Leu Glu Ser Glu Phe Val Tyr Gly Asp Tyr Lys Val Tyr Asp Val
1025                1030                1035

Arg Lys Met Ile Ala Lys Ser Glu Gln Glu Ile Gly Lys Ala Thr
1040                1045                1050

Ala Lys Tyr Phe Phe Tyr Ser Asn Ile Met Asn Phe Phe Lys Thr
1055                1060                1065

Glu Ile Thr Leu Ala Asn Gly Glu Ile Arg Lys Arg Pro Leu Ile
1070                1075                1080

Glu Thr Asn Gly Glu Thr Gly Glu Ile Val Trp Asp Lys Gly Arg
1085                1090                1095

Asp Phe Ala Thr Val Arg Lys Val Leu Ser Met Pro Gln Val Asn
1100                1105                1110
```

Ile Val Lys Lys Thr Glu Val Gln Thr Gly Gly Phe Ser Lys Glu
1115              1120              1125

Ser Ile Leu Pro Lys Arg Asn Ser Asp Lys Leu Ile Ala Arg Lys
1130              1135              1140

Lys Asp Trp Asp Pro Lys Lys Tyr Gly Gly Phe Asp Ser Pro Thr
1145              1150              1155

Val Ala Tyr Ser Val Leu Val Ala Lys Val Glu Lys Gly Lys
1160              1165              1170

Ser Lys Lys Leu Lys Ser Val Lys Glu Leu Leu Gly Ile Thr Ile
1175              1180              1185

Met Glu Arg Ser Ser Phe Glu Lys Asn Pro Ile Asp Phe Leu Glu
1190              1195              1200

Ala Lys Gly Tyr Lys Glu Val Lys Lys Asp Leu Ile Ile Lys Leu
1205              1210              1215

Pro Lys Tyr Ser Leu Phe Glu Leu Glu Asn Gly Arg Lys Arg Met
1220              1225              1230

Leu Ala Ser Ala Gly Glu Leu Gln Lys Gly Asn Glu Leu Ala Leu
1235              1240              1245

Pro Ser Lys Tyr Val Asn Phe Leu Tyr Leu Ala Ser His Tyr Glu
1250              1255              1260

Lys Leu Lys Gly Ser Pro Glu Asp Asn Glu Gln Lys Gln Leu Phe
1265              1270              1275

Val Glu Gln His Lys His Tyr Leu Asp Glu Ile Ile Glu Gln Ile
1280              1285              1290

Ser Glu Phe Ser Lys Arg Val Ile Leu Ala Asp Ala Asn Leu Asp
1295              1300              1305

Lys Val Leu Ser Ala Tyr Asn Lys His Arg Asp Lys Pro Ile Arg
1310              1315              1320

Glu Gln Ala Glu Asn Ile Ile His Leu Phe Thr Leu Thr Asn Leu
1325              1330              1335

Gly Ala Pro Ala Ala Phe Lys Tyr Phe Asp Thr Thr Ile Asp Arg
1340              1345              1350

Lys Arg Tyr Thr Ser Thr Lys Glu Val Leu Asp Ala Thr Leu Ile
1355              1360              1365

His Gln Ser Ile Thr Gly Leu Tyr Glu Thr Arg Ile Asp Leu Ser
1370              1375              1380

Gln Leu Gly Gly Asp Ser Pro Lys Lys Lys Arg Lys Val Glu Ala
1385              1390              1395

Ser

<210> SEQ ID NO 3
<211> LENGTH: 5997
<212> TYPE: DNA
<213> ORGANISM: Artificial Sequence
<220> FEATURE:
<223> OTHER INFORMATION: Synthetic Polynucleotide

<400> SEQUENCE: 3

```
atgtacccat acgatgttcc agattacgct tcgccgaaga aaaagcgcaa ggtcgaagcg    60
tccgacaaga agtacagcat cggcctggac atcggcacca actctgtggg ctgggccgtg   120
atcaccgacg agtacaaggt gcccagcaag aaattcaagg tgctgggcaa caccgaccgg   180
cacagcatca agaagaacct gatcggagcc ctgctgttcg acagcggcga aacagccgag   240
gccacccggc tgaagagaac cgccagaaga agatacacca gacggaagaa ccggatctgc   300
```

```
tatctgcaag agatcttcag caacgagatg gccaaggtgg acgacagctt cttccacaga      360
ctggaagagt ccttcctggt ggaagaggat aagaagcacg agcggcaccc catcttcggc      420
aacatcgtgg acgaggtggc ctaccacgag aagtacccca ccatctacca cctgagaaag      480
aaactggtgg acagcaccga caaggccgac ctgcggctga tctatctggc cctggcccac      540
atgatcaagt tccggggcca cttcctgatc gagggcgacc tgaaccccga caacagcgac      600
gtggacaagc tgttcatcca gctggtgcag acctacaacc agctgttcga ggaaaacccc      660
atcaacgcca gcggcgtgga cgccaaggcc atcctgtctg ccagactgag caagagcaga      720
cggctggaaa tctgatcgc ccagctgccc ggcgagaaga agaatggcct gttcggcaac      780
ctgattgccc tgagcctggg cctgaccccc aacttcaaga gcaacttcga cctggccgag      840
gatgccaaac tgcagctgag caaggacacc tacgacgacg acctggacaa cctgctggcc      900
cagatcggcg accagtacgc cgacctgttt ctggccgcca agaacctgtc cgacgccatc      960
ctgctgagcg acatcctgag agtgaacacc gagatcacca aggcccccct gagcgcctct     1020
atgatcaaga gatacgacga gcaccaccag gacctgaccc tgctgaaagc tctcgtgcgg     1080
cagcagctgc ctgagaagta caaagagatt ttcttcgacc agagcaagaa cggctacgcc     1140
ggctacattg acggcggagc cagccaggaa gagttctaca gttcatcaa gcccatcctg     1200 gaaaagatgg acggcaccga ggaactgctc gtgaagctga acagagagga cctgctgcgg     1260
aagcagcgga ccttcgacaa cggcagcatc ccccaccaga tccacctggg agagctgcac     1320
gccattctgc ggcggcagga agattttttac ccattcctga aggacaaccg ggaaaagatc     1380
gagaagatcc tgaccttccg catcccctac tacgtgggcc ctctggccag ggaaacagc      1440 agattcgcct ggatgaccag aaaagagcgag gaaaccatca cccctggaa cttcgaggaa     1500 gtggtggaca agggcgcttc cgcccagagc ttcatcgagc ggatgaccaa cttcgataag     1560
aacctgccca cgagaaggt gctgcccaag cacagcctgc tgtacgagta cttcaccgtg     1620
tataacgagc tgaccaaagt gaaatacgtg accgagggaa tgagaaagcc cgccttcctg     1680
agcggcgagc agaaaaaggc catcgtggac ctgctgttca agaccaaccg gaaagtgacc     1740
gtgaagcagc tgaaagagga ctacttcaag aaaatcgagt gcttcgactc cgtggaaatc     1800
tccggcgtgg aagatcggtt caacgcctcc ctgggcacat accacgatct gctgaaaatt     1860
atcaaggaca aggacttcct ggacaatgag gaaaacgagg acattctgga agatatcgtg     1920 ctgacccctga cactgtttga ggacagagag atgatcgagg aacggctgaa aacctatgcc     1980
cacctgttcg acgacaaagt gatgaagcag ctgaagcggc ggagatacac cggctggggc     2040
aggctgagcc ggaagctgat caacggcatc cgggacaagc agtccggcaa gacaatcctg     2100
gatttcctga agtccgacgg cttcgccaac agaaacttca tgcagctgat ccacgacgac     2160
agcctgacct ttaaagagga catccagaaa gcccaggtgt ccggccaggg cgatagcctg     2220
cacgagcaca ttgccaatct ggccggcagc cccgccatta agaagggcat cctgcagaca     2280
gtgaaggtgg tggacgagct cgtgaaagtg atggggccggc acaagcccga acatcgtg      2340 atcgaaatgg ccagagagaa ccagaccacc cagaagggac agaagaacag ccgcgagaga     2400
atgaagcgga tcgaagaggg catcaaagag ctgggcagcc agatcctgaa agaacacccc     2460
gtggaaaaca cccagctgca gaacgagaag ctgtacctgt actacctgca gaatgggcgg     2520
gatatgtacg tggaccagga actggacatc aaccggctgt ccgactacga tgtggaccat     2580
atcgtgcctc agagctttct gaaggacgac tccatcgaca caaggtgct gaccagaagc     2640
```

```
gacaagaacc ggggcaagag cgacaacgtg ccctccgaag aggtcgtgaa gaagatgaag    2700
aactactggc ggcagctgct gaacgccaag ctgattaccc agagaaagtt cgacaatctg    2760
accaaggccg agagaggcgg cctgagcgaa ctggataagg ccggcttcat caagagacag    2820
ctggtggaaa cccggcagat cacaaagcac gtggcacaga tcctggactc ccggatgaac    2880
actaagtacg acgagaatga caagctgatc cgggaagtga agtgatcac cctgaagtcc     2940 aagctggtgt ccgatttccg gaaggatttc cagttttaca agtgcgcga gatcaacaac     3000 taccaccacg cccacgacgc ctacctgaac gccgtcgtgg aaccgccct gatcaaaaag     3060 taccctaagc tggaaagcga gttcgtgtac ggcgactaca aggtgtacga cgtgcggaag    3120
atgatcgcca agagcgagca ggaaatcggc aaggctaccg ccaagtactt cttctacagc    3180
aacatcatga cttttttcaa gaccgagatt accctggcca acggcgagat ccggaagcgg    3240
cctctgatcg agacaaacgg cgaaaccggg agatcgtgt gggataaggg ccgggatttt    3300
gccaccgtgc ggaaagtgct gagcatgccc caagtgaata tcgtgaaaaa gaccgaggtg    3360
cagacaggcg gcttcagcaa agagtctatc ctgcccaaga ggaacagcga taagctgatc    3420
gccagaaaga aggactggga ccctaagaag tacggcggct cgacagccc accgtggcc     3480 tattctgtgc tggtggtggc caaagtgaaa agggcaagt ccaagaaact gaagagtgtg     3540
aaagagctgc tggggatcac catcatggaa agaagcagct cgagaagaa tcccatcgac     3600 tttctggaag ccaagggcta caagaagtg aaaaaggacc tgatcatcaa gctgcctaag     3660
tactccctgt tcgagctgga aaacggccgg aagagaatgc tggcctctgc cggcgaactg    3720
cagaagggaa cgaactggc cctgccctcc aaatatgtga acttcctgta cctggccagc    3780
cactatgaga agctgaaggg ctcccccgag gataatgagc agaaacagct gtttgtggaa    3840
cagcacaagc actacctgga cgagatcatc gagcagatca gcgagttctc caagagagtg    3900
atcctggccg acgctaatct ggacaaagtg ctgtccgcct acaacaagca ccgggataag    3960
cccatcagag agcaggccga gaatatcatc cacctgttta ccctgaccaa tctgggagcc    4020
cctgccgcct tcaagtactt tgacaccacc atcgaccgga gaggtacac cagcaccaaa    4080 gaggtgctgg acgccaccct gatccaccag agcatcaccg gcctgtacga gacacggatc    4140
gacctgtctc agctgggagg cgacagcccc aagaagaaga aaggtgga ggccagcgaa     4200 ttggctccgg gaaaaagag gccggtagag cactctcctg tggagccaga ctcctcctcg    4260
ggaaccggaa aggcgggcca gcagcctgca agaaaaagat tgaattttgg tcagactgga    4320
gacgcagact cagtacctga ccccagcct ctcggacagc caccagcagc ccctctggt     4380 ctgggaacta atacgatggc tacaggcagt ggcgcaccaa tggcagacaa taacgagggc    4440
gccgacggag tgggtaattc ctcgggaaat tggcattgcg attccacatg gatgggcgac    4500
agagtcatca ccaccagcac ccgaacctgg gccctgccca cctacaacaa ccacctctac    4560
aaacaaattt ccagccaatc aggagcctcg aacgacaatc actactttgg ctacagcacc    4620
ccttgggggt attttgactt caacagattc cactgccact tttcaccacg tgactggcaa    4680
agactcatca caacaactg gggattccga cccaagagac tcaacttcaa gctctttaac    4740
attcaagtca aagaggtcac gcagaatgac ggtacgacga cgattgccaa taaccttacc    4800
agcacggttc aggtgtttac tgactcggag taccagctcc cgtacgtcct cggctcggcg    4860
catcaaggat gcctcccgcc gttcccagca gacgtcttca tggtgccaca gtatggatac    4920 ctcacccctga caacgggag tcaggcagta ggacgctctt cattttactg cctgagtac     4980 tttccttctc agatgctgcg taccggaaac aactttacct tcagctacac ttttgaggac    5040
```

-continued

```
gttcctttcc acagcagcta cgctcacagc cagagtctgg accgtctcat gaatcctctc    5100
atcgaccagt acctgtatta cttgagcaga acaaacactc caagtggaac caccacgcag    5160
tcaaggcttc agttttctca ggccggagcg agtgacattc gggaccagtc taggaactgg    5220
cttcctggac cctgttaccg ccagcagcga gtatcaaaga catctgcgga taacaacaac    5280
agtgaatact cgtggactgg agctaccaag taccacctca atggcagaga ctctctggtg    5340
aatccgggcc cggccatggc aagccacaag gacgatgaag aaaagttttt tcctcagagc    5400
ggggttctca tctttgggaa gcaaggctca gagaaaacaa atgtggacat tgaaaaggtc    5460
atgattacag acgaagagga aatcaggaca accaatcccg tggctacgga gcagtatggt    5520
tctgtatcta ccaacctcca gagaggcaac agacaagcag ctaccgcaga tgtcaacaca    5580
caaggcgttc ttccaggcat ggtctggcag acagagatg tgtaccttca ggggcccatc    5640
tgggcaaaga ttccacacac ggacggacat tttcacccct ctcccctcat gggtggattc    5700
ggacttaaac accctcctcc acagattctc atcaagaaca cccgtacc tgcgaatcct    5760
tcgaccacct tcagtgcggc aaagtttgct tccttcatca cacagtactc cacgggacag    5820
gtcagcgtgg agatcgagtg ggagctgcag aaggaaaaca gcaaacgctg gaatcccgaa    5880
attcagtaca cttccaacta caacaagtct gttaatgtgg actttactgt ggacactaat    5940
ggcgtgtatt cagagcctcg ccccattggc accagatacc tgactcgtaa tctgtaa    5997
```

<210> SEQ ID NO 4
<211> LENGTH: 1998
<212> TYPE: PRT
<213> ORGANISM: Artificial Sequence
<220> FEATURE:
<223> OTHER INFORMATION: Synthetic Polypeptide

<400> SEQUENCE: 4

```
Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Asp Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Tyr Thr Arg Arg Lys
                85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190
```

```
Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
        275                 280                 285

Asp Thr Tyr Asp Asp Leu Asp Asn Leu Leu Ala Gln Ile Gly Asp
290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
        355                 360                 365

Glu Ile Phe Phe Asp Gln Ser Lys Asn Gly Tyr Ala Gly Tyr Ile Asp
370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
        435                 440                 445

Phe Tyr Pro Phe Leu Lys Asp Asn Arg Glu Lys Ile Glu Lys Ile Leu
450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
        515                 520                 525

Pro Lys His Ser Leu Leu Tyr Glu Tyr Phe Thr Val Tyr Asn Glu Leu
530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
        595                 600                 605

Ala Ser Leu Gly Thr Tyr His Asp Leu Leu Lys Ile Ile Lys Asp Lys
```

```
            610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                    645                 650                 655

Lys Thr Tyr Ala His Leu Phe Asp Asp Lys Val Met Lys Gln Leu Lys
                660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
        690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                    725                 730                 735

Gly Asp Ser Leu His Glu His Ile Ala Asn Leu Ala Gly Ser Pro Ala
                740                 745                 750

Ile Lys Lys Gly Ile Leu Gln Thr Val Lys Val Val Asp Glu Leu Val
            755                 760                 765

Lys Val Met Gly Arg His Lys Pro Glu Asn Ile Val Ile Glu Met Ala
770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                    805                 810                 815

Lys Glu His Pro Val Glu Asn Thr Gln Leu Gln Asn Glu Lys Leu Tyr
                820                 825                 830

Leu Tyr Tyr Leu Gln Asn Gly Arg Asp Met Tyr Val Asp Gln Glu Leu
            835                 840                 845

Asp Ile Asn Arg Leu Ser Asp Tyr Asp Val Asp His Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                    885                 890                 895

Lys Lys Met Lys Asn Tyr Trp Arg Gln Leu Leu Asn Ala Lys Leu Ile
                900                 905                 910

Thr Gln Arg Lys Phe Asp Asn Leu Thr Lys Ala Glu Arg Gly Gly Leu
            915                 920                 925

Ser Glu Leu Asp Lys Ala Gly Phe Ile Lys Arg Gln Leu Val Glu Thr
        930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
                    965                 970                 975

Thr Leu Lys Ser Lys Leu Val Ser Asp Phe Arg Lys Asp Phe Gln Phe
                980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
        1010                1015                1020

Leu Glu Ser Glu Phe Val Tyr Gly Asp Tyr Lys Val Tyr Asp Val
        1025                1030                1035
```

```
Arg Lys Met Ile Ala Lys Ser Glu Gln Glu Ile Gly Lys Ala Thr
    1040            1045                1050
Ala Lys Tyr Phe Phe Tyr Ser Asn Ile Met Asn Phe Phe Lys Thr
    1055            1060                1065
Glu Ile Thr Leu Ala Asn Gly Glu Ile Arg Lys Arg Pro Leu Ile
    1070            1075                1080
Glu Thr Asn Gly Glu Thr Gly Glu Ile Val Trp Asp Lys Gly Arg
    1085            1090                1095
Asp Phe Ala Thr Val Arg Lys Val Leu Ser Met Pro Gln Val Asn
    1100            1105                1110
Ile Val Lys Lys Thr Glu Val Gln Thr Gly Gly Phe Ser Lys Glu
    1115            1120                1125
Ser Ile Leu Pro Lys Arg Asn Ser Asp Lys Leu Ile Ala Arg Lys
    1130            1135                1140
Lys Asp Trp Asp Pro Lys Lys Tyr Gly Gly Phe Asp Ser Pro Thr
    1145            1150                1155
Val Ala Tyr Ser Val Leu Val Ala Lys Val Glu Lys Gly Lys
    1160            1165                1170
Ser Lys Lys Leu Lys Ser Val Lys Glu Leu Leu Gly Ile Thr Ile
    1175            1180                1185
Met Glu Arg Ser Ser Phe Glu Lys Asn Pro Ile Asp Phe Leu Glu
    1190            1195                1200
Ala Lys Gly Tyr Lys Glu Val Lys Lys Asp Leu Ile Ile Lys Leu
    1205            1210                1215
Pro Lys Tyr Ser Leu Phe Glu Leu Glu Asn Gly Arg Lys Arg Met
    1220            1225                1230
Leu Ala Ser Ala Gly Glu Leu Gln Lys Gly Asn Glu Leu Ala Leu
    1235            1240                1245
Pro Ser Lys Tyr Val Asn Phe Leu Tyr Leu Ala Ser His Tyr Glu
    1250            1255                1260
Lys Leu Lys Gly Ser Pro Glu Asp Asn Glu Gln Lys Gln Leu Phe
    1265            1270                1275
Val Glu Gln His Lys His Tyr Leu Asp Glu Ile Ile Glu Gln Ile
    1280            1285                1290
Ser Glu Phe Ser Lys Arg Val Ile Leu Ala Asp Ala Asn Leu Asp
    1295            1300                1305
Lys Val Leu Ser Ala Tyr Asn Lys His Arg Asp Lys Pro Ile Arg
    1310            1315                1320
Glu Gln Ala Glu Asn Ile Ile His Leu Phe Thr Leu Thr Asn Leu
    1325            1330                1335
Gly Ala Pro Ala Ala Phe Lys Tyr Phe Asp Thr Thr Ile Asp Arg
    1340            1345                1350
Lys Arg Tyr Thr Ser Thr Lys Glu Val Leu Asp Ala Thr Leu Ile
    1355            1360                1365
His Gln Ser Ile Thr Gly Leu Tyr Glu Thr Arg Ile Asp Leu Ser
    1370            1375                1380
Gln Leu Gly Gly Asp Ser Pro Lys Lys Lys Arg Lys Val Glu Ala
    1385            1390                1395
Ser Glu Leu Ala Pro Gly Lys Lys Arg Pro Val Glu His Ser Pro
    1400            1405                1410
Val Glu Pro Asp Ser Ser Ser Gly Thr Gly Lys Ala Gly Gln Gln
    1415            1420                1425
```

-continued

Pro Ala Arg Lys Arg Leu Asn Phe Gly Gln Thr Gly Asp Ala Asp
    1430                1435                1440

Ser Val Pro Asp Pro Gln Pro Leu Gly Gln Pro Pro Ala Ala Pro
    1445                1450                1455

Ser Gly Leu Gly Thr Asn Thr Met Ala Thr Gly Ser Gly Ala Pro
    1460                1465                1470

Met Ala Asp Asn Asn Glu Gly Ala Asp Gly Val Gly Asn Ser Ser
    1475                1480                1485

Gly Asn Trp His Cys Asp Ser Thr Trp Met Gly Asp Arg Val Ile
    1490                1495                1500

Thr Thr Ser Thr Arg Thr Trp Ala Leu Pro Thr Tyr Asn Asn His
    1505                1510                1515

Leu Tyr Lys Gln Ile Ser Ser Gln Ser Gly Ala Ser Asn Asp Asn
    1520                1525                1530

His Tyr Phe Gly Tyr Ser Thr Pro Trp Gly Tyr Phe Asp Phe Asn
    1535                1540                1545

Arg Phe His Cys His Phe Ser Pro Arg Asp Trp Gln Arg Leu Ile
    1550                1555                1560

Asn Asn Asn Trp Gly Phe Arg Pro Lys Arg Leu Asn Phe Lys Leu
    1565                1570                1575

Phe Asn Ile Gln Val Lys Glu Val Thr Gln Asn Asp Gly Thr Thr
    1580                1585                1590

Thr Ile Ala Asn Asn Leu Thr Ser Thr Val Gln Val Phe Thr Asp
    1595                1600                1605

Ser Glu Tyr Gln Leu Pro Tyr Val Leu Gly Ser Ala His Gln Gly
    1610                1615                1620

Cys Leu Pro Pro Phe Pro Ala Asp Val Phe Met Val Pro Gln Tyr
    1625                1630                1635

Gly Tyr Leu Thr Leu Asn Asn Gly Ser Gln Ala Val Gly Arg Ser
    1640                1645                1650

Ser Phe Tyr Cys Leu Glu Tyr Phe Pro Ser Gln Met Leu Arg Thr
    1655                1660                1665

Gly Asn Asn Phe Thr Phe Ser Tyr Thr Phe Glu Asp Val Pro Phe
    1670                1675                1680

His Ser Ser Tyr Ala His Ser Gln Ser Leu Asp Arg Leu Met Asn
    1685                1690                1695

Pro Leu Ile Asp Gln Tyr Leu Tyr Tyr Leu Ser Arg Thr Asn Thr
    1700                1705                1710

Pro Ser Gly Thr Thr Thr Gln Ser Arg Leu Gln Phe Ser Gln Ala
    1715                1720                1725

Gly Ala Ser Asp Ile Arg Asp Gln Ser Arg Asn Trp Leu Pro Gly
    1730                1735                1740

Pro Cys Tyr Arg Gln Gln Arg Val Ser Lys Thr Ser Ala Asp Asn
    1745                1750                1755

Asn Asn Ser Glu Tyr Ser Trp Thr Gly Ala Thr Lys Tyr His Leu
    1760                1765                1770

Asn Gly Arg Asp Ser Leu Val Asn Pro Gly Pro Ala Met Ala Ser
    1775                1780                1785

His Lys Asp Asp Glu Glu Lys Phe Phe Pro Gln Ser Gly Val Leu
    1790                1795                1800

Ile Phe Gly Lys Gln Gly Ser Glu Lys Thr Asn Val Asp Ile Glu
    1805                1810                1815

Lys Val Met Ile Thr Asp Glu Glu Glu Ile Arg Thr Thr Asn Pro

```
                1820                1825                1830

Val Ala Thr Glu Gln Tyr Gly Ser Val Ser Thr Asn Leu Gln Arg
        1835                1840                1845

Gly Asn Arg Gln Ala Ala Thr Ala Asp Val Asn Thr Gln Gly Val
    1850                1855                1860

Leu Pro Gly Met Val Trp Gln Asp Arg Asp Val Tyr Leu Gln Gly
1865                1870                1875

Pro Ile Trp Ala Lys Ile Pro His Thr Asp Gly His Phe His Pro
    1880                1885                1890

Ser Pro Leu Met Gly Gly Phe Gly Leu Lys His Pro Pro Pro Gln
    1895                1900                1905

Ile Leu Ile Lys Asn Thr Pro Val Pro Ala Asn Pro Ser Thr Thr
    1910                1915                1920

Phe Ser Ala Ala Lys Phe Ala Ser Phe Ile Thr Gln Tyr Ser Thr
    1925                1930                1935

Gly Gln Val Ser Val Glu Ile Glu Trp Glu Leu Gln Lys Glu Asn
    1940                1945                1950

Ser Lys Arg Trp Asn Pro Glu Ile Gln Tyr Thr Ser Asn Tyr Asn
    1955                1960                1965

Lys Ser Val Asn Val Asp Phe Thr Val Asp Thr Asn Gly Val Tyr
    1970                1975                1980

Ser Glu Pro Arg Pro Ile Gly Thr Arg Tyr Leu Thr Arg Asn Leu
    1985                1990                1995

<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 5

Gly Gly Gly Ser
1

<210> SEQ ID NO 6
<211> LENGTH: 1333
<212> TYPE: PRT
<213> ORGANISM: Artificial Sequence
<220> FEATURE:
<223> OTHER INFORMATION: Synthetic Polypeptide

<400> SEQUENCE: 6

Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Asp Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Arg Tyr Thr Arg Arg Lys
                85                  90                  95

Asn Arg Ile Cys Tyr Leu Gln Glu Ile Phe Ser Asn Glu Met Ala Lys
            100                 105                 110
```

-continued

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
            275                 280                 285

Asp Thr Tyr Asp Asp Asp Leu Asp Asn Leu Leu Ala Gln Ile Gly Asp
        290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
        355                 360                 365

Glu Ile Phe Phe Asp Gln Ser Lys Asn Gly Tyr Ala Gly Tyr Ile Asp
370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
        435                 440                 445

Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
        515                 520                 525

Pro Lys His Ser Leu Leu Tyr Glu Tyr Phe Thr Val Tyr Asn Glu Leu

```
            530                 535                 540
Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                    565                 570                 575

Arg Lys Val Thr Val Lys Gln Leu Lys Glu Asp Tyr Phe Lys Lys Ile
                580                 585                 590

Glu Cys Phe Asp Ser Val Glu Ile Ser Gly Val Glu Asp Arg Phe Asn
            595                 600                 605

Ala Ser Leu Gly Thr Tyr His Asp Leu Leu Lys Ile Ile Lys Asp Lys
        610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                    645                 650                 655

Lys Thr Tyr Ala His Leu Phe Asp Asp Lys Val Met Lys Gln Leu Lys
                660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
        690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                    725                 730                 735

Gly Asp Ser Leu His Glu His Ile Ala Asn Leu Ala Gly Ser Pro Ala
                740                 745                 750

Ile Lys Lys Gly Ile Leu Gln Thr Val Lys Val Val Asp Glu Leu Val
            755                 760                 765

Lys Val Met Gly Arg His Lys Pro Glu Asn Ile Val Ile Glu Met Ala
        770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                    805                 810                 815

Lys Glu His Pro Val Glu Asn Thr Gln Leu Gln Asn Glu Lys Leu Tyr
                820                 825                 830

Leu Tyr Tyr Leu Gln Asn Gly Arg Asp Met Tyr Val Asp Gln Glu Leu
            835                 840                 845

Asp Ile Asn Arg Leu Ser Asp Tyr Asp Val Asp His Ile Val Pro Gln
        850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                    885                 890                 895

Lys Lys Met Lys Asn Tyr Trp Arg Gln Leu Leu Asn Ala Lys Leu Ile
                900                 905                 910

Thr Gln Arg Lys Phe Asp Asn Leu Thr Lys Ala Glu Arg Gly Gly Leu
            915                 920                 925

Ser Glu Leu Asp Lys Ala Gly Phe Ile Lys Arg Gln Leu Val Glu Thr
        930                 935                 940

Arg Gln Ile Thr Lys His Val Ala Gln Ile Leu Asp Ser Arg Met Asn
945                 950                 955                 960
```

```
Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
            980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
        1010                1015                1020

Leu Glu Ser Glu Phe Val Tyr Gly Asp Tyr Lys Val Tyr Asp Val
        1025                1030                1035

Arg Lys Met Ile Ala Lys Ser Glu Gln Glu Ile Gly Lys Ala Thr
        1040                1045                1050

Ala Lys Tyr Phe Phe Tyr Ser Asn Ile Met Asn Phe Phe Lys Thr
        1055                1060                1065

Glu Ile Thr Leu Ala Asn Gly Glu Ile Arg Lys Arg Pro Leu Ile
        1070                1075                1080

Glu Thr Asn Gly Glu Thr Gly Glu Ile Val Trp Asp Lys Gly Arg
        1085                1090                1095

Asp Phe Ala Thr Val Arg Lys Val Leu Ser Met Pro Gln Val Asn
        1100                1105                1110

Ile Val Lys Lys Thr Glu Val Gln Thr Gly Gly Phe Ser Lys Glu
        1115                1120                1125

Ser Ile Leu Pro Lys Arg Asn Ser Asp Lys Leu Ile Ala Arg Lys
        1130                1135                1140

Lys Asp Trp Asp Pro Lys Lys Tyr Gly Gly Phe Asp Ser Pro Thr
        1145                1150                1155

Val Ala Tyr Ser Val Leu Val Val Ala Lys Val Glu Lys Gly Lys
        1160                1165                1170

Ser Lys Lys Leu Lys Ser Val Lys Glu Leu Leu Gly Ile Thr Ile
        1175                1180                1185

Met Glu Arg Ser Ser Phe Glu Lys Asn Pro Ile Asp Phe Leu Glu
        1190                1195                1200

Ala Lys Gly Tyr Lys Glu Val Lys Lys Asp Leu Ile Ile Lys Leu
        1205                1210                1215

Pro Lys Tyr Ser Leu Phe Glu Leu Glu Asn Gly Arg Lys Cys Leu
        1220                1225                1230

Ser Tyr Glu Thr Glu Ile Leu Thr Val Glu Tyr Gly Leu Leu Pro
        1235                1240                1245

Ile Gly Lys Ile Val Glu Lys Arg Ile Glu Cys Thr Val Tyr Ser
        1250                1255                1260

Val Asp Asn Asn Gly Asn Ile Tyr Thr Gln Pro Val Ala Gln Trp
        1265                1270                1275

His Asp Arg Gly Glu Gln Glu Val Phe Glu Tyr Cys Leu Glu Asp
        1280                1285                1290

Gly Ser Leu Ile Arg Ala Thr Lys Asp His Lys Phe Met Thr Val
        1295                1300                1305

Asp Gly Gln Met Leu Pro Ile Asp Glu Ile Phe Glu Arg Glu Leu
        1310                1315                1320

Asp Leu Met Arg Val Asp Asn Leu Pro Asn
        1325                1330

<210> SEQ ID NO 7
<211> LENGTH: 803
```

<212> TYPE: PRT
<213> ORGANISM: Artificial Sequence
<220> FEATURE:
<223> OTHER INFORMATION: Synthetic Polypeptide

<400> SEQUENCE: 7

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Met Leu Ala Ser Ala Gly Glu Leu Gln Lys Gly
        35                  40                  45

Asn Glu Leu Ala Leu Pro Ser Lys Tyr Val Asn Phe Leu Tyr Leu Ala
    50                  55                  60

Ser His Tyr Glu Lys Leu Lys Gly Ser Pro Glu Asp Asn Glu Gln Lys
65                  70                  75                  80

Gln Leu Phe Val Glu Gln His Lys His Tyr Leu Asp Glu Ile Ile Glu
                85                  90                  95

Gln Ile Ser Glu Phe Ser Lys Arg Val Ile Leu Ala Asp Ala Asn Leu
            100                 105                 110

Asp Lys Val Leu Ser Ala Tyr Asn Lys His Arg Asp Lys Pro Ile Arg
        115                 120                 125

Glu Gln Ala Glu Asn Ile Ile His Leu Phe Thr Leu Thr Asn Leu Gly
    130                 135                 140

Ala Pro Ala Ala Phe Lys Tyr Phe Asp Thr Thr Ile Asp Arg Lys Arg
145                 150                 155                 160

Tyr Thr Ser Thr Lys Glu Val Leu Asp Ala Thr Leu Ile His Gln Ser
                165                 170                 175

Ile Thr Gly Leu Tyr Glu Thr Arg Ile Asp Leu Ser Gln Leu Gly Gly
            180                 185                 190

Asp Ser Pro Lys Lys Lys Arg Lys Val Glu Ala Ser Gly Ser Ala Pro
        195                 200                 205

Gly Lys Lys Arg Pro Val Glu His Ser Pro Val Glu Pro Asp Ser Ser
    210                 215                 220

Ser Gly Thr Gly Lys Ala Gly Gln Gln Pro Ala Arg Lys Arg Leu Asn
225                 230                 235                 240

Phe Gly Gln Thr Gly Asp Ala Asp Ser Val Pro Asp Pro Gln Pro Leu
                245                 250                 255

Gly Gln Pro Pro Ala Ala Pro Ser Gly Leu Gly Thr Asn Thr Met Ala
            260                 265                 270

Thr Gly Ser Gly Ala Pro Met Ala Asp Asn Asn Glu Gly Ala Asp Gly
        275                 280                 285

Val Gly Asn Ser Ser Gly Asn Trp His Cys Asp Ser Thr Trp Met Gly
    290                 295                 300

Asp Arg Val Ile Thr Thr Ser Thr Arg Thr Trp Ala Leu Pro Thr Tyr
305                 310                 315                 320

Asn Asn His Leu Tyr Lys Gln Ile Ser Ser Gln Ser Gly Ala Ser Asn
                325                 330                 335

Asp Asn His Tyr Phe Gly Tyr Ser Thr Pro Trp Gly Tyr Phe Asp Phe
            340                 345                 350

Asn Arg Phe His Cys His Phe Ser Pro Arg Asp Trp Gln Arg Leu Ile
        355                 360                 365

Asn Asn Asn Trp Gly Phe Arg Pro Lys Arg Leu Asn Phe Lys Leu Phe
    370                 375                 380
```

-continued

Asn Ile Gln Val Lys Glu Val Thr Gln Asn Asp Gly Thr Thr Thr Ile
385                 390                 395                 400

Ala Asn Asn Leu Thr Ser Thr Val Gln Val Phe Thr Asp Ser Glu Tyr
                405                 410                 415

Gln Leu Pro Tyr Val Leu Gly Ser Ala His Gln Gly Cys Leu Pro Pro
            420                 425                 430

Phe Pro Ala Asp Val Phe Met Val Pro Gln Tyr Gly Tyr Leu Thr Leu
        435                 440                 445

Asn Asn Gly Ser Gln Ala Val Gly Arg Ser Ser Phe Tyr Cys Leu Glu
    450                 455                 460

Tyr Phe Pro Ser Gln Met Leu Arg Thr Gly Asn Asn Phe Thr Phe Ser
465                 470                 475                 480

Tyr Thr Phe Glu Asp Val Pro Phe His Ser Ser Tyr Ala His Ser Gln
                485                 490                 495

Ser Leu Asp Arg Leu Met Asn Pro Leu Ile Asp Gln Tyr Leu Tyr Tyr
            500                 505                 510

Leu Ser Arg Thr Asn Thr Pro Ser Gly Thr Thr Thr Gln Ser Arg Leu
        515                 520                 525

Gln Phe Ser Gln Ala Gly Ala Ser Asp Ile Arg Asp Gln Ser Arg Asn
    530                 535                 540

Trp Leu Pro Gly Pro Cys Tyr Arg Gln Gln Arg Val Ser Lys Thr Ser
545                 550                 555                 560

Ala Asp Asn Asn Asn Ser Glu Tyr Ser Trp Thr Gly Ala Thr Lys Tyr
                565                 570                 575

His Leu Asn Gly Arg Asp Ser Leu Val Asn Pro Gly Pro Ala Met Ala
            580                 585                 590

Ser His Lys Asp Asp Glu Glu Lys Phe Phe Pro Gln Ser Gly Val Leu
        595                 600                 605

Ile Phe Gly Lys Gln Gly Ser Glu Lys Thr Asn Val Asp Ile Glu Lys
    610                 615                 620

Val Met Ile Thr Asp Glu Glu Ile Arg Thr Thr Asn Pro Val Ala
625                 630                 635                 640

Thr Glu Gln Tyr Gly Ser Val Ser Thr Asn Leu Gln Arg Gly Asn Arg
                645                 650                 655

Gln Ala Ala Thr Ala Asp Val Asn Thr Gln Gly Val Leu Pro Gly Met
            660                 665                 670

Val Trp Gln Asp Arg Asp Val Tyr Leu Gln Gly Pro Ile Trp Ala Lys
        675                 680                 685

Ile Pro His Thr Asp Gly His Phe His Pro Ser Pro Leu Met Gly Gly
    690                 695                 700

Phe Gly Leu Lys His Pro Pro Gln Ile Leu Ile Lys Asn Thr Pro
705                 710                 715                 720

Val Pro Ala Asn Pro Ser Thr Thr Phe Ser Ala Ala Lys Phe Ala Ser
                725                 730                 735

Phe Ile Thr Gln Tyr Ser Thr Gly Gln Val Ser Val Glu Ile Glu Trp
            740                 745                 750

Glu Leu Gln Lys Glu Asn Ser Lys Arg Trp Asn Pro Glu Ile Gln Tyr
        755                 760                 765

Thr Ser Asn Tyr Asn Lys Ser Val Asn Val Asp Phe Thr Val Asp Thr
    770                 775                 780

Asn Gly Val Tyr Ser Glu Pro Arg Pro Ile Gly Thr Arg Tyr Leu Thr
785                 790                 795                 800

Arg Asn Leu

<210> SEQ ID NO 8
<211> LENGTH: 816
<212> TYPE: PRT
<213> ORGANISM: Artificial Sequence
<220> FEATURE:
<223> OTHER INFORMATION: Synthetic Polypeptide

<400> SEQUENCE: 8

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Met Leu Ala Ser Ala Gly Glu Leu Gln Lys Gly
        35                  40                  45

Asn Glu Leu Ala Leu Pro Ser Lys Tyr Val Asn Phe Leu Tyr Leu Ala
    50                  55                  60

Ser His Tyr Glu Lys Leu Lys Gly Ser Pro Glu Asp Asn Glu Gln Lys
65                  70                  75                  80

Gln Leu Phe Val Glu Gln His Lys His Tyr Leu Asp Glu Ile Ile Glu
                85                  90                  95

Gln Ile Ser Glu Phe Ser Lys Arg Val Ile Leu Ala Asp Ala Asn Leu
            100                 105                 110

Asp Lys Val Leu Ser Ala Tyr Asn Lys His Arg Asp Lys Pro Ile Arg
        115                 120                 125

Glu Gln Ala Glu Asn Ile Ile His Leu Phe Thr Leu Thr Asn Leu Gly
    130                 135                 140

Ala Pro Ala Ala Phe Lys Tyr Phe Asp Thr Thr Ile Asp Arg Lys Arg
145                 150                 155                 160

Tyr Thr Ser Thr Lys Glu Val Leu Asp Ala Thr Leu Ile His Gln Ser
                165                 170                 175

Ile Thr Gly Leu Tyr Glu Thr Arg Ile Asp Leu Ser Gln Leu Gly Gly
            180                 185                 190

Asp Ser Pro Lys Lys Lys Arg Lys Val Glu Ala Ser Gly Gly Gly Gly
        195                 200                 205

Ser Gly Gly Gly Gly Ser Gly Gly Gly Ser Ala Pro Gly Lys Lys
    210                 215                 220

Arg Pro Val Glu His Ser Pro Val Glu Pro Asp Ser Ser Gly Thr
225                 230                 235                 240

Gly Lys Ala Gly Gln Gln Pro Ala Arg Lys Arg Leu Asn Phe Gly Gln
                245                 250                 255

Thr Gly Asp Ala Asp Ser Val Pro Asp Pro Gln Pro Leu Gly Gln Pro
            260                 265                 270

Pro Ala Ala Pro Ser Gly Leu Gly Thr Asn Thr Met Ala Thr Gly Ser
        275                 280                 285

Gly Ala Pro Met Ala Asp Asn Asn Glu Gly Ala Asp Gly Val Gly Asn
    290                 295                 300

Ser Ser Gly Asn Trp His Cys Asp Ser Thr Trp Met Gly Asp Arg Val
305                 310                 315                 320

Ile Thr Thr Ser Thr Arg Thr Trp Ala Leu Pro Thr Tyr Asn Asn His
                325                 330                 335

Leu Tyr Lys Gln Ile Ser Ser Gln Ser Gly Ala Ser Asn Asp Asn His
            340                 345                 350

Tyr Phe Gly Tyr Ser Thr Pro Trp Gly Tyr Phe Asp Phe Asn Arg Phe
        355                 360                 365
```

```
His Cys His Phe Ser Pro Arg Asp Trp Gln Arg Leu Ile Asn Asn Asn
    370                 375                 380

Trp Gly Phe Arg Pro Lys Arg Leu Asn Phe Lys Leu Phe Asn Ile Gln
385                 390                 395                 400

Val Lys Glu Val Thr Gln Asn Asp Gly Thr Thr Thr Ile Ala Asn Asn
                405                 410                 415

Leu Thr Ser Thr Val Gln Val Phe Thr Asp Ser Glu Tyr Gln Leu Pro
            420                 425                 430

Tyr Val Leu Gly Ser Ala His Gln Gly Cys Leu Pro Pro Phe Pro Ala
        435                 440                 445

Asp Val Phe Met Val Pro Gln Tyr Gly Tyr Leu Thr Leu Asn Asn Gly
    450                 455                 460

Ser Gln Ala Val Gly Arg Ser Ser Phe Tyr Cys Leu Glu Tyr Phe Pro
465                 470                 475                 480

Ser Gln Met Leu Arg Thr Gly Asn Asn Phe Thr Phe Ser Tyr Thr Phe
                485                 490                 495

Glu Asp Val Pro Phe His Ser Ser Tyr Ala His Ser Gln Ser Leu Asp
            500                 505                 510

Arg Leu Met Asn Pro Leu Ile Asp Gln Tyr Leu Tyr Tyr Leu Ser Arg
        515                 520                 525

Thr Asn Thr Pro Ser Gly Thr Thr Thr Gln Ser Arg Leu Gln Phe Ser
    530                 535                 540

Gln Ala Gly Ala Ser Asp Ile Arg Asp Gln Ser Arg Asn Trp Leu Pro
545                 550                 555                 560

Gly Pro Cys Tyr Arg Gln Gln Arg Val Ser Lys Thr Ser Ala Asp Asn
                565                 570                 575

Asn Asn Ser Glu Tyr Ser Trp Thr Gly Ala Thr Lys Tyr His Leu Asn
            580                 585                 590

Gly Arg Asp Ser Leu Val Asn Pro Gly Pro Ala Met Ala Ser His Lys
        595                 600                 605

Asp Asp Glu Glu Lys Phe Phe Pro Gln Ser Gly Val Leu Ile Phe Gly
    610                 615                 620

Lys Gln Gly Ser Glu Lys Thr Asn Val Asp Ile Glu Lys Val Met Ile
625                 630                 635                 640

Thr Asp Glu Glu Glu Ile Arg Thr Thr Asn Pro Val Ala Thr Glu Gln
                645                 650                 655

Tyr Gly Ser Val Ser Thr Asn Leu Gln Arg Gly Asn Arg Gln Ala Ala
            660                 665                 670

Thr Ala Asp Val Asn Thr Gln Gly Val Leu Pro Gly Met Val Trp Gln
        675                 680                 685

Asp Arg Asp Val Tyr Leu Gln Gly Pro Ile Trp Ala Lys Ile Pro His
    690                 695                 700

Thr Asp Gly His Phe His Pro Ser Pro Leu Met Gly Gly Phe Gly Leu
705                 710                 715                 720

Lys His Pro Pro Pro Gln Ile Leu Ile Lys Asn Thr Pro Val Pro Ala
                725                 730                 735

Asn Pro Ser Thr Thr Phe Ser Ala Ala Lys Phe Ala Ser Phe Ile Thr
            740                 745                 750

Gln Tyr Ser Thr Gly Gln Val Ser Val Glu Ile Glu Trp Glu Leu Gln
        755                 760                 765

Lys Glu Asn Ser Lys Arg Trp Asn Pro Glu Ile Gln Tyr Thr Ser Asn
    770                 775                 780
```

```
Tyr Asn Lys Ser Val Asn Val Asp Phe Thr Val Asp Thr Asn Gly Val
785                 790                 795                 800

Tyr Ser Glu Pro Arg Pro Ile Gly Thr Arg Tyr Leu Thr Arg Asn Leu
            805                 810                 815
```

<210> SEQ ID NO 9
<211> LENGTH: 816
<212> TYPE: PRT
<213> ORGANISM: Artificial Sequence
<220> FEATURE:
<223> OTHER INFORMATION: Synthetic Polypeptide

<400> SEQUENCE: 9

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Met Leu Ala Ser Ala Gly Glu Leu Gln Lys Gly
        35                  40                  45

Asn Glu Leu Ala Leu Pro Ser Lys Tyr Val Asn Phe Leu Tyr Leu Ala
    50                  55                  60

Ser His Tyr Glu Lys Leu Lys Gly Ser Pro Glu Asp Asn Glu Gln Lys
65                  70                  75                  80

Gln Leu Phe Val Glu Gln His Lys His Tyr Leu Asp Glu Ile Ile Glu
                85                  90                  95

Gln Ile Ser Glu Phe Ser Lys Arg Val Ile Leu Ala Asp Ala Asn Leu
            100                 105                 110

Asp Lys Val Leu Ser Ala Tyr Asn Lys His Arg Asp Lys Pro Ile Arg
        115                 120                 125

Glu Gln Ala Glu Asn Ile Ile His Leu Phe Thr Leu Thr Asn Leu Gly
    130                 135                 140

Ala Pro Ala Ala Phe Lys Tyr Phe Asp Thr Thr Ile Asp Arg Lys Arg
145                 150                 155                 160

Tyr Thr Ser Thr Lys Glu Val Leu Asp Ala Thr Leu Ile His Gln Ser
                165                 170                 175

Ile Thr Gly Leu Tyr Glu Thr Arg Ile Asp Leu Ser Gln Leu Gly Gly
            180                 185                 190

Asp Ser Pro Lys Lys Lys Arg Lys Val Glu Ala Ser Glu Ala Ala Ala
        195                 200                 205

Lys Glu Ala Ala Ala Lys Glu Ala Ala Ala Lys Ala Pro Gly Lys Lys
    210                 215                 220

Arg Pro Val Glu His Ser Pro Val Glu Pro Asp Ser Ser Ser Gly Thr
225                 230                 235                 240

Gly Lys Ala Gly Gln Gln Pro Ala Arg Lys Arg Leu Asn Phe Gly Gln
                245                 250                 255

Thr Gly Asp Ala Asp Ser Val Pro Asp Pro Gln Pro Leu Gly Gln Pro
            260                 265                 270

Pro Ala Ala Pro Ser Gly Leu Gly Thr Asn Thr Met Ala Thr Gly Ser
        275                 280                 285

Gly Ala Pro Met Ala Asp Asn Asn Glu Gly Ala Asp Gly Val Gly Asn
    290                 295                 300

Ser Ser Gly Asn Trp His Cys Asp Ser Thr Trp Met Gly Asp Arg Val
305                 310                 315                 320

Ile Thr Thr Ser Thr Arg Thr Trp Ala Leu Pro Thr Tyr Asn Asn His
                325                 330                 335
```

```
Leu Tyr Lys Gln Ile Ser Ser Gln Ser Gly Ala Ser Asn Asp Asn His
            340                 345                 350

Tyr Phe Gly Tyr Ser Thr Pro Trp Gly Tyr Phe Asp Phe Asn Arg Phe
        355                 360                 365

His Cys His Phe Ser Pro Arg Asp Trp Gln Arg Leu Ile Asn Asn Asn
    370                 375                 380

Trp Gly Phe Arg Pro Lys Arg Leu Asn Phe Lys Leu Phe Asn Ile Gln
385                 390                 395                 400

Val Lys Glu Val Thr Gln Asn Asp Gly Thr Thr Ile Ala Asn Asn
                405                 410                 415

Leu Thr Ser Thr Val Gln Val Phe Thr Asp Ser Glu Tyr Gln Leu Pro
            420                 425                 430

Tyr Val Leu Gly Ser Ala His Gln Gly Cys Leu Pro Pro Phe Pro Ala
            435                 440                 445

Asp Val Phe Met Val Pro Gln Tyr Gly Tyr Leu Thr Leu Asn Asn Gly
            450                 455                 460

Ser Gln Ala Val Gly Arg Ser Ser Phe Tyr Cys Leu Glu Tyr Phe Pro
465                 470                 475                 480

Ser Gln Met Leu Arg Thr Gly Asn Asn Phe Thr Phe Ser Tyr Thr Phe
            485                 490                 495

Glu Asp Val Pro Phe His Ser Ser Tyr Ala His Ser Gln Ser Leu Asp
            500                 505                 510

Arg Leu Met Asn Pro Leu Ile Asp Gln Tyr Leu Tyr Tyr Leu Ser Arg
            515                 520                 525

Thr Asn Thr Pro Ser Gly Thr Thr Thr Gln Ser Arg Leu Gln Phe Ser
            530                 535                 540

Gln Ala Gly Ala Ser Asp Ile Arg Asp Gln Ser Arg Asn Trp Leu Pro
545                 550                 555                 560

Gly Pro Cys Tyr Arg Gln Gln Arg Val Ser Lys Thr Ser Ala Asp Asn
                565                 570                 575

Asn Asn Ser Glu Tyr Ser Trp Thr Gly Ala Thr Lys Tyr His Leu Asn
            580                 585                 590

Gly Arg Asp Ser Leu Val Asn Pro Gly Pro Ala Met Ala Ser His Lys
            595                 600                 605

Asp Asp Glu Glu Lys Phe Phe Pro Gln Ser Gly Val Leu Ile Phe Gly
610                 615                 620

Lys Gln Gly Ser Glu Lys Thr Asn Val Asp Ile Glu Lys Val Met Ile
625                 630                 635                 640

Thr Asp Glu Glu Glu Ile Arg Thr Thr Asn Pro Val Ala Thr Glu Gln
                645                 650                 655

Tyr Gly Ser Val Ser Thr Asn Leu Gln Arg Gly Asn Arg Gln Ala Ala
            660                 665                 670

Thr Ala Asp Val Asn Thr Gln Gly Val Leu Pro Gly Met Val Trp Gln
            675                 680                 685

Asp Arg Asp Val Tyr Leu Gln Gly Pro Ile Trp Ala Lys Ile Pro His
            690                 695                 700

Thr Asp Gly His Phe His Pro Ser Pro Leu Met Gly Gly Phe Gly Leu
705                 710                 715                 720

Lys His Pro Pro Pro Gln Ile Leu Ile Lys Asn Thr Pro Val Pro Ala
                725                 730                 735

Asn Pro Ser Thr Thr Phe Ser Ala Ala Lys Phe Ala Ser Phe Ile Thr
            740                 745                 750

Gln Tyr Ser Thr Gly Gln Val Ser Val Glu Ile Glu Trp Glu Leu Gln
```

```
                 755                  760                 765
     Lys Glu Asn Ser Lys Arg Trp Asn Pro Glu Ile Gln Tyr Thr Ser Asn
                 770                  775                 780

Tyr Asn Lys Ser Val Asn Val Asp Phe Thr Val Asp Thr Asn Gly Val
     785                 790                 795                 800

Tyr Ser Glu Pro Arg Pro Ile Gly Thr Arg Tyr Leu Thr Arg Asn Leu
                     805                 810                 815

<210> SEQ ID NO 10
<211> LENGTH: 4700
<212> TYPE: DNA
<213> ORGANISM: Artificial Sequence
<220> FEATURE:
<223> OTHER INFORMATION: Synthetic Polynucleotide

<400> SEQUENCE: 10
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggcctct agaatggagg cggtactatg tagatgagaa    180
ttcaggagca aactgggaaa agcaactgct tccaaatatt tgtgattttt acagtgtagt     240
tttggaaaaa ctcttagcct accaattctt ctaagtgttt taaaatgtgg gagccagtac    300
acatgaagtt atagagtgtt ttaatgaggc ttaaatatttt accgtaacta tgaaatgcta    360
cgcatatcat gctgttcagg ctccgtggcc acgcaactca tactaccggt gccaccatgt    420
acccatacga tgttccagat tacgcttcgc cgaagaaaaa gcgcaaggtc gaagcgtccg    480
acaagaagta cagcatcggc ctggacatcg gcaccaactc tgtgggctgg gccgtgatca    540
ccgacgagta caaggtgccc agcaagaaat tcaaggtgct gggcaacacc gaccggcaca    600
gcatcaagaa gaacctgatc ggagccctgc tgttcgacag cggcgaaaca gccgaggcca    660
cccggctgaa gagaaccgcc agaagaagat acaccagacg gaagaaccgg atctgctatc    720
tgcaagagat cttcagcaac gagatggcca aggtggacga cagcttcttc cacagactgg    780
aagagtcctt cctggtggaa gaggataaga agcacgagcg gcaccccatc ttcggcaaca    840
tcgtggacga ggtggcctac cacgagaagt accccaccat ctaccacctg agaaagaaac    900
tggtggacag caccgacaag gccgacctgc ggctgatcta tctggccctg gcccacatga    960
tcaagttccg gggccacttc ctgatcgagg gcgacctgaa ccccgacaac agcgacgtgg   1020
acaagctgtt catccagctg gtgcagacct acaaccagct gttcgaggaa aaccccatca   1080
acgccagcgg cgtggacgcc aaggccatcc tgtctgccag actgagcaag agcagacggc   1140
tggaaaatct gatcgcccag ctgcccggcg agaagaagaa tggcctgttc ggcaacctga   1200
ttgccctgag cctgggcctg accccccaact tcaagagcaa cttcgacctg gccgaggatg   1260
ccaaactgca gctgagcaag gacacctacg acgacgacct ggacaacctg ctggcccaga   1320
tcggcgacca gtacgccgac ctgtttctgg ccgccaagaa cctgtccgac gccatcctgc   1380
tgagcgacat cctgagagtg aacaccgaga tcaccaaggc cccctgagc gcctctatga   1440 tcaagagata cgacgagcac caccaggacc tgaccctgct gaaagctctc gtgcggcagc   1500
agctgcctga aagtacaaa gagatttct cgaccagaa caagaacggc tacgccggct     1560
acattgacgg cggagccagc caggaagagt tctacaagtt catcaagccc atcctggaaa   1620
agatggacgg caccgaggaa ctgctcgtga agctgaacag agaggacctg ctgcggaagc   1680
agcggacctt cgacaacggc agcatccccc accagatcca cctgggagag ctgcacgcca   1740
```

```
ttctgcggcg gcaggaagat ttttacccat tcctgaagga caaccgggaa aagatcgaga    1800
agatcctgac cttccgcatc ccctactacg tgggccctct ggccagggga acagcagat    1860 tcgcctggat gaccagaaag agcgaggaaa ccatcacccc ctggaacttc gaggaagtgg    1920
tggacaaggg cgcttccgcc cagagcttca tcgagcggat gaccaacttc gataagaacc    1980
tgcccaacga gaaggtgctg cccaagcaca gcctgctgta cgagtacttc accgtgtata    2040
acgagctgac caaagtgaaa tacgtgaccg agggaatgag aaagcccgcc ttcctgagcg    2100
gcgagcagaa aaaggccatc gtggacctgc tgttcaagac caaccggaaa gtgaccgtga    2160
agcagctgaa agaggactac ttcaagaaaa tcgagtgctt cgactccgtg gaaatctccg    2220
gcgtggaaga tcggttcaac gcctccctgg gcacatacca cgatctgctg aaaattatca    2280
aggacaagga cttcctggac aatgaggaaa acgaggacat tctggaagat atcgtgctga    2340
ccctgacact gtttgaggac agagagatga tcgaggaacg gctgaaaacc tatgcccacc    2400
tgttcgacga caaagtgatg aagcagctga agcggcggag ataccaccgg tggggcaggc    2460
tgagccggaa gctgatcaac ggcatccggg acaagcagtc cggcaagaca atcctggatt    2520
tcctgaagtc cgacggcttc gccaacagaa acttcatgca gctgatccac gacgacagcc    2580
tgacctttaa agaggacatc cagaaagccc aggtgtccgg ccagggcgat agcctgcacg    2640
agcacattgc caatctggcc ggcagccccg ccattaagaa gggcatcctg cagacagtga    2700
aggtggtgga cgagctcgtg aaagtgatgg gccggcacaa gcccgagaac atcgtgatcg    2760
aaatggccag agagaaccag accacccaga gggacagaa gaacagccgc gagagaatga    2820
agcggatcga gagggcatc aaagagctgg gcagccagat cctgaaagaa cacccgtgg    2880 aaaacaccca gctgcagaac gagaagctgt acctgtacta cctgcagaat gggcgggata    2940
tgtacgtgga ccaggaactg gacatcaacc ggctgtccga ctacgatgtg gaccatatcg    3000
tgcctcagag ctttctgaag gacgactcca tcgacaacaa ggtgctgacc agaagcgaca    3060
agaaccgggg caagagcgac aacgtgccct ccgaagaggt cgtgaagaag atgaagaact    3120
actggcggca gctgctgaac gccaagctga ttacccagag aaagttcgac aatctgacca    3180
aggccgagag aggcggcctg agcgaactgg ataaggccgg cttcatcaag agacagctgg    3240
tggaaacccg gcagatcaca aagcacgtgg cacagatcct ggactcccgg atgaacacta    3300
agtacgacga gaatgacaag ctgatccggg aagtgaaagt gatcaccctg aagtccaagc    3360
tggtgtccga tttccggaag gatttccagt tttacaaagt gcgcgagatc aacaactacc    3420
accacgccca cgacgcctac ctgaacgccg tcgtgggaac cgccctgatc aaaaagtacc    3480
ctaagctgga aagcgagttc gtgtacggcg actacaaggt gtacgacgtg cggaagatga    3540
tcgccaagag cgagcaggaa atcggcaagg ctaccgccaa gtacttcttc tacagcaaca    3600
tcatgaactt tttcaagacc gagattaccc tggccaacgg cgagatccgg aagcggcctc    3660
tgatcgagac aaacgcgaa accggggaga tcgtgtggga taagggccgg gattttgcca    3720
ccgtgcggaa agtgctgagc atgccccaag tgaatatcgt gaaaaagacc gaggtgcaga    3780
caggcggctt cagcaaagag tctatcctgc caagaggaa cagcgataag ctgatcgcca    3840
gaaagaagga ctgggaccct aagaagtacg gcggcttcga cagcccaccc gtggcctatt    3900
ctgtgctggt ggtggccaaa gtggaaaagg gcaagtccaa gaaactgaag agtgtgaaag    3960
agctgctggg gatcaccatc atggaaagaa gcagcttcga gaagaatccc atcgactttc    4020
tggaagccaa gggctacaaa gaagtgaaaa aggacctgat catcaagctg cctaagtact    4080
ccctgttcga gctggaaaac ggccggaagt gtctgtcgta tgagaccgag atcctgaccg    4140
```

```
tggagtatgg actgctgccg attggaaaga ttgtggagaa gcgcattgag tgcaccgtgt    4200
acagcgtgga taacaatggc aacatctata cacagccagt ggcccagtgg cacgaccgcg    4260
gagagcagga ggtcttcgag tactgcctgg aggatggcag cctgattcgc gccaccaagg    4320
atcataagtt catgacggtg gacggacaga tgctgcccat cgatgagatt tttgagcgcg    4380
agctggatct gatgcgcgtg gataacctgc cgaattaaga attcgatctt tttccctctg    4440
ccaaaaatta tggggacatc atgaagcccc ttgagcatct gacttctggc taataaagga    4500
aatttatttt cattgcaata gtgtgttgga attttttgtg tctctcactc ggcggccgca    4560 ggaacccta gtgatggagt tggccactcc ctctctgcgc gctcgctcgc tcactgaggc    4620
cgggcgacca aggtcgcccg acgcccggg ctttgcccgg gcggcctcag tgagcgagcg    4680
agcgcgcagc tgcctgcagg                                                4700

<210> SEQ ID NO 11
<211> LENGTH: 3338
<212> TYPE: DNA
<213> ORGANISM: Artificial Sequence
<220> FEATURE:
<223> OTHER INFORMATION: Synthetic Polynucleotide

<400> SEQUENCE: 11
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctctc tggctaacta     600
gagaacccac tgcttactgg cttatcgaaa ttaatacgac tcactatagg gagacccaag     660
ctggctagcg ccaccatgat caagattgcc acgcgcaagt acctgggcaa gcagaacgtg     720
tacgacatcg gagtggagcg cgatcacaac tttgccctga gaatggctt tattgcctcg     780 aactgtatgc tggcctctgc cggcgaactg cagaagggaa cgaactggc cctgccctcc     840 aaatatgtga acttcctgta cctggccagc cactatgaga agctgaaggg ctcccccgag     900
gataatgagc agaaacagct gtttgtggaa cagcacaagc actacctgga cgagatcatc     960
gagcagatca gcgagttctc caagagagtg atcctggccg acgctaatct ggacaaagtg    1020
ctgtccgcct acaacaagca ccgggataag cccatcagag agcaggccga gaatatcatc    1080
cacctgttta cctgaccaa tctgggagcc cctgccgcct tcaagtactt tgacaccacc    1140
atcgaccgga gaggtacac cagcaccaaa gaggtgctgg acgccaccct gatccaccag    1200
agcatcaccg gcctgtacga gacacggatc gacctgtctc agctggggagg cgacagcccc    1260 aagaagaaga gaaaggtgga ggccagcgga tccgctccgg gaaaaaagag gccggtagag    1320
cactctcctg tggagccaga ctcctcctcg ggaaccggaa aggcgggcca gcagcctgca    1380
agaaaaagat tgaattttgg tcagactgga gacgcagact cagtacctga ccccagcct    1440
```

```
ctcggacagc caccagcagc cccctctggt ctgggaacta atacgatggc tacaggcagt    1500
ggcgcaccaa tggcagacaa taacgagggc gccgacggag tgggtaattc ctcgggaaat    1560
tggcattgcg attccacatg gatgggcgac agagtcatca ccaccagcac ccgaacctgg    1620
gccctgccca cctacaacaa ccacctctac aaacaaattt ccagccaatc aggagcctcg    1680
aacgacaatc actactttgg ctacagcacc ccttgggggt attttgactt caacagattc    1740
cactgccact tttcaccacg tgactggcaa agactcatca caacaactg gggattccga     1800 cccaagagac tcaacttcaa gctctttaac attcaagtca aagaggtcac gcagaatgac    1860
ggtacgacga cgattgccaa taaccttacc agcacggttc aggtgtttac tgactcggag    1920
taccagctcc cgtacgtcct cggctcggcg catcaaggat gcctcccgcc gttcccagca    1980
gacgtcttca tggtgccaca gtatggatac ctcaccctga caacgggag tcaggcagta     2040 ggacgctctt cattttactg cctggagtac tttccttctc agatgctgcg taccggaaac    2100
aactttacct tcagctacac ttttgaggac gttcctttcc acagcagcta cgctcacagc    2160
cagagtctgg accgtctcat gaatcctctc atcgaccagt acctgtatta cttgagcaga    2220
acaaacactc caagtggaac caccacgcag tcaaggcttc agttttctca ggccggagcg    2280
agtgacattc gggaccagtc taggaactgg cttcctggac cctgttaccg ccagcagcga    2340
gtatcaaaga catctgcgga taacaacaac agtgaatact cgtggactgg agctaccaag    2400
taccacctca atggcagaga ctctctggtg aatccgggcc cggccatggc aagccacaag    2460
gacgatgaag aaaagttttt tcctcagagc ggggttctca tctttgggaa gcaaggctca    2520
gagaaaacaa atgtggacat tgaaaaggtc atgattacag acgaagagga aatcaggaca    2580
accaatcccg tggctacgga gcagtatggt tctgtatcta ccaacctcca gagaggcaac    2640
agacaagcag ctaccgcaga tgtcaacaca caaggcgttc ttccaggcat ggtctggcag    2700
gacagagatg tgtaccttca ggggcccatc tgggcaaaga ttccacacac ggacggacat    2760 tttcaccccct ctccctcat gggtggattc ggacttaaac accctcctcc acagattctc    2820
atcaagaaca ccccggtacc tgcgaatcct tcgaccacct tcagtgcggc aaagtttgct    2880
tccttcatca cacagtactc cacgggacag gtcagcgtgg agatcgagtg ggagctgcag    2940
aaggaaaaca gcaaacgctg gaatcccgaa attcagtaca cttccaacta caacaagtct    3000
gttaatgtgg actttactgt ggacactaat ggcgtgtatt cagagcctcg ccccattggc    3060
accagatacc tgactcgtaa tctgtaagaa ttaaacccgc tgatcagcct cgactgtgcc    3120
ttctagttgc cagccatctg ttgtttgccc ctccccgtg ccttccttga ccctggaagg     3180
tgccactccc actgtccttt cctaataaaa tgaggaaatt gcatcgcatt gtctgagtag    3240
gtgtcattct attctggggg gtggggtggg gcaggacagc aagggggagg attgggaaga    3300
caatagcagg catgctgggg atgcggtggg ctctatgg                            3338
```

<210> SEQ ID NO 12
<211> LENGTH: 3377
<212> TYPE: DNA
<213> ORGANISM: Artificial Sequence
<220> FEATURE:
<223> OTHER INFORMATION: Synthetic Polynucleotide

<400> SEQUENCE: 12

```
gttgacattg attattgact agttattaat agtaatcaat tacgggtca ttagttcata      60 gcccatatat ggagttccgc gttacataac ttacggtaaa tggcccgcct ggctgaccgc    120
ccaacgaccc ccgcccattg acgtcaataa tgacgtatgt tcccatagta acgccaatag    180
```

```
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagcg ccaccatgat caagattgcc acgcgcaagt acctgggcaa gcagaacgtg    720
tacgacatcg gagtggagcg cgatcacaac tttgccctga agaatggctt tattgcctcg    780
aactgtatgc tggcctctgc cggcgaactg cagaagggaa acgaactggc cctgccctcc    840
aaatatgtga acttcctgta cctggccagc cactatgaga agctgaaggg ctcccccgag    900
gataatgagc agaaacagct gtttgtggaa cagcacaagc actacctgga cgagatcatc    960
gagcagatca gcgagttctc caagagagtg atcctggccg acgctaatct ggacaaagtg    1020
ctgtccgcct acaacaagca ccgggataag cccatcagag agcaggccga gaatatcatc    1080
cacctgttta ccctgaccaa tctgggagcc ctgccgcct tcaagtactt tgacaccacc    1140
atcgaccgga gaggtacac cagcaccaaa gaggtgctgg acgccaccct gatccaccag    1200
agcatcaccg gcctgtacga gacacggatc gacctgtctc agctgggagg cgacagcccc    1260
aagaagaaga gaaaggtgga ggccagcggt ggcggcggtt caggcggagg tggctctggg    1320
ggcgggggtt ctgctccggg aaaaaagagg ccggtagagc actctcctgt ggagccagac    1380
tcctcctcgg gaaccggaaa ggcgggccag cagcctgcaa gaaaaagatt gaattttggt    1440
cagactggag acgcagactc agtacctgac ccccagcctc tcggacagcc accagcagcc    1500
ccctctggtc tgggaactaa tacgatggct acaggcagtg gcgcaccaat ggcagacaat    1560
aacgagggcg ccgacggagt gggtaattcc tcgggaaatt ggcattgcga ttccacatgg    1620
atgggcgaca gagtcatcac caccagcacc cgaacctggg ccctgcccac ctacaacaac    1680
cacctctaca aacaaatttc cagccaatca ggagcctcga acgacaatca ctactttggc    1740
tacagcaccc cttgggggta ttttgacttc aacagattcc actgccactt ttcaccacgt    1800
gactggcaaa gactcatcaa caacaactgg ggattccgac ccaagagact caacttcaag    1860
ctctttaaca ttcaagtcaa agaggtcacg cagaatgacg gtacgacgac gattgccaat    1920
aaccttacca gcacggttca ggtgtttact gactcggagt accagctccc gtacgtcctc    1980
ggctcggcgc atcaaggatg cctcccgccg ttcccagcag acgtcttcat ggtgccacag    2040
tatggatacc tcaccctgaa caacgggagt caggcagtag acgctcttc attttactgc    2100 ctggagtact tccttctca gatgctgcgt accggaaaca actttacctt cagctacact    2160
tttgaggacg ttcctttcca cagcagctac gctcacagcc agagtctgga ccgtctcatg    2220
aatcctctca tcgaccagta cctgtattac ttgagcagaa caaacactcc aagtggaacc    2280
accacgcagt caaggcttca gttttctcag gccggagcga gtgacattcg ggaccagtct    2340
aggaactggc ttcctggacc ctgttaccgc cagcagcgag tatcaaagac atctgcggat    2400
aacaacaaca gtgaatactc gtggactgga gctaccaagt accacctcaa tggcagagac    2460
tctctggtga atccgggccc ggccatggca agccacaagg acgatgaaga aaagtttttt    2520
```

```
cctcagagcg gggttctcat ctttgggaag caaggctcag agaaaacaaa tgtggacatt       2580
gaaaaggtca tgattacaga cgaagaggaa atcaggacaa ccaatcccgt ggctacggag       2640
cagtatggtt ctgtatctac caacctccag agaggcaaca gacaagcagc taccgcagat       2700
gtcaacacac aaggcgttct tccaggcatg gtctggcagg acagagatgt gtaccttcag       2760
gggcccatct gggcaaagat tccacacacg gacggacatt ttcacccctc tccctcatg       2820 ggtggattcg gacttaaaca ccctcctcca cagattctca tcaagaacac cccggtacct       2880
gcgaatcctt cgaccacctt cagtgcggca agtttgctt ccttcatcac acagtactcc       2940
acgggacagg tcagcgtgga gatcgagtgg gagctgcaga aggaaaacag caaacgctgg       3000
aatcccgaaa ttcagtacac ttccaactac aacaagtctg ttaatgtgga ctttactgtg       3060
gacactaatg gcgtgtattc agagcctcgc cccattggca ccagatacct gactcgtaat       3120
ctgtaagaat taaacccgct gatcagcctc gactgtgcct tctagttgcc agccatctgt       3180
tgtttgcccc tccccgtgc cttccttgac cctggaaggt gccactccca ctgtcctttc       3240
ctaataaaat gaggaaattg catcgcattg tctgagtagg tgtcattcta ttctgggggg       3300
tggggtgggg caggacagca aggggagga ttgggaagac aatagcaggc atgctggga       3360 tgcggtgggc tctatgg                                                    3377

<210> SEQ ID NO 13
<211> LENGTH: 3377
<212> TYPE: DNA
<213> ORGANISM: Artificial Sequence
<220> FEATURE:
<223> OTHER INFORMATION: Synthetic Polynucleotide

<400> SEQUENCE: 13
gttgacattg attattgact agttattaat agtaatcaat tacggggtca ttagttcata         60
gcccatatat ggagttccgc gttacataac ttacggtaaa tggcccgcct ggctgaccgc        120
ccaacgaccc ccgcccattg acgtcaataa tgacgtatgt tcccatagta acgccaatag        180
ggactttcca ttgacgtcaa tgggtggact atttacggta aactgcccac ttggcagtac        240
atcaagtgta tcatatgcca agtacgcccc ctattgacgt caatgacggt aaatggcccg        300
cctggcatta tgcccagtac atgaccttat gggactttcc tacttggcag tacatctacg        360
tattagtcat cgctattacc atggtgatgc ggttttggca gtacatcaat gggcgtggat        420
agcggtttga ctcacgggga tttccaagtc tccacccat tgacgtcaat gggagtttgt        480
tttggcacca aaatcaacgg gactttccaa aatgtcgtaa caactccgcc ccattgacgc        540
aaatgggcgg taggcgtgta cggtgggagg tctatataag cagagctctc tggctaacta        600
gagaacccac tgcttactgg cttatcgaaa ttaatacgac tcactatagg gagacccaag        660
ctggctagcg ccaccatgat caagattgcc acgcgcaagt acctgggcaa gcagaacgtg        720
tacgacatcg gagtggagcg cgatcacaac tttgccctga gaatggctt tattgcctcg        780 aactgtatgc tggcctctgc cggcgaactg cagaagggaa acgaactggc cctgccctcc        840
aaatatgtga acttcctgta cctggccagc cactatgaga agctgaaggg ctcccccgag        900
gataatgagc agaaacagct gtttgtggaa cagcacaagc actacctgga cgagatcatc        960
gagcagatca gcgagttctc caagagagtg atcctggccg acgctaatct ggacaaagtg       1020
ctgtccgcct acaacaagca ccgggataag cccatcagag agcaggccga gaatatcatc       1080
cacctgttta ccctgaccaa tctgggagcc cctgccgcct tcaagtactt tgacaccacc       1140
atcgaccgga agaggtacac cagcaccaaa gaggtgctgg acgccaccct gatccaccag       1200
```

```
agcatcaccg gcctgtacga gacacggatc gacctgtctc agctgggagg cgacagcccc   1260
aagaagaaga gaaaggtgga ggccagcgag gcagcagcca agaggccgc  tgccaaggag   1320 gcagcggcta aagctccggg aaaaaagagg ccggtagagc actctcctgt ggagccagac   1380
tcctcctcgg gaaccggaaa ggcgggccag cagcctgcaa gaaaaagatt gaattttggt   1440
cagactggag acgcagactc agtacctgac ccccagcctc tcggacagcc accagcagcc   1500
ccctctggtc tgggaactaa tacgatggct acaggcagtg gcgcaccaat ggcagacaat   1560
aacgagggcg ccgacggagt gggtaattcc tcgggaaatt ggcattgcga ttccacatgg   1620
atgggcgaca gagtcatcac caccagcacc cgaacctggg ccctgcccac ctacaacaac   1680
cacctctaca acaaatttc  cagccaatca ggagcctcga cgacaatca  ctactttggc   1740 tacagcaccc cttgggggta ttttgacttc aacagattcc actgccactt ttcaccacgt   1800
gactggcaaa gactcatcaa caacaactgg ggattccgac ccaagagact caacttcaag   1860
ctctttaaca ttcaagtcaa agaggtcacg cagaatgacg gtacgacgac gattgccaat   1920
aaccttacca gcacggttca ggtgtttact gactcggagt accagctccc gtacgtcctc   1980
ggctcggcgc atcaaggatg cctcccgccg ttcccagcag acgtcttcat ggtgccacag   2040
tatggatacc tcaccctgaa caacgggagt caggcagtag gacgctcttc attttactgc   2100
ctggagtact tccttctca  gatgctgcgt accggaaaca actttacctt cagctacact   2160
tttgaggacg ttcctttcca cagcagctac gctcacagcc agagtctgga ccgtctcatg   2220
aatcctctca tcgaccagta cctgtattac ttgagcagaa caaacactcc aagtggaacc   2280
accacgcagt caaggcttca gttttctcag gccggagcga gtgacattcg ggaccagtct   2340
aggaactggc ttcctggacc ctgttaccgc cagcagcgag tatcaaagac atctgcggat   2400
aacaacaaca gtgaatactc gtggactgga gctaccaagt accacctcaa tggcagagac   2460
tctctggtga atccgggccc ggccatggca agcacaagg  acgatgaaga aaagtttttt   2520
cctcagagcg gggttctcat ctttgggaag caaggctcag agaaaacaaa tgtggacatt   2580
gaaaaggtca tgattacaga cgaagaggaa atcaggacaa ccaatcccgt ggctacggag   2640
cagtatggtt ctgtatctac caacctccag agaggcaaca gacaagcagc taccgcagat   2700
gtcaacacac aaggcgttct tccaggcatg gtctggcagg acagagatgt gtaccttcag   2760
gggcccatct gggcaaagat tccacacacg gacggacatt ttcaccc ctc tcccctcatg   2820 ggtggattcg gacttaaaca ccctcctcca cagattctca tcaagaacac cccggtacct   2880
gcgaatcctt cgaccaccct cagtgcggca aagtttgctt ccttcatcac acagtactcc   2940
acgggacagg tcagcgtgga gatcgagtgg gagctgcaga aggaaaacag caaacgctgg   3000
aatcccgaaa ttcagtacac ttccaactac aacaagtctg ttaatgtgga ctttactgtg   3060
gacactaatg gcgtgtattc agagcctcgc cccattggca ccagatacct gactcgtaat   3120
ctgtaagaat taaacccgct gatcagcctc gactgtgcct tctagttgcc agccatctgt   3180
tgtttgcccc tccccgtgc  cttccttgac cctggaaggt gccactccca ctgtcctttc   3240
ctaataaaat gaggaaattg catcgcattg tctgagtagg tgtcattcta ttctgggggg   3300
tggggtgggg caggacagca aggggggagga ttgggaagac aatagcaggc atgctgggga   3360
tgcggtgggc tctatgg                                                  3377
```

<210> SEQ ID NO 14
<211> LENGTH: 4
<212> TYPE: PRT

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: May be repeated more than twice

<400> SEQUENCE: 14

Glu Ala Ala Lys
1

<210> SEQ ID NO 15
<211> LENGTH: 1
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: May be repeated more than once

<400> SEQUENCE: 15

Gly
1

<210> SEQ ID NO 16
<211> LENGTH: 2
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: May be repeated more than once

<400> SEQUENCE: 16

Gly Ser
1

<210> SEQ ID NO 17
<211> LENGTH: 2
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: May be repeated more than once

<400> SEQUENCE: 17

Gly Ser
1

<210> SEQ ID NO 18
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: May be repeated more than once

<400> SEQUENCE: 18

Gly Gly Ser Gly
```

```
<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Glu Ala Ala Ala Lys Glu Ala Ala Ala Lys Glu Ala Ala Ala Lys
1               5                   10                  15
```

COMPOSITIONS AND METHODS FOR TRANSIENT DELIVERY OF NUCLEASES

RELATED APPLICATIONS

This application is a continuation under 35 U.S.C. § 120 of U.S. application Ser. No. 15/550,452, filed Aug. 11, 2017, entitled "COMPOSITIONS AND METHODS FOR TRANSIENT DELIVERY OF NUCLEASES", which is a national stage filing under 35 U.S.C. § 371 of International Patent Application Serial No. PCT/US2016/017886, filed Feb. 12, 2016, entitled "COMPOSITIONS AND METHODS FOR TRANSIENT DELIVERY OF NUCLEASES", which claims the benefit under 35 U.S.C. § 119(e) of U.S. Application Ser. No. 62/115,928, filed Feb. 13, 2015, entitled "COMPOSITIONS AND METHODS FOR TRANSIENT DELIVERY OF NUCLEASES"; the entire contents of each of which are incorporated herein by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Dec. 6, 2022, is named U012070069US02-SUBSEQ-KZM and is 97,889 bytes in size.

FIELD OF THE INVENTION

The disclosure in some aspects relates to isolated nucleic acids, compositions, and kits useful for protein delivery to cells.

BACKGROUND

Recently, gene editing using designer DNA sequence-specific nucleases emerged as a technology for both basic biomedical research and therapeutic development. Platforms based on three distinct types of endonucleases have been developed for gene editing, namely the zinc finger nuclease (ZFN), the transcription activator-like effector nuclease (TALEN), and the clustered regularly interspaced short palindromic repeat (CRISPR) associated endonuclease 9 (cas9). Each nuclease is capable of inducing a DNA double-stranded break (DSB) at specific DNA loci, thus triggering two DNA repair pathways. The non-homologous end joining (NHEJ) pathway generates random insertion/deletion (indel) mutations at the DSB, whereas the homology-directed repair (HDR) pathway repairs the DSB with the genetic information carried on a donor template. Therefore, these gene editing platforms are capable of manipulating genes at specific genomic loci in multiple ways, such as disrupting gene function, repairing a mutant gene to normal, and inserting DNA material.

Transforming the gene editing technology into therapeutic uses encounters several obstacles, including the concern over safety. Certain gene editing platforms have been shown to induce off-target DSBs throughout genomes, which is associated with genotoxicity. Such off-target effects not only stem from the intrinsic ambiguity of DNA sequence recognition by nucleases, but also attribute to the prolonged presence of an active gene editing system in a given cell. As a result, off-target DSBs accumulate over time, and ultimately lead to genotoxicity.

SUMMARY

Recent approaches to delivering nucleases to cells for gene editing have focused on delivering of expression vectors engineered to express the nucleases in target cells. However, these approaches have proved to be problematic in many instances due to genotoxicity resulting from to prolonged expression of gene editing system in vivo. To prevent such off-target genotoxicity due to prolonged presence of a gene editing system, several studies explored delivery of mRNA or protein instead of delivering the gene coding for the nucleases in cell culture. As a result, the gene editing system functions only in a short period of time until the nuclease mRNA or protein is naturally degraded inside cells, which has been shown to reduce off-target effects. However, delivery of mRNA or protein in vivo is a significant task, and the delivery efficiency is very limited with conventional techniques. In contrast, the present disclosure overcomes such genotoxicity and delivery issues by using viruses for transiently delivering nucleases to cells thereby fulfilling the task of inducing permanent gene editing in a transient manner such that the nucleases will degrade naturally. In some embodiments, the disclosure relates to the uses of a viral vector (e.g., an AAV) as a delivery vehicle to carry a nuclease (e.g., a Cas9 protein or other designer nuclease proteins) to cells.

In some embodiments, to avoid the potential genotoxicity due to prolonged expression of gene editing system in vivo, methods are provided herein to transiently deliver an endonuclease protein using recombinant adeno-associated viruses. In some embodiments, AAV capsid is used as a delivery vehicle to carry the Cas9 protein or other designer nuclease proteins.

In some aspects, the disclosure relates to an adeno-associated virus (AAV) capsid protein having a terminally grafted nuclease.

In some embodiments, the capsid protein is a VP2 capsid protein. In some embodiments, the terminally grafted nuclease is grafted to the N-terminus of the VP2 capsid protein. In some embodiments, the terminally grafted nuclease is grafted to the C-terminus of the VP2 capsid protein.

In some embodiments, the nuclease is selected from: Transcription Activator-like Effector Nucleases (TALENs), Zinc Finger Nucleases (ZFNs), engineered meganuclease, re-engineered homing endonucleases and a Cas-family nuclease. In some embodiments, the nuclease is a Cas-family nuclease selected from the group consisting of Cas9 and Cas7. In some embodiments, the nuclease is represented by SEQ ID NO: 2. In some embodiments, the nuclease is a polypeptide encoded by the nucleic acid sequence represented by SEQ ID NO: 1.

In some embodiments, the AAV capsid protein further comprises a linker conjugated to the C-terminus of the terminally grafted nuclease and the N-terminus of the VP2 protein. In some embodiments, the AAV capsid protein further comprises a linker conjugated to the N-terminus of the terminally grafted nuclease and the C-terminus of the VP2 protein.

In some embodiments, the AAV capsid protein have an terminally grafted nuclease is of a serotype derived from a non-human primate. In some embodiments, the AAV capsid protein has an terminally grafted nuclease is selected from: AAV1, AAV2, AAV3, AAV4, AAV5, AAV6, AAV7, AAV8, AAV9, AAV10, AAV11, and AAV12.

In some aspects, the disclosure relates to a recombinant adeno-associated virus (rAAV) comprising an adeno-associated virus (AAV) capsid protein having a terminally grafted nuclease.

In some embodiments, the rAAV comprises a transgene. In some embodiments, the transgene encodes a guide RNA.

In some embodiments, the guide RNA directs the nuclease to a cleavage site in a target nucleic acid.

In some embodiments, the AAV is an empty viral particle with no transgene.

In some aspects, the disclosure provides a composition comprising an rAAV as described by this document. In some embodiments, the composition further comprises a pharmaceutically acceptable carrier.

In some aspects, the disclosure relates to a nucleic acid encoding an AAV capsid protein having an terminally grafted nuclease. In some embodiments, a host cell contains the nucleic acid. In some embodiments, the host cell contains a nucleic acid encodes an AAV VP2 capsid protein having an terminally grafted nuclease. In some embodiments, the host cell further comprises one or more nucleic acids encoding VP1 and VP3 capsid proteins.

In some aspects, the disclosure relates to a composition comprising a host cell as described by this document and a sterile cell culture medium. In some aspects, the disclosure relates to a composition comprising a host cell as described by this document and a cryopreservative.

In some aspects, the disclosure relates to an isolated nucleic acid comprising a sequence represented by SEQ ID NO: 3.

In some aspects, the disclosure relates to an isolated nucleic acid encoding an AAV capsid protein having an amino acid sequence selected from the group consisting of: SEQ ID NOs: 2 and 4.

In some aspects, the disclosure relates to an isolated AAV capsid protein comprising an amino acid sequence selected from the group consisting of: SEQ ID NOs: 2 and 4.

In some aspects, the disclosure relates to a composition comprising an isolated AAV capsid protein as described by this document. In some embodiments, the composition further comprises a pharmaceutically acceptable carrier.

In some aspects, the disclosure relates to a kit for producing a rAAV, the kit comprising: a container housing an isolated nucleic acid having a sequence of SEQ ID NO: 1 or 3. In some embodiments, the kit further comprises instructions for producing the rAAV. In some embodiments, the kit further comprises at least one container housing a recombinant AAV vector, wherein the recombinant AAV vector comprises a transgene.

In some aspects, the disclosure relates to a kit comprising: a container housing a recombinant AAV having an isolated AAV capsid protein having an amino acid sequence as set forth in SEQ ID NO: 2 or 4.

In some aspects, the disclosure relates to a method of targeting genome editing in a cell, the method comprising: delivering to the cell a first recombinant adeno associated virus (rAAV) having an terminally-grafted nuclease on at least one capsid protein, wherein when present in the cell, the terminally-grafted nuclease is directed to a genomic cleavage site by a guide RNA.

In some embodiments of the method, the first rAAV comprises a transgene encoding the guide RNA.

In some embodiments, the method further comprises administering a second rAAV having a transgene encoding a guide RNA that directs the nuclease to a cleavage site in a target nucleic acid.

In some embodiments, the cell is present in a subject, and the first rAAV or second rAAV is administered to the subject intravenously, intravascularly, transdermally, intraocularly, intrathecally, orally, intramuscularly, subcutaneously, intranasally, or by inhalation, thereby delivering the first rAAV or second rAAV to the cell. In some embodiments, the subject is selected from a mouse, a rat, a rabbit, a dog, a cat, a sheep, a pig, and a non-human primate. In some embodiments, the subject is a human.

In some aspects, the disclosure relates to a composition comprising: i) a first recombinant adeno-associated virus (rAAV) having a terminally-grafted nuclease on at least one capsid protein; and ii) a second rAAV having a transgene encoding a guide RNA that directs the nuclease to a cleavage site in a target nucleic acid.

In some embodiments, the first rAAV is an empty viral particle. In some embodiments, the first rAAV has an terminally-grafted nuclease that is grafted to the C-terminus of a VP2 capsid protein of the rAAV.

In some aspects, the disclosure relates to an adeno-associated virus (AAV) capsid protein having a terminally grafted nuclease or fragment thereof, wherein the nuclease or fragment thereof comprises a terminally grafted intein.

In some aspects, the capsid protein is a VP2 capsid protein. In some embodiments, the intein is IntN or IntC. In some embodiments, the capsid protein is represented by any one of SEQ ID NO: 7 to 9.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows the HA tagged SpCas9 is fused to the N-terminus of VP2. The expression of this fusion protein is driven by the CMV promoter. BGHpA: bovine growth hormone polyadenylation signal. FIG. 1B depicts western blotting using anti-HA antibody showing the HA-tagged fusion protein (~230 kD, arrow) produced from transiently transfected HEK293 cells. HA tagged SpCas9 (~162 kD) is marked by the triangle. Star indicates a band of unknown origin, a likely degradation product from the fusion protein.

FIG. 2A shows the DNA repair reporter construct. The mutant GFP (GFPmut) carries a disruptive insertion (Ins), followed by out-of-frame (+3 frame) T2A and mCherry. In the presence of a functional gene editing system targeting Ins, +1 insertion by NHEJ shifts the T2A and mCherry to in-frame, resulting mCherry fluorescence. FIG. 2B shows the results of a reporter assay in HEK293 cells by co-transfection of the reporter construct and various plasmid as indicated. Both mCherry fluorescence and bright field images are shown. Scale bar=50 μM.

FIG. 3A shows the N-terminus and C-terminus Npu DnaE intein (IntN and IntC) are fused with SpCas9 and VP2, respectively. The IntC-VP2 is packaged into AAV virion. PTS occurs between the SpCas9-IntN fusion protein and the IntC-AAV chimeric virion to produce the SpCas9-AAV virion. FIG. 3B shows that in the first AAV vector, the AAV genome encodes the N-terminal portion of SpCas9 (SpCas9N) fused with IntN. The second AAV vector carries IntC and the C-terminal portion of SpCas9 fused to VP2. In vivo transduction of the first AAV vector produces the fusion protein SpCas9N-IntN, which is followed by delivery of the second vector. PTS occurs to reconstitute the full-length SpCas9 protein.

DETAILED DESCRIPTION

Figure 1A:
FIGS. 1A-1B show the SpCas9-VP2 fusion protein is produced in HEK293 cells.

Genome editing is a powerful tool for the interrogation and manipulation of biological functions within cells. For example, genome editing allows for the repair of mutant genes to normal function, disruption of gene function and the insertion of genetic material (e.g. DNA), all at specific genomic loci. However, several challenges associated with the delivery and prolonged expression of nucleases in cells, such as genotoxicity due to off-target cleavage of DNA, has limited the therapeutic effectiveness of gene editing platforms. The instant disclosure overcomes current limitations by providing compositions and methods that improve delivery of genome editing nucleases. Accordingly, in some aspects, the disclosure relates to viral proteins comprising a terminally grafted nucleases.

As used herein, "genome editing" refers to adding, disrupting or changing genomic sequences (e.g., a gene sequence). In some embodiments, genome editing is performed using engineered proteins and related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ). Exemplary genome editing technologies include, but are not limited to Transcription Activator-like Effector Nucleases (TALENs), Zinc Finger Nucleases (ZFNs), engineered meganuclease re-engineered homing endonucleases, the CRISPR/Cas system. In some embodiments, the gene editing technologies are proteins or molecules related to TALENs, including but not limited to transcription activator-like effectors (TALEs) and restriction endonucleases (e.g. FokI). In some embodiments, the gene editing technologies are proteins or molecules related to ZFNs, including but not limited to proteins comprising the Cys$_2$His$_2$ fold group (for example Zif268 (EGR1)), and restriction endonucleases (e.g. FokI). In some embodiments, the gene editing technologies are proteins or molecules related to the CRISPR/Cas system, including but not limited to Cas9, Cas6, dCas9, CRISPR RNA (crRNA) and trans-activating crRNA (tracrRNA).

As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), engineered meganucleases and CRISPR-associated proteins (Cas nucleases). In some embodiments, the nuclease is a ZFN. In some embodiments, the ZFN comprises a FokI cleavage domain. In some embodiments, the ZFN comprises Cys$_2$His$_2$ fold group. In some embodiments, the nuclease is a TALEN. In some embodiments, the TALEN comprises a FokI cleavage domain. In some embodiments, the nuclease is an engineered meganuclease.

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, Cas6 and dCas9. dCas9 is an engineered Cas protein that binds to a target locus but does not cleave said locus. In some embodiments, the nuclease is Cas9. In some embodiments, the Cas9 is derived from the bacteria *S. pyogenes* (SpCas9).

For the purpose of genome editing, the CRISPR system can be modified to combine the tracrRNA and crRNA in to a single guide RNA (sgRNA) or just (gRNA). As used herein, the term "guide RNA" or "gRNA" refers to a polynucleotide sequence that is complementary to a target sequence in a cell and associates with a Cas nuclease, thereby directing the Cas nuclease to the target sequence. In some embodiments, a gRNA ranges between 1 and 30 nucleotides in length. In some embodiments, a gRNA ranges between 5 and 25 nucleotides in length. In some embodiments, a gRNA ranges between 10 and 20 nucleotides in length. In some embodiments, a gRNA ranges between 14 and 18 nucleotides in length.

Aspects of the disclosure relate to SpCas9 grafted to an AAV2 capsid protein, VP2. However, in some embodiments, the same strategy can be applied in other contexts. For example, the SpCas9 can be replaced with any modified SpCas9 such as mutated or truncated forms, Cas9 proteins from other species and nucleases used in other gene editing platforms such as ZFNs and TALENs. In some embodiments, a nuclease terminally grafted to an AAV2 capsid protein may also be fused to another functional domain, for example single guide RNA (sgRNA).

Similarly, the AAV2 capsid protein VP2 may be replaced with VP2 of other AAV serotypes (e.g., AAV3, AAV3b, AAV4, AAV5, AAV6, AAV7, AAV8, AAV9, AAVrh8, AAV10, and variants thereof), or a suitable capsid protein of any viral vector. Thus, in some aspects, the disclosure relates to the viral delivery of a nuclease. Examples of viral vectors include retroviral vectors (e.g. Maloney murine leukemia virus, MML-V), adenoviral vectors (e.g. AD100), lentiviral vectors (HIV and FIV-based vectors), herpesvirus vectors (e.g. HSV-2). In some embodiments, the disclosure relates to adeno-associated viruses (AAVs). In some embodiments, a nuclease is grafted to or replaces all or a portion of a viral glycoprotein.

In some embodiments, SpCas-VP2 is incorporated into AAV2 capsid to form AAV virion. In some embodiments, the start codon of VP2 is mutated in the cap gene from the trans AAV production plasmid. In some embodiments, when Cas9 is fused to the N-terminus of VP2, the resulting Cas9-VP2 fusion protein is functional with respect to both productive AAV assembly and being an active component of the CRISPR/Cas9 gene editing system.

In some embodiments, a catalytically deficient form of the cas9 protein (dCas9) is fused with a C-terminal peptide domain that either activates or represses gene expression. In such embodiments, such a dCas9-effector fusion protein binds DNA in a sgRNA-guided manner.

In some aspects, the disclosure relates to the discovery that inteins can be utilized to rejoin (e.g., reconstitute) fragments or portions of gene editing proteins to generate a functional gene editing protein that is grafted onto an AAV capsid protein. As used herein, "intein" refers to a self-splicing protein intron (e.g., peptide) that ligates flanking N-terminal and C-terminal exteins (e.g., fragments to be joined). The use of certain inteins for joining heterologous protein fragments is described, for example, in Wood et al., J. Biol. Chem. 289(21); 14512-9 (2014). For example, when fused to separate protein fragments, the inteins IntN and IntC recognize each other, splice themselves out and simultaneously ligate the flanking N- and C-terminal exteins of the protein fragments to which they were fused, thereby reconstituting a full length protein from the two protein fragments. Other suitable inteins will be apparent to a person of skill in the art.

A nuclease protein fragment (e.g., Cas9 fragment) can vary in length. In some embodiments, a protein fragment ranges from 2 amino acids to about 1000 amino acids in length. In some embodiments, a protein fragment ranges from about 5 amino acids to about 500 amino acids in length. In some embodiments, a protein fragment ranges from about 20 amino acids to about 200 amino acids in length. In some embodiments, a protein fragment ranges from about 10 amino acids to about 100 amino acids in length. Suitable protein fragments of other lengths will be apparent to a person of skill in the art.

In some embodiments, a portion or fragment of a nuclease (e.g., a fragment of Cas9) is fused to an intein. The nuclease can be fused to the N-terminus or the C-terminus of the intein. In some embodiments, a portion or fragment of a nuclease (e.g., a fragment of Cas9) is fused to an intein and fused to an AAV capsid protein. The intein, nuclease and capsid protein can be fused together in any arrangement (e.g., nuclease-intein-capsid, intein-nuclease-capsid, capsid-intein-nuclease, etc.). In some embodiments, the N-terminus of an intein is fused to the C-terminus of a nuclease (e.g., Cas9) and the C-terminus of the intein is fused to the N-terminus of an AAV capsid protein.

In some embodiments, the IntN/IntC system is used to join fragments of a nuclease. In some embodiments, IntC is fused to the N-terminus of a nuclease (e.g., Cas9) fragment that is grafted to an AAV capsid protein. In some embodiments, IntN is fused to the C-terminus of a nuclease (e.g., Cas9) fragment. In some embodiments, a fragment of a nuclease fused to an intein is represented by SEQ ID NO: 6. In some embodiments, an AAV capsid protein comprising an intein fused to a fragment of a nuclease that has been terminally grafted to the AAV capsid protein is represented by any one of SEQ ID NO: 7 to 9.

Isolated AAV Capsid Proteins and Nucleic Acids Encoding the Same

AAVs disclosed herein are useful for creating vectors that facilitate delivery of nucleases to cells for human gene editing applications. Protein and amino acid sequences as well as other information regarding the AAVs capsid are set forth in the sequence listing.

In some embodiments, an AAV capsid having a terminally graft nuclease is provided that has an amino acid sequence represented by SEQ ID NO: 4. In some embodiments, an AAV capsid having a terminally graft nuclease is provided that is encoded by a nucleic acid sequence represented by SEQ ID NO: 3.

An example of an isolated nucleic acid that encodes an AAV capsid protein having a terminally graft nuclease is a nucleic acid having a sequence of: SEQ ID NO: 3 as well as nucleic acids having substantial homology thereto. In some embodiments, isolated nucleic acids that encode AAV capsids are provided that encode the VP2 protein portion of the amino acid sequence represented by SEQ ID NO: 3.

In some embodiments, nucleic acids are provided that encode an AAV capsid having a nuclease grafted within its capsid sequence (e.g., a AAV9 capsid) and up to 5, up to 10, up to 20, up to 30, up to 40, up to 50, up to 100 other amino acid alternations.

In some embodiments, a fragment (portion) of an isolated nucleic acid encoding a AAV capsid sequence may be useful for constructing a nucleic acid encoding a desired capsid sequence. Fragments may be of any appropriate length (e.g., at least 9, at least 18, at least 36, at least 72, at least 144, at least 288, at least 576, at least 1152 or more nucleotides in length). For example, a fragment of nucleic acid sequence encoding a variant amino acid (compared with a known AAV serotype) may be used to construct, or may be incorporated within, a nucleic acid sequence encoding an AAV capsid sequence to alter the properties of the AAV capsid. For example, a nucleic sequence encoding an AAV variant may comprise n amino acid variants (e.g., in which n=1, 2, 3, 4, 5, 6, 7, 8, 9, 10 or more) compared with a known AAV serotype (e.g., AAV9). A recombinant cap sequence may be constructed having one or more of the n amino acid variants by incorporating fragments of a nucleic acid sequence comprising a region encoding a variant amino acid into the sequence of a nucleic acid encoding the known AAV serotype. The fragments may be incorporated by any appropriate method, including using site directed mutagenesis. In some embodiments, polypeptide fragments that are not normally present in AAV capsid proteins may be incorporated into a recombinant cap sequence. In some embodiments, the polypeptide fragment is grafted onto the recombinant cap sequence. Thus, new AAV variants may be created having new properties.

As used herein, "grafting" refers to joining or uniting of at least two polymeric molecules. In some embodiments, the term grafting refers joining or uniting of at least two polymeric molecules such that one of the at least two molecules is inserted within another of the at least two molecules. In some embodiments, the term grafting refers to joining or uniting of at least two polymeric molecules such that one of the at least two molecules is appended to another of the at least two molecules. In some embodiments, the term grafting refers joining or uniting of at least two nucleic acid molecules such that one of the at least two nucleic acid molecules is inserted within another of the at least two nucleic acid molecules. In some embodiments, the term grafting refers to joining or uniting of at least two nucleic acid molecules such that one of the at least two molecules is appended to another of the at least two nucleic acid molecules.

In some embodiments, a grafted nucleic acid molecule encodes a chimeric protein. In some embodiments, a grafted nucleic acid molecule encodes a chimeric protein, such that one polypeptide is effectively inserted into another polypeptide (e.g. not directly conjugated before the N-terminus or after the C-terminus), thereby creating a contiguous fusion of two polypeptides. In some embodiments, a grafted nucleic acid molecule encodes a chimeric protein, such that one polypeptide is effectively appended to another polypeptide (e.g. directly conjugated before the N-terminus or after the C-terminus), thereby creating a contiguous fusion of two polypeptides. In some embodiments, the term grafting refers to joining or uniting of at least two polypeptides, or fragments thereof, such that one of the at least two polypeptides or fragments thereof is inserted within another of the at least two polypeptides or fragments thereof. In some embodiments, the term grafting refers to joining or uniting of at least two polypeptides or fragments thereof such that one of the at least two polypeptides or fragments thereof is appended to another of the at least two polypeptides or fragments thereof.

In some embodiments, the instant disclosure relates to an adeno-associated virus (AAV) capsid protein comprising a AAV capsid protein having an N-terminally grafted nuclease.

In some embodiments, the AAV capsid protein further comprises a linker. Non-limiting examples of linkers include flexible linkers (e.g. glycine-rich linkers), rigid linkers (e.g. [EAAK]$_n$, where n>2 (SEQ ID NO: 14)), and cleavable linkers (e.g. protease-sensitive sequences). Other linkers are disclosed, for example in Chen et al., Fusion protein linkers: Property, design and functionality. Advanced drug delivery reviews, 2013. In some embodiments, the linker is conjugated to the C-terminus of a terminally grafted nuclease (e.g., an N-terminally grafted nuclease). In some embodiments, the linker is conjugated to the N-terminus of the terminally grafted nuclease (e.g., an N-terminally grafted nuclease). In some embodiments, one linker is conjugated to the N-terminus of the terminally grafted nuclease and a second linker is conjugated to the C-terminus of the terminally grafted nuclease.

In some embodiments, the linker is a glycine-rich linker. In some embodiments, the linker comprises at least one polypeptide repeat, each repeat comprising at least 80% glycine residues. In some embodiments, the polypeptide repeat comprises GGGS (SEQ ID NO: 5).

In some embodiments, the linker comprises a formula selected from the group consisting of: [G]$_n$ (SEQ ID NO: 15), [G]$_n$S (SEQ ID NO: 16), [GS]$_n$ (SEQ ID NO: 17), and [GGSG]$_n$ (SEQ ID NO: 18), wherein G is glycine and wherein n is an integer greater than one (e.g., 2, 3, 4, 5, 6, 7, 8, 9, 10, 11, 12, 13, 14, 15, 16, 17, 18, 19, 20, 21, 22, 23, 24, 25 or more).

In some cases, fragments of capsid proteins disclosed herein are provided. Such fragments may at least 10, at least 20, at least 50, at least 100, at least 200, at least 300, at least 400, at least 500 or more amino acids in length. In some embodiments, chimeric capsid proteins are provided that comprise one or more fragments of one or more capsid proteins disclosed herein.

"Homology" refers to the percent identity between two polynucleotides or two polypeptide moieties. The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments between sequences of nucleic acids or polypeptides are performed using any of a variety of publicly or commercially available Multiple Sequence Alignment Programs, such as "Clustal W", accessible through Web Servers on the internet. Alternatively, Vector NTI utilities may also be used. There are also a number of algorithms known in the art which can be used to measure nucleotide sequence identity, including those contained in the programs described above. As another example, polynucleotide sequences can be compared using BLASTN, which provides alignments and percent sequence identity of the regions of the best overlap between the query and search sequences. Similar programs are available for the comparison of amino acid sequences, e.g., the "Clustal X" program, BLASTP. Typically, any of these programs are used at default settings, although one of skill in the art can alter these settings as needed. Alternatively, one of skill in the art can utilize another algorithm or computer program which provides at least the level of identity or alignment as that provided by the referenced algorithms and programs. Alignments may be used to identify corresponding amino acids between two proteins or peptides. A "corresponding amino acid" is an amino acid of a protein or peptide sequence that has been aligned with an amino acid of another protein or peptide sequence. Corresponding amino acids may be identical or non-identical. A corresponding amino acid that is a non-identical amino acid may be referred to as a variant amino acid.

Alternatively for nucleic acids, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAVs

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner. In some embodiments, the a terminally grafted nuclease is present on all three capsid proteins (e.g. VP1, VP2, VP3) of a rAAV. In some embodiments, the terminally grafted nuclease is present on two of the capsid proteins (e.g. VP2 and VP3) of a rAAV. In some embodiments, the terminally grafted nuclease is present on a single capsid protein of a rAAV. In some embodiments, the terminally grafted nuclease is present on the VP2 capsid protein of the rAAV.

In some embodiments, the instant disclosure relates to an adeno-associated virus (AAV) capsid protein comprising: an AAV capsid protein having an N-terminally grafted nuclease, wherein the AAV capsid protein is not of an AAV2 serotype. In some embodiments, the AAV capsid protein is of an AAV serotype selected from the group consisting of AAV3, AAV4, AAV5, AAV6, AAV8, AAVrh8 AAV9, and AAV10. In some embodiments, the capsid protein having an N-terminally grafted nuclease is a viral protein 2 (VP2) capsid protein. In some embodiments, the AAV capsid protein having a terminally grafted nuclease is of a serotype derived from a non-human primate. In some embodiments, the AAV capsid protein having a terminally grafted nuclease is of a AAVrh8 serotype. In some embodiments, the AAV capsid protein having an N-terminally grafted nuclease is of an AAV9, optionally AAV9.47, serotype.

In some aspects, the instant disclosure relates to the location within an AAV capsid protein where a nuclease is grafted. In some embodiments, the nuclease is N-terminally grafted to the capsid protein. In some embodiments, the nuclease is C-terminally grafted to a capsid protein. In some embodiments, a nuclease that is C-terminally grafted to a capsid protein (e.g., VP2) resides within the viral particle, and the viral particle does not contain a genome, e.g., a nucleic acid harboring a transgene.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a nuclease terminally grafted to a capsid protein that is operably linked to a promoter. In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV Vectors

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) comprising a capsid protein having an N-terminally grafted nuclease, wherein the N-terminally grafted nuclease is present only in the VP2 capsid protein. In some embodiments, the rAAV comprises a capsid protein having an amino acid sequence represented by SEQ ID NO: 4.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Also contemplated herein are methods of delivering a transgene to a subject using the rAAVs described herein. In some embodiments, the instant disclosure relates to a method for delivering a transgene to a subject comprising administering a rAAV to a subject, wherein the rAAV comprises: (i) a capsid protein having a terminally grafted nuclease, e.g., a nuclease having a sequence set forth as SEQ ID NO: 2, and optionally (ii) at least one transgene, e.g., a transgene encoding a gRNA, and wherein the rAAV infects cells of a target tissue of the subject. In some embodiments of the method, at least one transgene encodes a single guide RNA, a CRISPR RNA (crRNA), and/or a trans-activating crRNA (tracrRNA).

In some embodiments, the rAAV vectors may comprise a transgene, wherein the transgene is a gRNA. In some embodiments, the gRNA targets a nucleic acid sequence that causes disease in a subject. For example, expression of the huntingtin (Htt) gene causes Huntington's disease. Without wishing to be bound by any particular theory, a gRNA targeting the Htt gene directs Cas9 cleavage of the gene, thereby preventing its expression. Other similar genes (disease-associated or otherwise) can be targeted.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177, 403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

Aspects of the instant disclosure relate to compositions comprising a recombinant AAV comprising a capsid protein having a terminally grafted (e.g., N-terminally grafted or C-terminally grafted) nuclease. In some embodiments, the nuclease is terminally grafted onto a capsid protein. In some embodiments, the a terminally grafted nuclease is present on all three capsid proteins (e.g. VP1, VP2, VP3) of the rAAV. In some embodiments, the terminally grafted nuclease is present on two of the capsid proteins (e.g. VP2 and VP3) of the rAAV. In some embodiments, the terminally grafted nuclease is present on a single capsid protein of the rAAV. In some embodiments, the terminally grafted nuclease is present on the VP2 capsid protein of the rAAV. In some embodiments, the composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to 103 rAAV genome copies is appropriate. In certain embodiments, $10^{12}$ or $10^{13}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as iso-propylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid having a sequence of SEQ ID NO: 1 or SEQ ID NO: 3. In some embodiments, the kit further comprises instructions for producing the rAAV. In some embodiments, the kit further comprises at least one container housing a recombinant AAV vector, wherein the recombinant AAV vector comprises a transgene.

In some embodiments, the instant disclosure relates to a kit comprising a container housing a recombinant AAV having an isolated AAV capsid protein having an amino acid sequence as set forth in any of SEQ ID NO: 4.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E40RF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Overview

To avoid the potential genotoxicity due to prolonged expression gene editing components, an endonuclease protein is transiently delivered and degrades naturally in the cell. Specifically, AAV capsid is used as a delivery vehicle to carry a Cas9 protein or other designer nuclease protein. AAV capsid consists of 60 copies of three capsid proteins, VP1, VP2 and VP3, at a ratio of 1:1:18. Although AAV capsid adopts a tightly packed structure, it has been shown that the VP2 protein with an N-terminal fusion protein can be incorporated into AAV capsid, and such a chimeric AAV is infectious.

Example 1

Results provided herein indicate that when Cas9 is fused to the N-terminus of VP2 (FIG. 1A), the resulting Cas9-VP2 fusion protein is functional.

Figure 1B:
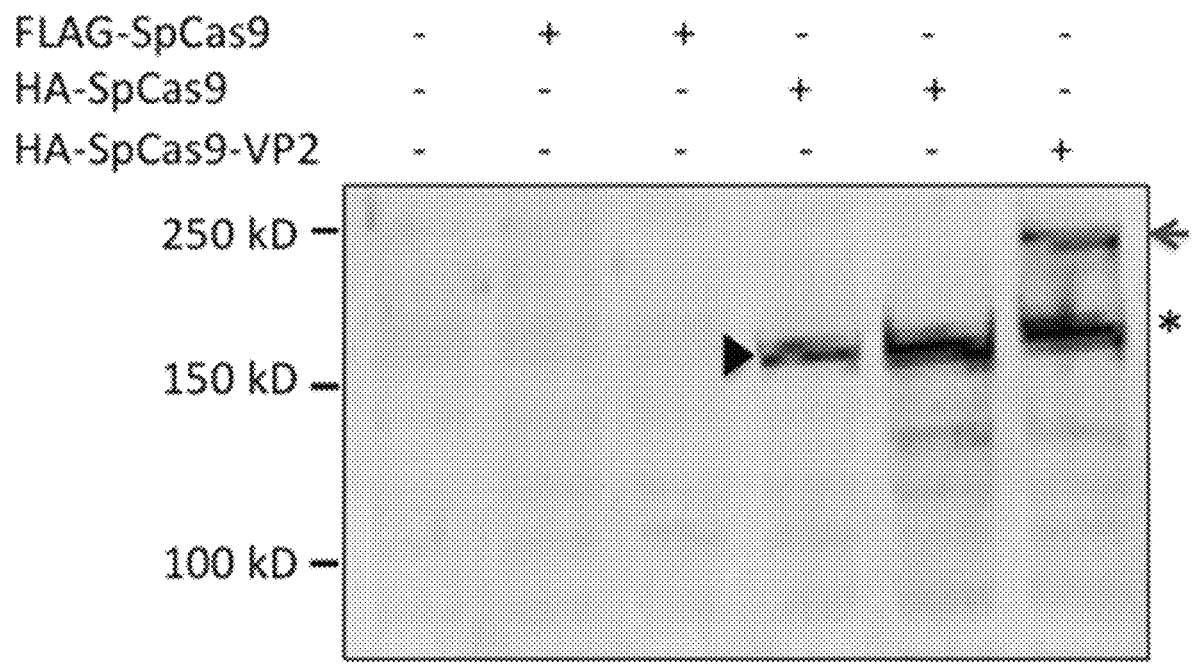
Figure 2A:
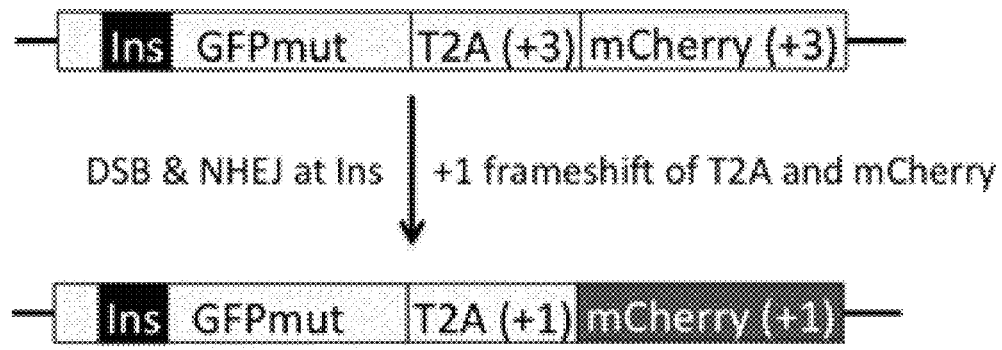
FIGS. 2A-2B show the SpCas9-VP2 fusion protein mediates gene editing in HEK293 cells.
Figure 2B:
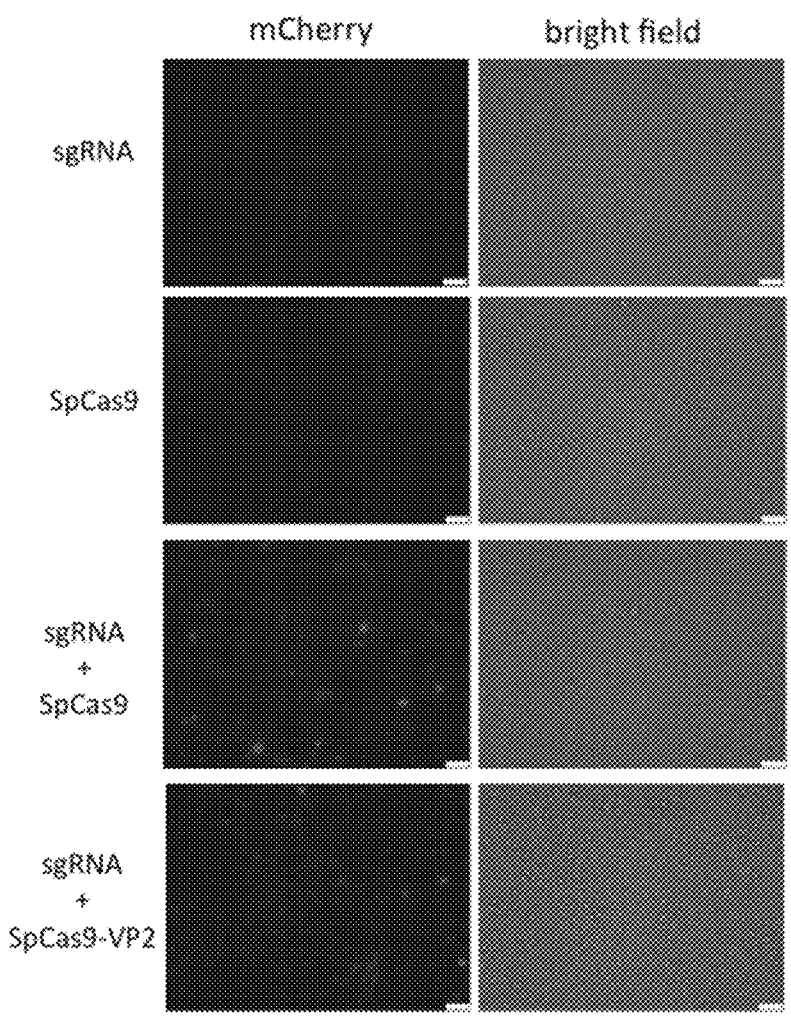

A plasmid expressing *S. pyogenes* Cas9 (SpCas9; SEQ ID NOs: 1 and 2) fused with AAV2 VP2 was constructed (FIG. 1A). The resulting construct is represented by SEQ ID NO: 3 and the fusion protein is represented by SEQ ID NO: 4. Transfection of the construct into HEK293 cells yields a fusion protein product of expected size, as demonstrated by western blotting (FIG. 1B). A fluorescence reporter assay as illustrated in FIG. 2A was used to test if SpCas9-VP2 can function in gene editing. In the reporter construct, the GFP is disrupted by an insertion. The downstream out-of-frame T2A, when shifted to in-frame, mediates translation termination and re-initiation to produce mCherry reporter protein. In the presence of the sgRNA targeting the insertion in the GFP sequence and a functional SpCas9, indels by NHEJ shift the downstream T2A and mCherry to in-frame, thus giving mCherry fluorescence signal. Using this reporter system, SpCas9-VP2 induction of NHEJ by co-transfection in HEK293 cells was tested (FIG. 2B). Negative control cells expressing SpCas9 only or sgRNA only did not induce mCherry signal. Positive control cells, co-expressing sgRNA and SpCas9 yielded mCherry signal. When sgRNA and the SpCas9-VP2 fusion were co-expressed, mCherry fluorescence was also observed, demonstrating that the SpCas-VP2 fusion protein behaves similarly as SpCas9 in inducing gene editing and NHEJ (FIG. 2B).

SpCas-VP2 can be also incorporated into AAV2 capsid to form AAV virion. The start codon of VP2 is mutated in the cap gene from the trans AAV production plasmid. The omission of VP2 expression from this plasmid in HEK293 cells is validated by western blotting using an antibody targeting a C-terminal epitope shared by VP1, VP2 and VP3. Small-scale AAV production is performed using the VP2 null-trans plasmid and the SpCas9-VP2 in replacement of the original trans plasmid to examine the presence of Cas9 protein covalently linked to the outer surface of AAV2 virion. ELISA is performed using antibodies recognizing a fully assembled AAV2 virion and the HA-tagged SpCas9. Alternatively, immuno electron microscopy is performed to visualize the presence of HA-tagged SpCas9 immunoreactivity outside of AAV2 virion. Next, a small-scale AAV production-infection assay is performed to validate that SpCas9-AAV delivers the SpCas9 into HEK293 cells and mediates gene editing. The same reporter system as illustrated in FIG. 2B is used for this assay.

Serials of in vivo experiments using SpCas9-AAV2 expressing EGFP and sgRNA targeting the mouse ROSA26 locus (SpCas9-AAV2-EGFP-sgROSA26) obtained from large-scale production are next performed. The tropism of SpCas9-AAV2 is characterized in mice by systemic delivery. Wild-type C57BL/6J mice are injected with SpCas9-AAV2-EGFP-sgROSA26 at postnatal day 1 (P1) via facial vein and at 8 weeks old via tail vein, respectively. The mice are sacrificed 3 weeks after injection and fixed. Tissues including liver, heart, skeletal muscle, pancreas, adrenal gland, kidneys, spleen, brain, and spinal cord are analyzed for EGFP expression by immunofluorescence staining. The best transduced tissue(s) are selected to demonstrate SpCas9-AAV mediated gene editing of ROSA26 locus in vivo in another group of mice treated in the same manner, from which fresh tissues are harvested and genomic DNA extracted. The gene editing events represented by random indels near the sgRNA targeting site in the ROSA26 locus are investigated using Surveyor assay and single DNA molecule sequencing.

To demonstrate the improved safety profile of the SpCas9 transiently delivered using SpCas9-AAV2 and contrast with prolonged expression of SpCas9 from a conventional rAAV2 vector, SpCas9-AAV2 are packaged with transgene cassettes expressing sgRNAs with reported off-target effects in mouse genome, and inject into mice. The gene editing events at both on- and off-target genomic DNA loci are analyzed by Surveyor assay and single DNA molecule sequencing. Transient delivery of SpCas9 significantly reduces the chance of off-target effect.

Example 2

Figure 3A:
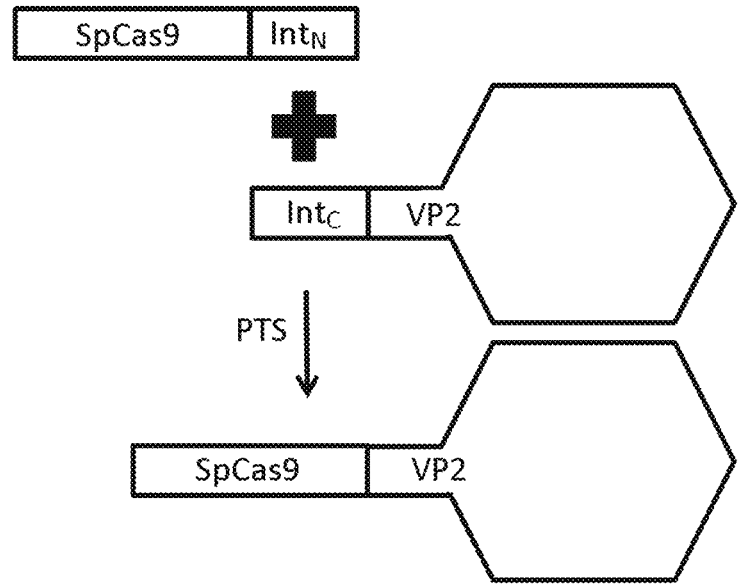
FIGS. 3A-3B show alternative strategies utilizing intein-mediated protein trans-splicing (PTS).

Intein-mediated protein trans-splicing (PTS) is used to fuse SpCas9 protein with VP2 after AAV assembly as illustrated in FIG. 3A. For example, the naturally split intein Npu DnaE, which has the most robust trans-splicing activity identified so far, is used to fuse SpCas9 protein with VP2 by PTS. The SpCas9 carries IntN, and VP2 carries IntC. Since IntC comprises only 36 amino acid residues, an IntC-VP2 fusion is amenable to AAV assembly. First, IntC-AAV2 virion and SpCas9-IntN protein are produced and purified separately, and then incubated to allow for PTS to occur in vitro. Intein-mediated PTS is a spontaneous reaction and does not require other co-factors. The fast kinetic nature of Npu DnaE split intein produces SpCas9-AAV2 fusion protein rapidly. The fusion protein is further purified by dialysis.

Figure 3B:
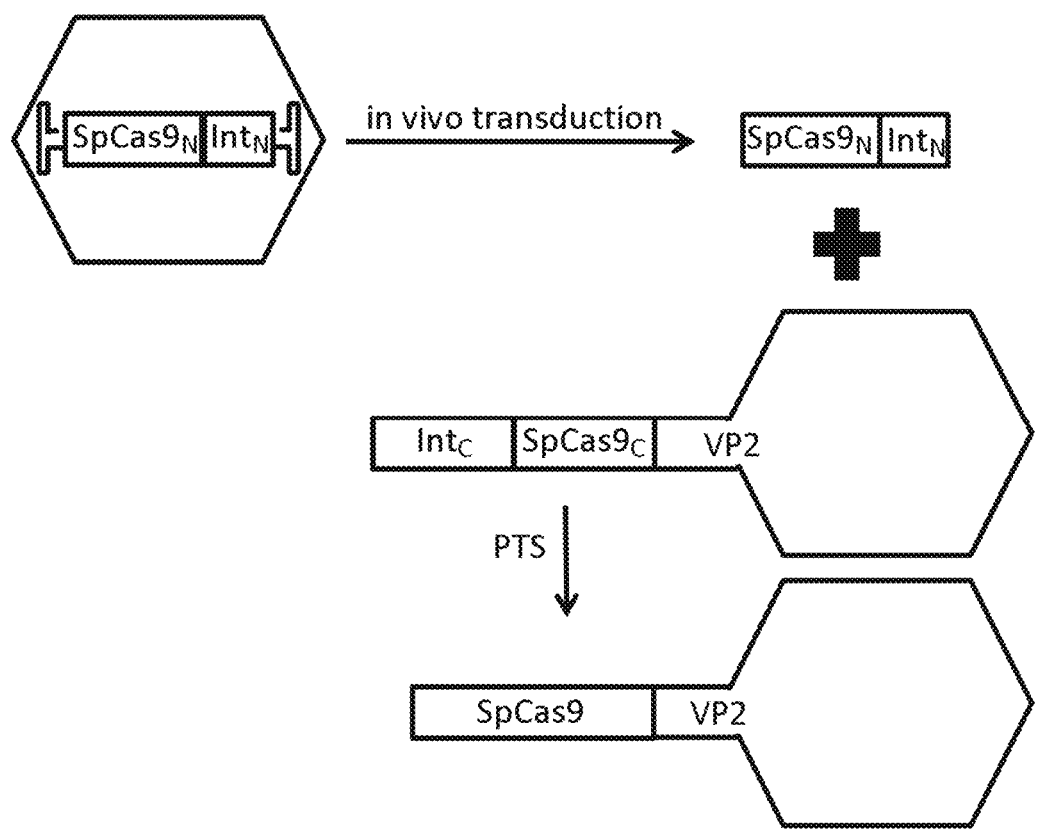

Alternatively, IntC is fused with a truncated C-terminal portion of SpCas9 onto AAV2 capsid to allow for in vivo transduction. The rest portion of SpCas9 and IntN are encoded by a transgene expression cassette as rAAV genome (FIG. 3B). Co-delivery of the two portions of SpCas9 reconstitutes the full-length, functional SpCas9. Importantly, as the IntC-SpCas9C protein is degraded naturally, the long-term expression of SpCas9N-IntN only is non-functional, thus mitigating off-target effects.

Figure 4:
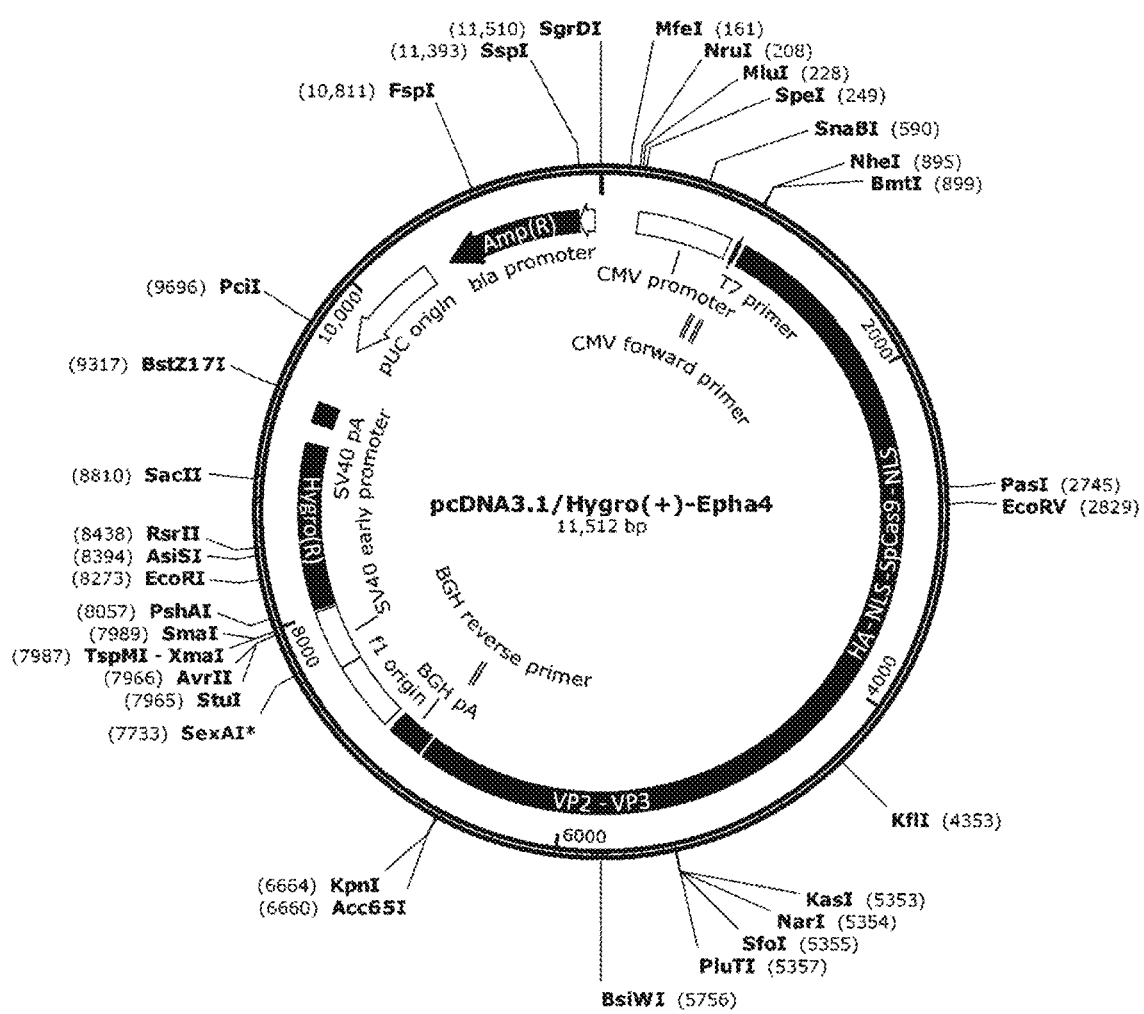
FIG. 4 shows an expression construct comprising a nucleic acid sequence encoding SpCas9 nuclease N-terminally fused to VP2 capsid protein.

FIG. 4 shows one example of an expression construct comprising a nucleic acid sequence encoding SpCas9 nuclease N-terminally fused to VP2 capsid protein.

Example 3

Gene editing platforms, such as the Cas9/sgRNA system, have been shown to induce off-target DNA double-stranded breaks (DSBs) throughout genomes, which is associated with toxicity. Such off-target effects not only stem from ambiguity of DNA sequence recognition by nucleases, but also can be attributed to the prolonged presence of an active gene editing system in a given cell. As a result, off-target DSBs accumulate over time, and ultimately lead to genotoxicity. To mitigate the potential toxicity due to prolonged expression of gene editing system in vivo, transient delivery of endonuclease protein, which induces permanent gene editing followed by natural degradation of the endonuclease, was examined. Specifically, the VP2 protein of AAV capsid was used as a protein delivery vehicle to ferry the Cas9 protein in vivo.

A sensitive gene editing reporter plasmid was constructed. Co-transfection of the reporter plasmid and a plasmid expressing the SpCas9-VP2 fusion protein induced gene editing in HEK293 cells. An rAAV packaging system was modified to include a plasmid expressing VP1 and VP3, and another plasmid expressing either the SpCas9-VP2 fusion protein or the EGFP-VP2 fusion protein. EGFP-AAV2 (EGFP protein grafted on the AAV2 capsid) was successfully produced. However, rAAV particles carrying SpCas9 protein were not produced, likely because the large size of SpCas9 protein interfered with the AAV packaging process.

Figure 5:
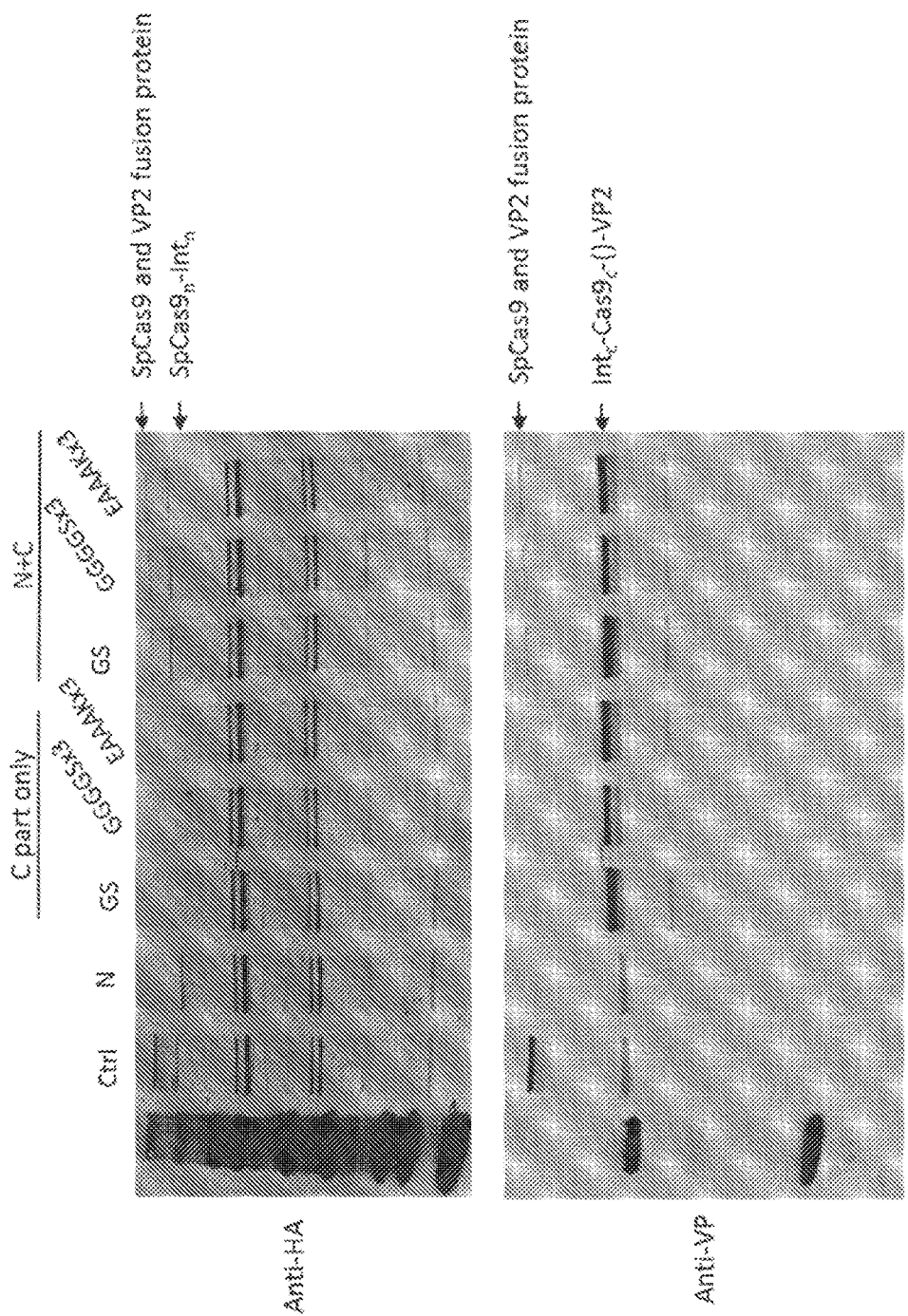
FIG. 5 shows co-transfection of Split Cas9 parts in HEK293 cells reconstituted SpCas9 and VP2 fusion protein, as measured by Western blot. Ctrl: pCMV-SpCas9-(EAAAKx3)-VP2; N: pU1a-Cas9$_n$-Int$_n$; C part: Int$_c$-Cas9$_c$-( )-VP2; HA tag is present in SpCas9 N-terminal. The designation "( )" refers to a linker sequence (e.g., GS, GGGGSx3 (SEQ ID NO: 19), EAAAKx3 (SEQ ID NO: 20)).
Figure 6A:
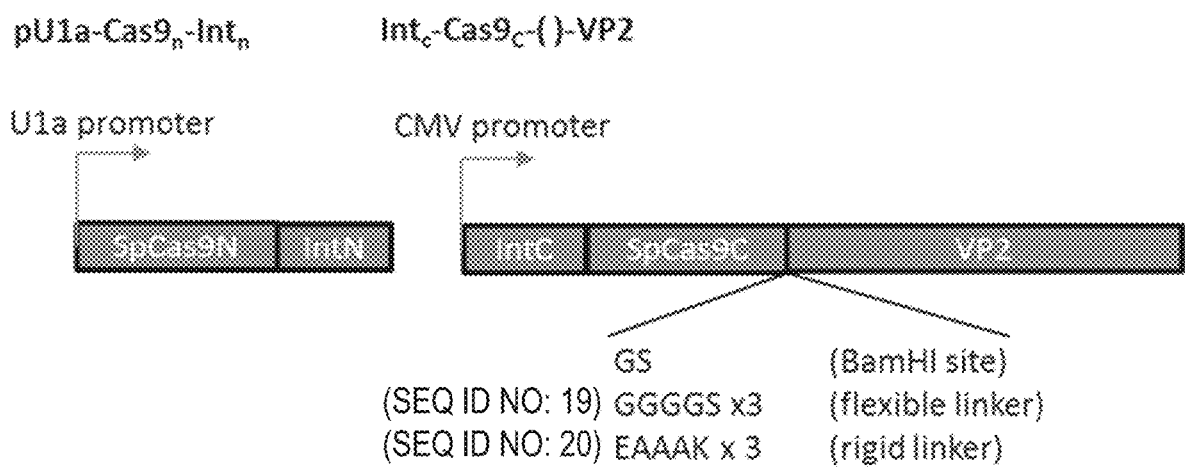
FIGS. 6A-6B show co-transfection of Split Cas9 parts in HEK293 cells reconstituted gene editing function. Cells were transfected with EGFP-ON reporter, pU1a-Cas9$_n$-Int$_n$, and Int$_c$-Cas9$_c$-( )-VP2. EGFP reports Cas9 cleavage and NHEJ repair; mCherry is constitutively expressed as control.
Figure 6B:
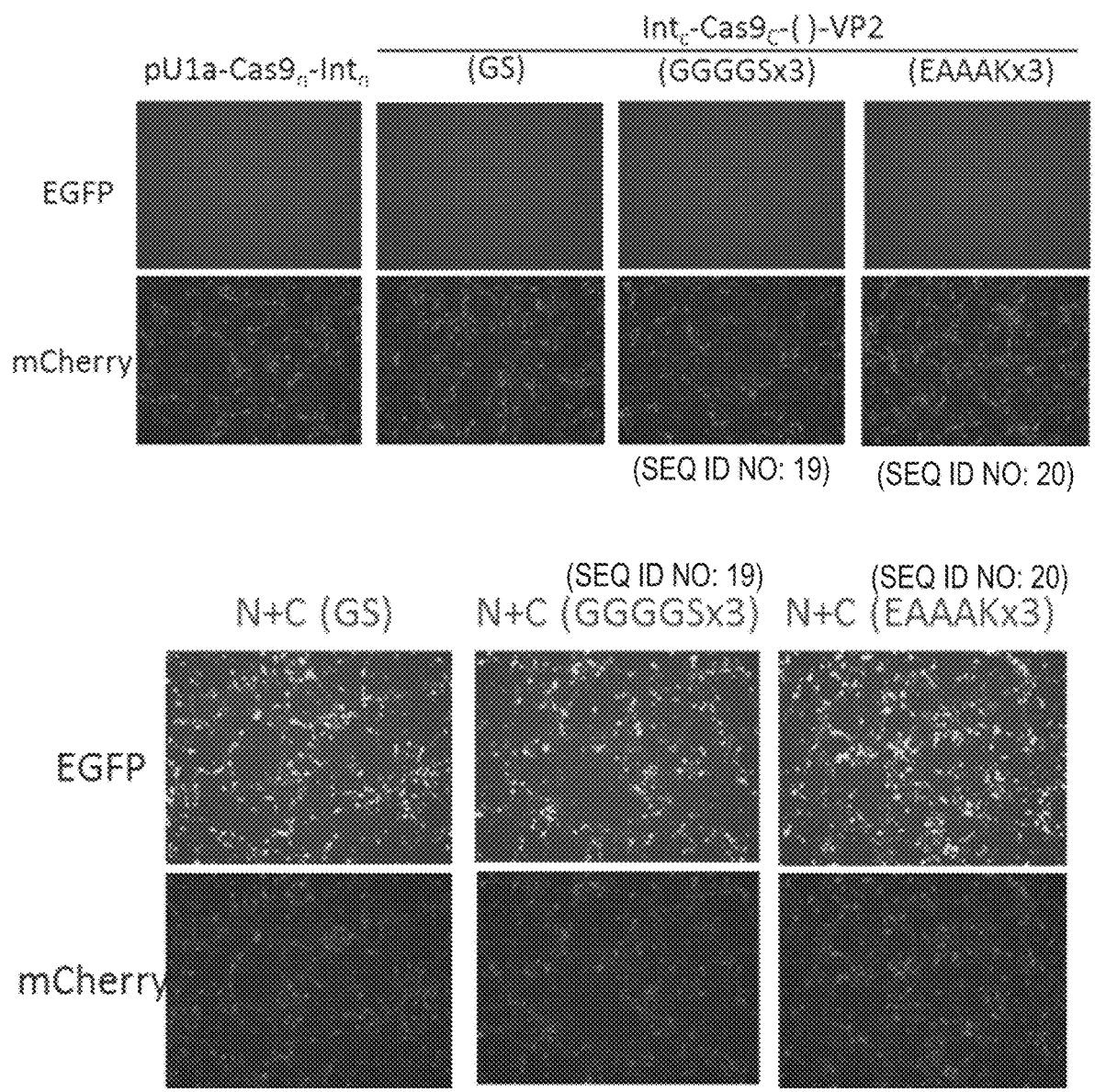

The transgene encoding SpCas9 was split into halves to utilize split intein-mediated protein trans-splicing (PTS) to transiently reconstitute the full-length SpCas9 (FIG. 3A). When the two parts of a split intein (termed $Int_N$ and $Int_C$, respectively) fuse, the split intein mediates PTS, resulting in the generation of a fusion protein with the intein being spliced out. Plasmids expressing the fusion proteins $SpCas9_N$-$Int_N$ and $Int_C$-$SpCas9_C$-VP2 (pU1a-Cas9n-$Int_n$ and $Int_c$-$Cas9_c$-( )-VP2, respectively) were generated. The designation "( )" in the $Int_c$-$Cas9_c$ plasmid represents the presence of a linker sequence (e.g., GS, GGGGSx3 (SEQ ID NO: 19) or EAAAKx3 (SEQ ID NO: 20)). Results show productive intein-mediated reconstitution of SpCas9-VP2 protein in HEK293 cells by co-transfection (FIG. 5). Importantly, co-transfection of plasmids expressing $SpCas9_N$-$Int_N$ and $Int_C$-$SpCas9_C$-VP2 in HEK293 cells led to gene editing based on the EGFP-ON reporter assay, as shown in FIG. 6. EGFP fluorescence reports Cas9 cleavage and NHEJ repair and mCherry is constitutively expressed as a control.

Figure 7:
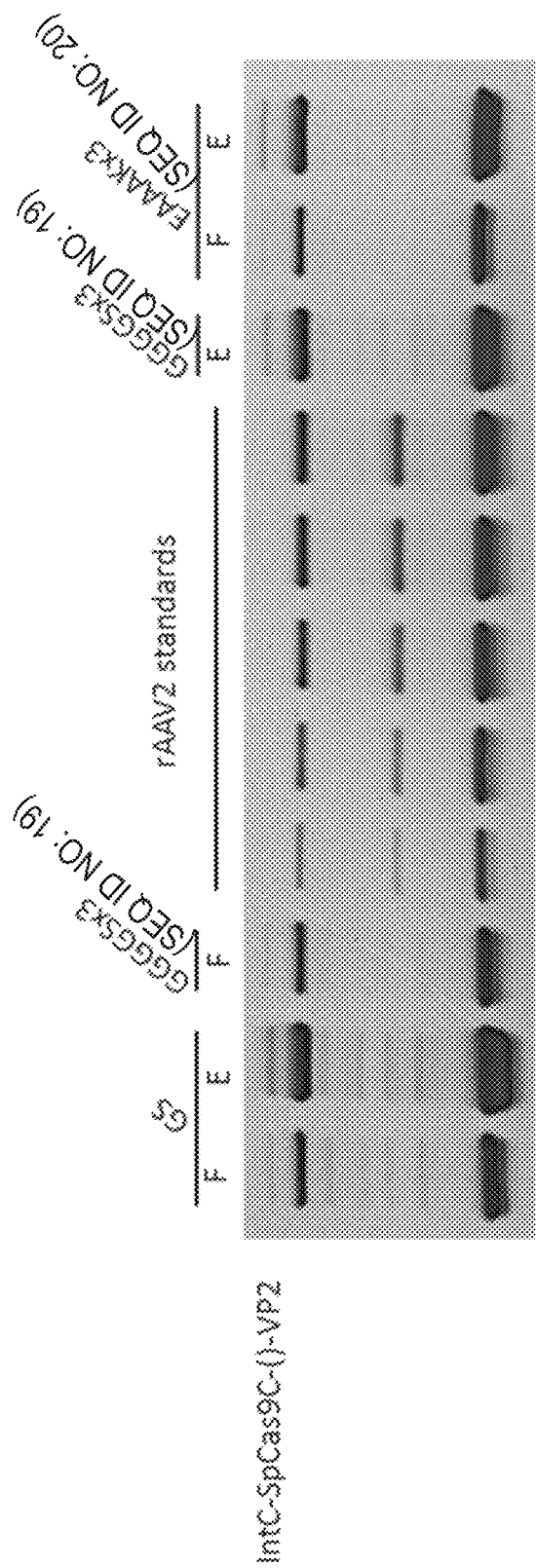
FIG. 7 shows incorporation of Int$_c$-SpCas9$_c$ polypeptide onto rAAV2 capsid. Cells were transfected with plasmid encoding VP1 and VP3 proteins, and a plasmid encoding Int$_c$-SpCas9$_c$-( )-VP2. Purified rAAV particles were examined by silver staining.

The $Int_C$-$SpCas9_C$ protein to be grafted on VP2 is equal or smaller than EGFP. Since EGFP-AAV2 successfully produced, rAAV packaging of the $Int_C$-$SpCas9_C$-VP2 was investigated. Guided by structural analysis, SpCas9 split sites close to the C-terminus of SpCas9 were strategically screened and identified. Cells were transfected with a plasmid encoding VP1 and VP3 proteins, and a second plasmid encoding $Int_c$-$Cas9_c$-( )-VP2. Results indicate successful incorporation of $Int_c$-$SpCas9_c$-VP2 polypeptide onto rAAV2 capsid (FIG. 7).

---

SEQUENCES

```
>SEQ ID NO: 1 SpCas9 nucleic acid sequence
ATGTACCCATACGATGTTCCAGATTACGCTTCGCCGAAGAAAAAGCGCAAGGTC
GAAGCGTCCGACAAGAAGTACAGCATCGGCCTGGACATCGGCACCAACTCTGTG
GGCTGGGCCGTGATCACCGACGAGTACAAGGTGCCCAGCAAGAAATTCAAGGTG
CTGGGCAACACCGACCGGCACAGCATCAAGAAGAACCTGATCGGAGCCCTGCTG
TTCGACAGCGGCGAAACAGCCGAGGCCACCCGGCTGAAGAGAACCGCCAGAAG
AAGATACACCAGACGGAAGAACCGGATCTGCTATCTGCAAGAGATCTTCAGCAA
CGAGATGGCCAAGGTGGACGACAGCTTCTTCCACAGACTGGAAGAGTCCTTCCT
GGTGGAAGAGGATAAGAAGCACGAGCGGCACCCCATCTTCGGCAACATCGTGGA
CGAGGTGGCCTACCACGAGAAGTACCCCACCATCTACCACCTGAGAAAGAAACT
GGTGGACAGCACCGACAAGGCCGACCTGCGGCTGATCTATCTGGCCCTGGCCCA
CATGATCAAGTTCCGGGGCCACTTCCTGATCGAGGGCGACCTGAACCCCGACAA
CAGCGACGTGGACAAGCTGTTCATCCAGCTGGTGCAGACCTACAACCAGCTGTTC
GAGGAAAACCCCATCAACGCCAGCGGCGTGGACGCCAAGGCCATCCTGTCTGCC
AGACTGAGCAAGAGCAGACGGCTGGAAAATCTGATCGCCCAGCTGCCCGGCGAG
AAGAAGAATGGCCTGTTCGGCAACCTGATTGCCCTGAGCCTGGGCCTGACCCCCA
ACTTCAAGAGCAACTTCGACCTGGCCGAGGATGCCAAACTGCAGCTGAGCAAGG
ACACCTACGACGACGACCTGGACAACCTGCTGGCCCAGATCGGCGACCAGTACG
CCGACCTGTTTCTGGCCGCCAAGAACCTGTCCGACGCCATCCTGCTGAGCGACAT
CCTGAGAGTGAACACCGAGATCACCAAGGCCCCCCTGAGCGCCTCTATGATCAA
GAGATACGACGAGCACCACCAGGACCTGACCCTGCTGAAAGCTCTCGTGCGGCA
GCAGCTGCCTGAGAAGTACAAAGAGATTTTCTTCGACCAGAGCAAGAACGGCTA
CGCCGGCTACATTGACGGCGGAGCCAGCCAGGAAGAGTTCTACAAGTTCATCAA
GCCCATCCTGGAAAAGATGGACGGCACCGAGGAACTGCTCGTGAAGCTGAACAG
AGAGGACCTGCTGCGGAAGCAGCGGACCTTCGACAACGGCAGCATCCCCCACCA
GATCCACCTGGGAGAGCTGCACGCCATTCTGCGGCGGCAGGAAGATTTTTACCCA
TTCCTGAAGGACAACCGGGAAAAGATCGAGAAGATCCTGACCTTCCGCATCCCC
```

```
TACTACGTGGGCCCTCTGGCCAGGGGAAACAGCAGATTCGCCTGGATGACCAGA
AAGAGCGAGGAAACCATCACCCCCTGGAACTTCGAGGAAGTGGTGGACAAGGGC
GCTTCCGCCCAGAGCTTCATCGAGCGGATGACCAACTTCGATAAGAACCTGCCA
ACGAGAAGGTGCTGCCCAAGCACAGCCTGCTGTACGAGTACTTCACCGTGTATA
ACGAGCTGACCAAAGTGAAATACGTGACCGAGGGAATGAGAAAGCCCGCCTTCC
TGAGCGGCGAGCAGAAAAAGGCCATCGTGGACCTGCTGTTCAAGACCAACCGGA
AAGTGACCGTGAAGCAGCTGAAAGAGGACTACTTCAAGAAAATCGAGTGCTTCG
ACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAAA
CGAGGACATTCTGGAAGATATCGTGCTGACCCTGACACTGTTTGAGGACAGAGA
GATGATCGAGGAACGGCTGAAAACCTATGCCCACCTGTTCGACGACAAAGTGAT
GAAGCAGCTGAAGCGGCGGAGATACACCGGCTGGGGCAGGCTGAGCCGGAAGC
TGATCAACGGCATCCGGGACAAGCAGTCCGGCAAGACAATCCTGGATTTCCTGA
AGTCCGACGGCTTCGCCAACAGAAACTTCATGCAGCTGATCCACGACGACAGCC
TGACCTTTAAAGAGGACATCCAGAAAGCCCAGGTGTCCGGCCAGGGCGATAGCC
TGCACGAGCACATTGCCAATCTGGCCGGCAGCCCCGCCATTAAGAAGGGCATCC
TGCAGACAGTGAAGGTGGTGGACGAGCTCGTGAAAGTGATGGGCCGGCACAAGC
CCGAGAACATCGTGATCGAAATGGCCAGAGAGAACCAGACCACCCAGAAGGGA
CAGAAGAACAGCCGCGAGAGAATGAAGCGGATCGAAGAGGGCATCAAAGAGCT
GGGCAGCCAGATCCTGAAAGAACACCCCGTGGAAAACACCCAGCTGCAGAACGA
GAAGCTGTACCTGTACTACCTGCAGAATGGGCGGGATATGTACGTGGACCAGGA
ACTGGACATCAACCGGCTGTCCGACTACGATGTGGACCATATCGTGCCTCAGAGC
TTTCTGAAGGACGACTCCATCGACAACAAGGTGCTGACCAGAAGCGACAAGAAC
CGGGGCAAGAGCGACAACGTGCCCTCCGAAGAGGTCGTGAAGAAGATGAAGAA
CTACTGGCGGCAGCTGCTGAACGCCAAGCTGATTACCCAGAGAAAGTTCGACAA
TCTGACCAAGGCCGAGAGAGGCGGCCTGAGCGAACTGGATAAGGCCGGCTTCAT
CAAGAGACAGCTGGTGGAAACCCGGCAGATCACAAAGCACGTGGCACAGATCCT
GGACTCCCGGATGAACACTAAGTACGACGAGAATGACAAGCTGATCCGGGAAGT
GAAAGTGATCACCCTGAAGTCCAAGCTGGTGTCCGATTTCCGGAAGGATTTCCAG
TTTTACAAAGTGCGCGAGATCAACAACTACCACCACGCCCACGACGCCTACCTGA
ACGCCGTCGTGGGAACCGCCCTGATCAAAAAGTACCCTAAGCTGGAAAGCGAGT
TCGTGTACGGCGACTACAAGGTGTACGACGTGCGGAAGATGATCGCCAAGAGCG
AGCAGGAAATCGGCAAGGCTACCGCCAAGTACTTCTTCTACAGCAACATCATGA
ACTTTTTCAAGACCGAGATTACCCTGGCCAACGGCGAGATCCGGAAGCGGCCTCT
GATCGAGACAAACGGCGAAACCGGGGAGATCGTGTGGGATAAGGGCCGGGATTT
TGCCACCGTGCGGAAAGTGCTGAGCATGCCCCAAGTGAATATCGTGAAAAAGAC
CGAGGTGCAGACAGGCGGCTTCAGCAAAGAGTCTATCCTGCCCAAGAGGAACAG
CGATAAGCTGATCGCCAGAAAGAAGGACTGGGACCCTAAGAAGTACGGCGGCTT
CGACAGCCCCACCGTGGCCTATTCTGTGCTGGTGGTGGCCAAAGTGGAAAAGGG
CAAGTCCAAGAAACTGAAGAGTGTGAAAGAGCTGCTGGGGATCACCATCATGGA
AAGAAGCAGCTTCGAGAAGAATCCCATCGACTTTCTGGAAGCCAAGGGCTACAA
AGAAGTGAAAAAGGACCTGATCATCAAGCTGCCTAAGTACTCCCTGTTCGAGCT
GGAAAACGGCCGGAAGAGAATGCTGGCCTCTGCCGGCGAACTGCAGAAGGGAA
ACGAACTGGCCCTGCCCTCCAAATATGTGAACTTCCTGTACCTGGCCAGCCACTA
TGAGAAGCTGAAGGGCTTCCCCCGAGGATAATGAGCAGAAACAGCTGTTTGTGGA
ACAGCACAAGCACTACCTGGACGAGATCATCGAGCAGATCAGCGAGTTCTCCAA
GAGAGTGATCCTGGCCGACGCTAATCTGGACAAAGTGCTGTCCGCCTACAACAA
GCACCGGGATAAGCCCATCAGAGAGCAGGCCGAGAATATCATCCACCTGTTTAC
CCTGACCAATCTGGGAGCCCCTGCCGCCTTCAAGTACTTTGACACCACCATCGAC
CGGAAGAGGTACACCAGCACCAAAGAGGTGCTGGACGCCACCCTGATCCACCAG
AGCATCACCGGCCTGTACGAGACACGGATCGACCTGTCTCAGCTGGGAGGCGAC
AGCCCCAAGAAGAAGAGAAAGGTGGAGGCCAGC
```

>SEQ ID NO: 2 SpCas9 amino acid sequence
MYPYDVPDYASPKKKRKVEASDKKYSIGLDIGTNSVGWAVITDEYKVPSKKFKVLG
NTDRHSIKKNLIGALLFDSGETAEATRLKRTARRRYTRRKNRICYLQEIFSNEMAKVD
DSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKA
ILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKI
LTFRIPYYVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDI
LEDIVLTLTLFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSLHEHIANLAG
SPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVP
QSFLKDDSIDNKVLTRSDKNRGKSDNVPSEEVVKKMKNYWRQLLNAKLITQRKFDN
LTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDY
KVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDP
KKYGGFDSPTVAYSVLVVAKVEKGKSKKLKSVKELLGITIMERSSFEKNPIDFLEAK
GYKEVKKDLIIKLPKYSLFELENGRKRMLASAGELQKGNELALPSKYVNFLYLASHY EKLKGSPEDNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQSITGLYETRI
DLSQLGGDSPKKKRKVEAS

```
>SEQ ID NO: 3 SpCas9-VP2 fusion nucleic acid
ATGTACCCATACGATGTTCCAGATTACGCTTCGCCGAAGAAAAAGCGCAAGGTC
GAAGCGTCCGACAAGAAGTACAGCATCGGCCTGGACATCGGCACCAACTCTGTG
GGCTGGGCCGTGATCACCGACGAGTACAAGGTGCCCAGCAAGAAATTCAAGGTG
CTGGGCAACACCGACCGGCACAGCATCAAGAAGAACCTGATCGGAGCCCTGCTG
TTCGACAGCGGCGAAACAGCCGAGGCCACCCGGCTGAAGAGAACCGCCAGAAG
AAGATACACCAGACGGAAGAACCGGATCTGCTATCTGCAAGAGATCTTCAGCAA
CGAGATGGCCAAGGTGGACGACAGCTTCTTCCACAGACTGGAAGAGTCCTTCCT
GGTGGAAGAGGATAAGAAGCACGAGCGGCACCCCATCTTCGGCAACATCGTGGA
CGAGGTGGCCTACCACGAGAAGTACCCCACCATCTACCACCTGAGAAAGAAACT
GGTGGACAGCACCGACAAGGCCGACCTGCGGCTGATCTATCTGGCCCTGGCCCA
CATGATCAAGTTCCGGGGCCACTTCCTGATCGAGGGCGACCTGAACCCCGACAA
CAGCGACGTGGACAAGCTGTTCATCCAGCTGGTGCAGACCTACAACCAGCTGTTC
GAGGAAAACCCCATCAACGCCAGCGGCGTGGACGCCAAGGCCATCCTGTCTGCC
AGACTGAGCAAGAGCAGACGGCTGGAAAATCTGATCGCCCAGCTGCCCGGCGAG
AAGAAGAATGGCCTGTTCGGCAACCTGATTGCCCTGAGCCTGGGCCTGACCCCCA
ACTTCAAGAGCAACTTCGACCTGGCCGAGGATGCCAAACTGCAGCTGAGCAAGG
ACACCTACGACGACGACCTGGACAACCTGCTGGCCCAGATCGGCGACCAGTACG
CCGACCTGTTTCTGGCCGCCAAGAACCTGTCCGACGCCATCCTGCTGAGCGACAT
CCTGAGAGTGAACACCGAGATCACCAAGGCCCCCCTGAGCGCCTCTATGATCAA
GAGATACGACGAGCACCACCAGGACCTGACCCTGCTGAAAGCTCTCGTGCGGCA
GCAGCTGCCTGAGAAGTACAAAGAGATTTTCTTCGACCAGAGCAAGAACGGCTA
CGCCGGCTACATTGACGGCGGAGCCAGCCAGGAAGAGTTCTACAAGTTCATCAA
GCCCATCCTGGAAAAGATGGACGGCACCGAGGAACTGCTCGTGAAGCTGAACAG
AGAGGACCTGCTGCGGAAGCAGCGGACCTTCGACAACGGCAGCATCCCCCACCA
GATCCACCTGGGAGAGCTGCACGCCATTCTGCGGCGGCAGGAAGATTTTTACCCA
TTCCTGAAGGACAACCGGGAAAAGATCGAGAAGATCCTGACCTTCCGCATCCCC
TACTACGTGGGCCCTCTGGCCAGGGGAAACAGCAGATTCGCCTGGATGACCAGA
AAGAGCGAGGAAACCATCACCCCCTGGAACTTCGAGGAAGTGGTGGACAAGGGC
GCTTCCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTATA
ACGAGCTGACCAAAGTGAAATACGTGACCGAGGGAATGAGAAAGCCCGCCTTCC
TGAGCGGCGAGCAGAAAAAGGCCATCGTGGACCTGCTGTTCAAGACCAACCGGA
AAGTGACCGTGAAGCAGCTGAAAGAGGACTACTTCAAGAAAATCGAGTGCTTCG
ACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAAA
CGAGGACATTCTGGAAGATATCGTGCTGACCCTGACACTGTTTGAGGACAGAGA
GATGATCGAGGAACGGCTGAAAACCTATGCCCACCTGTTCGACGACAAAGTGAT
GAAGCAGCTGAAGCGGCGGAGATACACCGGCTGGGGCAGGCTGAGCCGGAAGC
TGATCAACGGCATCCGGGACAAGCAGTCCGGCAAGACAATCCTGGATTTCCTGA
AGTCCGACGGCTTCGCCAACAGAAACTTCATGCAGCTGATCCACGACGACAGCC
TGACCTTTAAAGAGGACATCCAGAAAGCCCAGGTGTCCGGCCAGGGCGATAGCC
TGCACGAGCACATTGCCAATCTGGCCGGCAGCCCCGCCATTAAGAAGGGCATCC
TGCAGACAGTGAAGGTGGTGGACGAGCTCGTGAAAGTGATGGGCCGGCACAAGC
CCGAGAACATCGTGATCGAAATGGCCAGAGAGAACCAGACCACCCAGAAGGGA
CAGAAGAACAGCCGCGAGAGAATGAAGCGGATCGAAGAGGGCATCAAAGAGCT
GGGCAGCCAGATCCTGAAAGAACACCCCGTGGAAAACACCCAGCTGCAGAACGA
GAAGCTGTACCTGTACTACCTGCAGAATGGGCGGGATATGTACGTGGACCAGGA
ACTGGACATCAACCGGCTGTCCGACTACGATGTGGACCATATCGTGCCTCAGAGC
TTTCTGAAGGACGACTCCATCGACAACAAGGTGCTGACCAGAAGCGACAAGAAC
CGGGGCAAGAGCGACAACGTGCCCTCCGAAGAGGTCGTGAAGAAGATGAAGAA
CTACTGGCGGCAGCTGCTGAACGCCAAGCTGATTACCCAGAGAAAGTTCGACAA
TCTGACCAAGGCCGAGAGAGGCGGCCTGAGCGAACTGGATAAGGCCGGCTTCAT
CAAGAGACAGCTGGTGGAAACCCGGCAGATCACAAAGCACGTGGCACAGATCCT
GGACTCCCGGATGAACACTAAGTACGACGAGAATGACAAGCTGATCCGGGAAGT
GAAAGTGATCACCCTGAAGTCCAAGCTGGTGTCCGATTTCCGGAAGGATTTCCAG
TTTTACAAAGTGCGCGAGATCAACAACTACCACCACGCCCACGACGCCTACCTGA
ACGCCGTCGTGGGAACCGCCCTGATCAAAAAGTACCCTAAGCTGGAAAGCGAGT
TCGTGTACGGCGACTACAAGGTGTACGACGTGCGGAAGATGATCGCCAAGAGCG
AGCAGGAAATCGGCAAGGCTACCGCCAAGTACTTCTTCTACAGCAACATCATGA
ACTTTTTCAAGACCGAGATTACCCTGGCCAACGGCGAGATCCGGAAGCGGCCTCT
GATCGAGACAAACGGCGAAACCGGGGAGATCGTGTGGGATAAGGGCCGGGATTT
TGCCACCGTGCGGAAAGTGCTGAGCATGCCCCAAGTGAATATCGTGAAAAAGAC
CGAGGTGCAGACAGGCGGCTTCAGCAAAGAGTCTATCCTGCCCAAGAGGAACAG
CGATAAGCTGATCGCCAGAAAGAAGGACTGGGACCCTAAGAAGTACGGCGGCTT
CGACAGCCCCACCGTGGCCTATTCTGTGCTGGTGGTGGCCAAAGTGGAAAAGGG
CAAGTCCAAGAAACTGAAGAGTGTGAAAGAGCTGCTGGGGATCACCATCATGGA
AAGAAGCAGCTTCGAGAAGAATCCCATCGACTTTCTGGAAGCCAAGGGCTACAA
AGAAGTGAAAAAGGACCTGATCATCAAGCTGCCTAAGTACTCCCTGTTCGAGCT
GGAAAACGGCCGGAAGAGAATGCTGGCCTCTGCCGGCGAACTGCAGAAGGGAA
ACGAACTGGCCCTGCCCTCCAAATATGTGAACTTCCTGTACCTGGCCAGCCACTA
TGAGAAGCTGAAGGGCTCCCCCGAGGATAATGAGCAGAAACAGCTGTTTGTGGA
ACAGCACAAGCACTACCTGGACGAGATCATCGAGCAGATCAGCGAGTTCTCCAA
```

| SEQUENCES |
| --- |
| GAGAGTGATCCTGGCCGACGCTAATCTGGACAAAGTGCTGTCCGCCTACAACAA |
| GCACCGGGATAAGCCCATCAGAGAGCAGGCCGAGAATATCATCCACCTGTTTAC |
| CCTGACCAATCTGGGAGCCCCTGCCGCCTTCAAGTACTTTGACACCACCATCGAC |
| CGGAAGAGGTACACCAGCACCAAAGAGGTGCTGGACGCCACCCTGATCCACCAG |
| AGCATCACCGGCCTGTACGAGACACGGATCGACCTGTCTCAGCTGGGAGGCGAC |
| AGCCCCAAGAAGAAGAGAAAGGTGGAGGCCAGCGAATTGGCTCCGGGAAAAAA |
| GAGGCCGGTAGAGCACTCTCCTGTGGAGCCAGACTCCTCCTCGGGAACCGGAAA |
| GGCGGGCCAGCAGCCTGCAAGAAAAAGATTGAATTTTGGTCAGACTGGAGACGC |
| AGACTCAGTACCTGACCCCCAGCCTCTCGGACAGCCACCAGCAGCCCCCTCTGGT |
| CTGGGAACTAATACGATGGCTACAGGCAGTGGCGCACCAATGGCAGACAATAAC |
| GAGGGCGCCGACGGAGTGGGTAATTCCTCGGGAAATTGGCATTGCGATTCCACA |
| TGGATGGGCGACAGAGTCATCACCACCAGCACCCGAACCTGGGCCCTGCCCACC |
| TACAACAACCACCTCTACAAACAAATTTCCAGCCAATCAGGAGCCTCGAACGAC |
| AATCACTACTTTGGCTACAGCACCCCTTGGGGTATTTTGACTTCAACAGATTCC |
| ACTGCCACTTTTCACCACGTGACTGGCAAAGACTCATCAACAACAACTGGGGATT |
| CCGACCCAAGAGACTCAACTTCAAGCTCTTTAACATTCAAGTCAAAGAGGTCACG |
| CAGAATGACGGTACGACGACGATTGCCAATAACCTTACCAGCACGGTTCAGGTG |
| TTTACTGACTCGGAGTACCAGCTCCCGTACGTCCTCGGCTCGGCGCATCAAGGAT |
| GCCTCCCGCCGTTCCCAGCAGACGTCTTCATGGTGCCACAGTATGGATACCTCAC |
| CCTGAACAACGGGAGTCAGGCAGTAGGACGCTCTTCATTTTACTGCCTGGAGTAC |
| TTTCCTTCTCAGATGCTGCGTACCGGAAACAACTTTACCTTCAGCTACACTTTTGA |
| GGACGTTCCTTTCCACAGCAGCTACGCTCACAGCCAGAGTCTGGACCGTCTCATG |
| AATCCTCTCATCGACCAGTACCTGTATTACTTGAGCAGAACAAACACTCCAAGTG |
| GAACCACCACGCAGTCAAGGCTTCAGTTTTCTCAGGCCGGAGCGAGTGACATTCG |
| GGACCAGTCTAGGAACTGGCTTCCTGGACCCTGTTACCGCCAGCAGCGAGTATCA |
| AAGACATCTGCGGATAACAACAACAGTGAATACTCGTGGACTGGAGCTACCAAG |
| TACCACCTCAATGGCAGAGACTCTCTGGTGAATCCGGGCCCGGCCATGGCAAGC |
| CACAAGGACGATGAAGAAAAGTTTTTTCCTCAGAGCGGGGTTCTCATCTTTGGGA |
| AGCAAGGCTCAGAGAAAACAAATGTGGACATTGAAAAGGTCATGATTACAGACG |
| AAGAGGAAATCAGGACAACCAATCCCGTGGCTACGGAGCAGTATGGTTCTGTAT |
| CTACCAACCTCCAGAGAGGCAACAGACAAGCAGCTACCGCAGATGTCAACACAC |
| AAGGCGTTCTTCCAGGCATGGTCTGGCAGGACAGAGATGTGTACCTTCAGGGGC |
| CCATCTGGGCAAAGATTCCACACACGGACGGACATTTTCACCCCTCTCCCCTCAT |
| GGGTGGATTCGGACTTAAACACCCTCCTCCACAGATTCTCATCAAGAACACCCCG |
| GTACCTGCGAATCCTTCGACCACCTTCAGTGCGGCAAAGTTTGCTTCCTTCATCAC |
| ACAGTACTCCACGGACAGGTCAGCGTGGAGATCGAGTGGGAGCTGCAGAAGGA |
| AAACAGCAAACGCTGGAATCCCGAAATTCAGTACACTTCCAACTACAACAAGTC |
| TGTTAATGTGGACTTTACTGTGGACACTAATGGCGTGTATTCAGAGCCTCGCCCC |
| ATTGGCACCAGATACCTGACTCGTAATCTGTAA |

>SEQ ID NO: 4 SpCas9-VP2 fusion protein
MYPYDVPDYASPKKKRKVEASDKKYSIGLDIGTNSVGWAVITDEYKVPSKKFKVLG
NTDRHSIKKNLIGALLFDSGETAEATRLKRTARRRYTRRKNRICYLQEIFSNEMAKVD
DSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKA
ILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKI
LTFRIPYYVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDI
LEDIVLTLTLFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSLHEHIANLAG
SPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVP
QSFLKDDSIDNKVLTRSDKNRGKSDNVPSEEVVKKMKNYWRQLLNAKLITQRKFDN
LTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDY
KVYDVRKMIAKSEQEIGKATAKYFFYSNIMNFFKTEITLANGEIRKRPLIETNGETEI
VWDKGRDFATVRKVLSMPQVNIVKKTEVQTGGFSKESILPKRNSDKLIARKKDWDP
KKYGGFDSPTVAYSVLVVAKVEKGKSKKLKSVKELLGITIMERSSFEKNPIDFLEAK
GYKEVKKDLIIKLPKYSLFELENGRKRMLASAGELQKGNELALPSKYVNFLYLASHY
EKLKGSPEDNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQSITGLYETRI
DLSQLGGDSPKKKRKVEASELAPGKKRPVEHSPVEPDSSSGTGKAGQQPARKRLNFG
QTGDADSVPDPQPLGQPPAAPSGLGTNTMATGSGAPMADNNEGADGVGNSSGNWH
CDSTWMGDRVITTSTRTWALPTYNNHLYKQISSQSGASNDNHYFGYSTPWGYFDFN
RFHCHFSPRDWQRLINNNWGFRPKRLNFKLFNIQVKEVTQNDGTTTIANNLTSTVQV
FTDSEYQLPYVLGSAHQGCLPPFPADVFMVPQYGYLTLNNGSQAVGRSSFYCLEYFP
SQMLRTGNNFTFSYTFEDVPFHSSYAHSQSLDRLMNPLIDQYLYYLSRTNTPSGTTTQ
SRLQFSQAGASDIRDQSRNWLPGPCYRQQRVSKTSADNNNSEYSWTGATKYHLNGR
DSLVNPGPAMASHKDDEEKFFPQSGVLIFGKQGSEKTNVDIEKVMITDEEEIRTTNPV
ATEQYGSVSTNLQRGNRQAATADVNTQGVLPGMVWQDRDVYLQGPIWAKIPHTDG
HFHPSPLMGGFGLKHPPPQILIKNTPVPANPSTTFSAAKFASFITQYSTGQVSVEIEWE
LQKENSKRWNPEIQYTSNYNKSVNVDFTVDTNGVYSEPRPIGTRYLTRNL -continued

SEQUENCES

>SEQ ID NO: 5 Linker sequence
GGGS

>SEQ ID NO: 6 Cas9$_n$-Int$_n$
MYPYDVPDYASPKKKRKVEASDKKYSIGLDIGTNSVGWAVITDEYKVPSKKFKVLG
NTDRHSIKKNLIGALLFDSGETAEATRLKRTARRRYTRRKNRICYLQEIFSNEMAKVD
DSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKA
ILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKI
LTFRIPYYVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDI
LEDIVLTLTLFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSLHEHIANLAG
SPAIKKGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDVDHIVP
QSFLKDDSIDNKVLTRSDKNRGKSDNVPSEEVVKKMKNYWRQLLNAKLITQRKFDN
LTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDY
KVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDP
KKYGGFDSPTVAYSVLVVAKVEKGKSKKLKSVKELLGITIMERSSFEKNPIDFLEAK
GYKEVKKDLIIKLPKYSLFELENGRKCLSYETEILTVEYGLLPIGKIVEKRIECTVYSV
DNNGNIYTQPVAQWHDRGEQEVFEYCLEDGSLIRATKDHKFMTVDGQMLPIDEIFER
ELDLMRVDNLPN

>SEQ ID NO: 7 Int$_c$-Cas9$_c$-GS-VP2
MIKIATRKYLGKQNVYDIGVERDHNFALKNGFIASNCMLASAGELQKGNELALPSK
YVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLI
HQSITGLYETRIDLSQLGGDSPKKKRKVEASGSAPGKKRPVEHSPVEPDSSSGTGKAG
QQPARKRLNFGQTGDADSVPDPQPLGQPPAAPSGLGTNTMATGSGAPMADNNEGA
DGVGNSSGNWHCDSTWMGDRVITTSTRTWALPTYNNHLYKQISSQSGASNDNHYF
GYSTPWGYFDFNRFHCHFSPRDWQRLINNNWGFRPKRLNFKLFNIQVKEVTQNDGT
TTIANNLTSTVQVFTDSEYQLPYVLGSAHQGCLPPFPADVFMVPQYGYLTLNNGSQA
VGRSSFYCLEYFPSQMLRTGNNFTFSYTFEDVPFHSSYAHSQSLDRLMNPLIDQYLYY
LSRTNTPSGTTTQSRLQFSQAGASDIRDQSRNWLPGPCYRQQRVSKTSADNNNSEYS
WTGATKYHLNGRDSLVNPGPAMASHKDDEEKFFPQSGVLIFGKQGSEKTNVDIEKV
MITDEEEIRTTNPVATEQYGSVSTNLQRGNRQAATADVNTQGVLPGMVWQDRDVY
LQGPIWAKIPHTDGHFHPSPLMGGFGLKHPPPQILIKNTPVPANPSTTFSAAKFASFITQ
YSTGQVSVEIEWELQKENSKRWNPEIQYTSNYNKSVNVDFTVDTNGVYSEPRPIGTR
YLTRNL

>SEQ ID NO: 8 Int$_c$-Cas9$_c$-GGGGSGGGGSGGGGS-VP2
MIKIATRKYLGKQNVYDIGVERDHNFALKNGFIASNCMLASAGELQKGNELALPSK
YVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLI
HQSITGLYETRIDLSQLGGDSPKKKRKVEASGGGGSGGGGSGGGGSAPGKKRPVEHS
PVEPDSSSGTGKAGQQPARKRLNFGQTGDADSVPDPQPLGQPPAAPSGLGTNTMAT
GSGAPMADNNEGADGVGNSSGNWHCDSTWMGDRVITTSTRTWALPTYNNHLYKQI
SSQSGASNDNHYFGYSTPWGYFDFNRFHCHFSPRDWQRLINNNWGFRPKRLNFKLF
NIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFTFSYTFEDVPFHSSYAHSQSL
DRLMNPLIDQYLYYLSRTNTPSGTTTQSRLQFSQAGASDIRDQSRNWLPGPCYRQQR
VSKTSADNNNSEYSWTGATKYHLNGRDSLVNPGPAMASHKDDEEKFFPQSGVLIFG
KQGSEKTNVDIEKVMITDEEEIRTTNPVATEQYGSVSTNLQRGNRQAATADVNTQG
VLPGMVWQDRDVYLQGPIWAKIPHTDGHFHPSPLMGGFGLKHPPPQILIKNTPVPAN
PSTTFSAAKFASFITQYSTGQVSVEIEWELQKENSKRWNPEIQYTSNYNKSVNVDFTV
DTNGVYSEPRPIGTRYLTRNL

>SEQ ID NO: 9 Int$_c$-Cas9$_c$-EAAAKEAAAKEAAAK-VP2
MIKIATRKYLGKQNVYDIGVERDHNFALKNGFIASNCMLASAGELQKGNELALPSK
YVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLI
HQSITGLYETRIDLSQLGGDSPKKKRKVEASEAAAKEAAAKEAAAKAPGKKRPVEH
SPVEPDSSSGTGKAGQQPARKRLNFGQTGDADSVPDPQPLGQPPAAPSGLGTNTMAT
GSGAPMADNNEGADGVGNSSGNWHCDSTWMGDRVITTSTRTWALPTYNNHLYKQI
SSQSGASNDNHYFGYSTPWGYFDFNRFHCHFSPRDWQRLINNNWGFRPKRLNFKLF
NIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFTFSYTFEDVPFHSSYAHSQSL
DRLMNPLIDQYLYYLSRTNTPSGTTTQSRLQFSQAGASDIRDQSRNWLPGPCYRQQR
VSKTSADNNNSEYSWTGATKYHLNGRDSLVNPGPAMASHKDDEEKFFPQSGVLIFG
KQGSEKTNVDIEKVMITDEEEIRTTNPVATEQYGSVSTNLQRGNRQAATADVNTQG
VLPGMVWQDRDVYLQGPIWAKIPHTDGHFHPSPLMGGFGLKHPPPQILIKNTPVPAN

PSTTFSAAKFASFITQYSTGQVSVEIEWELQKENSKRWNPEIQYTSNYNKSVNVDFTV
DTNGVYSEPRPIGTRYLTRNL

>SEQ ID NO: 10 pU1a-Cas9$_n$-Int$_n$
CCTGCAGGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAG
AGGGAGTGGCCAACTCCATCACTAGGGGTTCCTGCGGCCTCTAGAATGGAGGCG
GTACTATGTAGATGAGAATTCAGGAGCAAACTGGGAAAAGCAACTGCTTCCAAA
TATTTGTGATTTTTACAGTGTAGTTTTGGAAAAACTCTTAGCCTACCAATTCTTCT
AAGTGTTTTAAAATGTGGGAGCCAGTACACATGAAGTTATAGAGTGTTTTAATGA
GGCTTAAATATTTACCGTAACTATGAAATGCTACGCATATCATGCTGTTCAGGCT
CCGTGGCCACGCAACTCATACTACCGGTGCCACCATGTACCCATACGATGTTCCA
GATTACGCTTCGCCGAAGAAAAGCGCAAGGTCGAAGCGTCCGACAAGAAGTAC
AGCATCGGCCTGGACATCGGCACCAACTCTGTGGGCTGGGCCGTGATCACCGAC
GAGTACAAGGTGCCCAGCAAGAAATTCAAGGTGCTGGGCAACACCGACCGGCAC
AGCATCAAGAAGAACCTGATCGGAGCCCTGCTGTTCGACAGCGGCGAAACAGCC
GAGGCCACCCGGCTGAAGAGAACCGCCAGAAGAAGATACACCAGACGGAAGAA
CCGGATCTGCTATCTGCAAGAGATCTTCAGCAACGAGATGGCCAAGGTGGACGA
CAGCTTCTTCCACAGACTGGAAGAGTCCTTCCTGGTGGAAGAGGATAAGAAGCA
CGAGCGGCACCCCATCTTCGGCAACATCGTGGACGAGGTGGCCTACCACGAGAA
GTACCCCACCATCTACCACCTGAGAAAGAAACTGGTGGACAGCACCGACAAGGC
CGACCTGCGGCTGATCTATCTGGCCCTGGCCCACATGATCAAGTTCCGGGGCCAC
TTCCTGATCGAGGGCGACCTGAACCCCGACAACAGCGACGTGGACAAGCTGTTC
ATCCAGCTGGTGCAGACCTACAACCAGCTGTTCGAGGAAAACCCCATCAACGCC
AGCGGCGTGGACGCCAAGGCCATCCTGTCTGCCAGACTGAGCAAGAGCAGACGG
CTGGAAAATCTGATCGCCCAGCTGCCCGGCGAGAAGAAGAATGGCCTGTTCGGC
AACCTGATTGCCCTGAGCCTGGGCCTGACCCCCAACTTCAAGAGCAACTTCGACC
TGGCCGAGGATGCCAAACTGCAGCTGAGCAAGGACACCTACGACGAGCTGGACCTGG
ACAACCTGCTGGCCCAGATCGGCGACCAGTACGCCGACCTGTTTCTGGCCGCCAA
GAACCTGTCCGACGCCATCCTGCTGAGCGACATCCTGAGAGTGAACACCGAGAT
CACCAAGGCCCCCCTGAGCGCCTCTATGATCAAGAGATACGACGAGCACCACCA
GGACCTGACCCTGCTGAAAGCTCTCGTGCGGCAGCAGCTGCCTGAGAAGTACAA
AGAGATTTTCTTCGACCAGAGCAAGAACGGCTACGCCGGCTACATTGACGGCGG
AGCCAGCCAGGAAGAGTTCTACAAGTTCATCAAGCCCATCCTGGAAAAGATGGA
CGGCACCGAGGAACTGCTCGTGAAGCTGAACAGAGAGGACCTGCTGCGGAAGCA
GCGGACCTTCGACAACGGCAGCATCCCCCACCAGATCCACCTGGGAGAGCTGCA
CGCCATTCTGCGGCGGCAGGAAGATTTTTACCCATTCCTGAAGGACAACCGGGA
AAAGATCGAAAAGATCCTGACCTTCCGCATCCCCTACTACGTGGGCCCTCTGGCC
AGGGGAAACAGCAGATTCGCCTGGATGACCAGAAAGAGCGAGGAAACCATCAC
CCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAA
GCACAGCCTGCTGTACGAGTACTTCACCGTGTATAACGAGCTGACCAAAGTGAA
ATACGTGACCGAGGGAATGAGAAAGCCCGCCTTCCTGAGCGGCGAGCAGAAAAA
GGCCATCGTGGACCTGCTGTTCAAGACCAACCGGAAAGTGACCGTGAAGCAGCT
GAAAGAGGACTACTTCAAGAAAATCGAGTGCTTCGACTCCGTGGAAATCTCCGG
CGTGGAAGATCGGTTCAACGCCTCCCTGGGCACATACCACGATCTGCTGAAAATT
ATCAAGGACAAGGACTTCCTGGACAATGAGGAAAACGAGGACATTCTGGAAGAT
ATCGTGCTGACCCTGACACTGTTTGAGGACAGAGAGATGATCGAGGAACGGCTG
AAAACCTATGCCCACCTGTTCGACGACAAAGTGATGAAGCAGCTGAAGCGGCGG
AGATACACCGGCTGGGGCAGGCTGAGCCGGAAGCTGATCAACGGCATCCGGGAC
AAGCAGTCCGGCAAGACAATCCTGGATTTCCTGAAGTCCGACGGCTTCGCCAAC
AGAAACTTCATGCAGCTGATCCACGACGACAGCCTGACCTTTAAAGAGGACATC
CAGAAAGCCCAGGTGTCCGGCCAGGGCGATAGCCTGCACGAGCACATTGCCAAT
CTGGCCGGCAGCCCCGCCATTAAGAAGGGCATCCTGCAGACAGTGAAGGTGGTG
GACGAGCTCGTGAAAGTGATGGGCCGGCACAAGCCCGAGAACATCGTGATCGAA
ATGGCCAGAGAGAACCAGACCACCCAGAAGGGACAGAAGAACAGCCGCGAGAG
AATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACC
TGCAGAATGGGCGGGATATGTACGTGGACCAGGAACTGGACATCAACCGGCTGT
CCGACTACGATGTGGACCATATCGTGCCTCAGAGCTTTCTGAAGGACGACTCCAT
CGACAACAAGGTGCTGACCAGAAGCGACAAGAACCGGGGCAAGAGCGACAACG
TGCCCTCCGAAGAGGTCGTGAAGAAGATGAAGAACTACTGGCGGCAGCTGCTGA
ACGCCAAGCTGATTACCCAGAGAAAGTTCGACAATCTGACCAAGGCCGAGAGAG
GCGGCCTGAGCGAACTGGATAAGGCCGGCTTCATCAAGAGACAGCTGGTGGAAA
CCCGGCAGATCACAAAGCACGTGGCACAGATCCTGGACTCCCGGATGAACACTA
AGTACGACGAGAATGACAAGCTGATCCGGGAAGTGAAAGTGATCACCCTGAAGT
CCAAGCTGGTGTCCGATTTCCGGAAGGATTTCCAGTTTTACAAAGTGCGCGAGAT
CAACAACTACCACCACGCCCACGACGCCTACCTGAACGCCGTCGTGGGAACCGC
CCTGATCAAAAAGTACCCTAAGCTGGAAAGCGAGTTCGTGTACGGCGACTACAA
GGTGTACGACGTGCGGAAGATGATCGCCAAGAGCGAGCAGGAAATCGGCAAGG
CTACCGCCAAGTACTTCTTCTACAGCAACATCATGAACTTTTTCAAGACCGAGAT
TACCCTGGCCAACGGCGAGATCCGGAAGCGGCCTCTGATCGAGACAAACGGCGA
AACCGGGGAGATCGTGTGGGATAAGGGCCGGGATTTTGCCACCGTGCGGAAAGT
GCTGAGCATGCCCCAAGTGAATATCGTGAAAAAGACCGAGGTGCAGACAGGCGG
CTTCAGCAAAGAGTCTATCCTGCCCAAGAGGAACAGCGATAAGCTGATCGCCAG
AAAGAAGGACTGGGACCCTAAGAAGTACGGCGGCTTCGACAGCCCCACCGTGGC
CTATTCTGTGCTGGTGGTGGCCAAAGTGGAAAAGGGCAAGTCCAAGAAACTGAA

GAGTGTGAAAGAGCTGCTGGGGATCACCATCATGGAAAGAAGCAGCTTCGAGAA
GAATCCCATCGACTTTCTGGAAGCCAAGGGCTACAAAGAAGTGAAAAAGGACCT
GATCATCAAGCTGCCTAAGTACTCCCTGTTCGAGCTGGAAAACGGCCGGAAGTGT
CTGTCGTATGAGACCGAGATCCTGACCGTGGAGTATGGACTGCTGCCGATTGGAA
AGATTGTGGAGAAGCGCATTGAGTGCACCGTGTACAGCGTGGATAACAATGGCA
ACATCTATACACAGCCAGTGGCCCAGTGGCACGACCGCGGAGAGCAGGAGGTCT
TCGAGTACTGCCTGGAGGATGGCAGCCTGATTCGCGCCACCAAGGATCATAAGTT
CATGACGGTGGACGGACAGATGCTGCCCATCGATGAGATTTTTGAGCGCGAGCT
GGATCTGATGCGCGTGGATAACCTGCCGAATTAAGAATTCGATCTTTTTCCCTCT
GCCAAAAATTATGGGGACATCATGAAGCCCCTTGAGCATCTGACTTCTGGCTAAT
AAAGGAAATTTATTTTCATTGCAATAGTGTGTTGGAATTTTTTGTGTCTCTCACTC
GGCGGCCGCAGGAACCCCTAGTGATGGAGTTGGCCACTCCCTCTCTGCGCGCTCG
CTCGCTCACTGAGGCCGGGCGACCAAAGGTCGCCCGACGCCCGGGCTTTGCCCG
GGCGGCCTCAGTGAGCGAGCGAGCGCGCAGCTGCCTGCAGG

>SEQ ID NO: 11 Int$_c$-Cas9$_c$-GS-VP2
GTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCAT
AGTAACGCCAATAGGGACTTTCCATTGACGTCAATGGGTGGATATTTACGGTAA
ACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATG
GGACTTTCCTACTTGGCAGTACATCTACGTATTAGTCATCGCTATTACCATGGTGA
TGCGGTTTTGGCAGTACATCAATGGGCGTGGATAGCGGTTTGACTCACGGGGATT
TCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTA
GGCGTGTACGGTGGGAGGTCTATATAAGCAGAGCTCTCTGGCTAACTAGAGAAC
CCACTGCTTACTGGCTTATCGAAATTAATACGACTCACTATAGGGAGACCCAAGC
TGGCTAGCGCCACCATGATCAAGATTGCCACGCGCAAGTACCTGGGCAAGCAGA
ACGTGTACGACATCGGAGTGGAGCGCGATCACAACTTTGCCCTGAAGAATGGCT
TTATTGCCTCGAACTGTATGCTGGCCTCTGCCGGCGAACTGCAGAAGGGAAACGA
ACTGGCCCTGCCCTCCAAATATGTGAACTTCCTGTACCTGGCCAGCCACTATGAG
AAGCTGAAGGGCTCCCCCGAGGATAATGAGCAGAAACAGCTGTTTGTGGAACAG
CACAAGCACTACCTGGACGAGATCATCGAGCAGATCAGCGAGTTCTCCAAGAGA
GTGATCCTGGCCGACGCTAATCTGGACAAAGTGCTGTCCGCCTACAACAAGCACC
GGGATAAGCCCATCAGAGAGCAGGCCGAGAATATCATCCACCTGTTTACCCTGA
CCAATCTGGGAGCCCCTGCCGCCTTCAAGTACTTTGACACCACCATCGACCGGAA
GAGGTACACCAGCACCAAAGAGGTGCTGGACGCCACCCTGATCCACCAGAGCAT
CACCGGCCTGTACGAGACACGGATCGACCTGTCTCAGCTGGGAGGCGACAGCCC
CAAGAAGAAGAGAAAGGTGGAGGCCAGCGGATCCGCTCCGGGAAAAAAGAGGC
CGGTAGAGCACTCTCCTGTGGAGCCAGACTCCTCCTCGGGAACCGGAAAGGCGG
GCCAGCAGCCTGCAAGAAAAAGATTGAATTTTGGTCAGACTGGAGACGCAGACT
CAGTACCTGACCCCCAGCCTCTCGGACAGCCACCAGCAGCCCCCTCTGGTCTGGG
AACTAATACGATGGCTACAGGCAGTGGCGCACCAATGGCAGACAATAACGAGGG
CGCCGACGGAGTGGGTAATTCCTCGGGAAATTGGCATTGCGATTCCACATGGATG
GGCGACAGAGTCATCACCACCAGCACCCGAACCTGGGCCCTGCCCACCTACAAC
AACCACCTCTACAAACAAATTTCCAGCCAATCAGGAGCCTCGAACGACAATCAC
TACTTTGGCTACAGCACCCCTTGGGGGTATTTTGACTTCAACAGATTCCACTGCC
ACTTTTCACCACGTGACTGGCAAAGACTCATCAACAACAACTGGGGATTCCGACC
CAAGAGACTCAACTTCAAGCTCTTTAACATTCAAGTCAAAGAGGTCACGCAGAA
TGACGGTACGACGACGATTGCCAATAACCTTACCAGCACGGTTCAGGTGTTTACT
GACTCGGAGTACCAGCTCCCGTACGTCCTCGGCTCGGCGCATCAAGGATGCCTCC
CGCCGTTCCCAGCAGACGTCTTCATGGTGCCACAGTATGGATACCTCACCCTGAA
CAACGGGAGTCAGGCAGTAGGACGCTCTTCATTTTACTGCCTGGAGTACTTTCCT
TCTCAGATGCTGCGTACCGGAAACAACTTTACCTTCAGCTACACTTTTGAGGACG
TTCCTTTCCACAGCAGCTACGCTCACAGCCAGAGTCTGGACCGTCTCATGAATCC
TCTCATCGACCAGTACCTGTATTACTTGAGCAGAACAAACACTCCAAGTGGAACC
ACCACGCAGTCAAGGCTTCAGTTTTCTCAGGCGGAGCGAGTGACATTCGGGACC
AGTCTAGGAACTGGCTTCCTGGACCCTGTTACCGCCAGCAGCGAGTATCAAAGAC
ATCTGCGGATAACAACAACAGTGAATACTCGTGGACTGGAGCTACCAAGTACCA
CCTCAATGGCAGAGACTCTCTGGTGAATCCGGGCCCGGCCATGGCAAGCCACAA
GGACGATGAAGAAAAGTTTTTTCCTCAGAGCGGGGTTCTCATCTTTGGGAAGCAA
GGCTCAGAGAAAACAAATGTGGACATTGAAAAGGTCATGATTACAGACGAAGAG
GAAATCAGGACAACCAATCCCGTGGCTACGGAGCAGTATGGTTCTGTATCTACCA
ACCTCCAGAGAGGCAACAGACAAGCAGCTACCGCAGATGTCAACACACAAGGCG
TTCTTCCAGGCATGGTCTGGCAGGACAGAGATGTGTACCTTCAGGGGCCCATCTG
GGCAAAGATTCCACACACGGACGGACATTTTCACCCCTCTCCCCTCATGGGTGGA
TTCGGACTTAAACACCCTCCTCCACAGATTCTCATCAAGAACACCCCGGTACCTG
CGAATCCTTCGACCACCTTCAGTGCGGCAAAGTTTGCTTCCTTCATCACACAGTA
CTCCACGGGACAGGTCAGCGTGGAGATCGAGTGGGAGCTGCAGAAGGAAACA
GCAAACGCTGGAATCCCGAAATTCAGTACACTTCCAACTACAACAAGTCTGTTAA
TGTGGACTTTACTGTGGACACTAATGGCGTGTATTCAGAGCTCGCCCCATTGGC
ACCAGATACCTGACTCGTAATCTGTAAGAATTAAACCCGCTGATCAGCCTCGACT
GTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCG

CATTGTCTGAGTAGGTGTCATTCTATTCTGGGGGTGGGGTGGGGCAGGACAGCA
AGGGGGAGGATTGGGAAGACAATAGCAGGCATGCTGGGGATGCGGTGGGCTCTA
TGG

>SEQ ID NO: 12 Intc-Cas9c-GGGGSx3-VP2
GTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCAT
AGTAACGCCAATAGGGACTTTCCATTGACGTCAATGGGTGGACTATTTACGGTAA
ACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATG
GGACTTTCCTACTTGGCAGTACATCTACGTATTAGTCATCGCTATTACCATGGTGA
TGCGGTTTTGGCAGTACATCAATGGGCGTGGATAGCGGTTTGACTCACGGGGATT
TCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTA
GGCGTGTACGGTGGGAGGTCTATATAAGCAGAGCTCTCTGGCTAACTAGAGAAC
CCACTGCTTACTGGCTTATCGAAATTAATACGACTCACTATAGGGAGACCCAAGC
TGGCTAGCGCCACCATGATCAAGATTGCCACGCGCAAGTACCTGGGCAAGCAGA
ACGTGTACGACATCGGAGTGGAGCGCGATCACAACTTTGCCCTGAAGAATGCT
TTATTGCCTCGAACTGTATGCTGGCCTCTGCCGGCGAACTGCAGAAGGGAAACGA
ACTGGCCCTGCCCTCCAAATATGTGAACTTCCTGTACCTGGCCAGCCACTATGAG
AAGCTGAAGGGCTCCCCCGAGGATAATGAGCAGAAACAGCTGTTTGTGGAACAG
CACAAGCACTACCTGGACGAGATCATCGAGCAGATCAGCGAGTTCTCCAAGAGA
GTGATCCTGGCCGACGCTAATCTGGACAAAGTGCTGTCCGCCTACAACAAGCACC
GGGATAAGCCCATCAGAGAGCAGGCCGAGAATATCATCCACCTGTTTACCCTGA
CCAATCTGGGAGCCCCTGCCGCCTTCAAGTACTTTGACACCACCATCGACCGGAA
GAGGTACACCAGCACCAAAGAGGTGCTGGACGCCACCCTGATCCACCAGAGCAT
CACCGGCCTGTACGAGACACGGATCGACCTGTCTCAGCTGGGAGGCGACAGCCC
CAAGAAGAAGAGAAAGGTGGAGGCCAGCGGTGGCGGCGGTTCAGGCGGAGGTG
GCTCTGGGGGCGGGGGTTCTGCTCCGGGAAAAAAGAGGCCGGTAGAGCACTCTC
CTGTGGAGCCAGACTCCTCCTCGGGAACCGGAAAGGCGGGCCAGCAGCCTGCAA
GAAAAAGATTGAATTTTGGTCAGACTGGAGCGCAGACTCAGTACCTGACCCCC
AGCCTCTCGGACAGCCACCAGCAGCCCCCTCTGGTCTGGGAACTAATACGATGGC
TACAGGCAGTGGCGCACCAATGGCAGACAATAACGAGGGCGCCGACGGAGTGG
GTAATTCCTCGGGAAATTGGCATTGCGATTCCACATGGATGGGCGACAGAGTCAT
CACCACCAGCACCCGAACCTGGGCCCTGCCCACCTACAACAACCACCTCTACAA
ACAAATTTCCAGCCAATCAGGAGCCTCGAACGACAATCACTACTTTGGCTACAGC
ACCCCTTGGGGGTATTTTGACTTCAACAGATTCCACTGCCACTTTTCACCACGTGA
CTGGCAAAGACTCATCAACAACAACTGGGGATTCCGACCCAAGAGACTCAACTT
CAAGCTCTTTAACATTCAAGTCAAAGAGGTCACGCAGAATGACGGTACGACGAC
GATTGCCAATAACCTTACCAGCACGGTTCAGGTGTTTACTGACTCGGAGTACCAG
CTCCCGTACGTCCTCGGCTCGGCGCATCAAGGATGCCTCCCGCCGTTCCCAGCAG
ACGTCTTCATGGTGCCACAGTATGGATACCTCACCCTGAACAACGGGAGTCAGGC
AGTAGGACGCTCTTCATTTTACTGCCTGGAGTACTTTCCTTCTCAGATGCTGCGTA
CCGGAAACAACTTTACCTTCAGCTACACTTTTGAGGACGTTCCTTTCCACAGCAG
CTACGCTCACAGCCAGAGTCTGGACCGTCTCATGAATCCTCTCATCGACCAGTAC
CTGTATTACTTGAGCAGAACAAACACTCCAAGTGGAACCACCACGCAGTCAAGG
CTTCAGTTTTCTCAGGCCGGAGCGAGTGACATTCGGGACCAGTCTAGGAACTGGC
TTCCTGGACCCTGTTACCGCCAGCAGCGAGTATCAAAGACATCTGCGGATAACAA
CAACAGTGAATACTCGTGGACTGGAGCTACCAAGTACCACCTCAATGGCAGAGA
CTCTCTGGTGAATCCGGGCCCGGCCATGGCAAGCCACAAGGACGATGAAGAAAA
GTTTTTTCCTCAGAGCGGGGTTCTCATCTTTGGGAAGCAAGGCTCAGAGAAAACA
AATGTGGACATTGAAAAGGTCATGATTACAGACGAAGAGGAAATCAGGACACC
AATCCCGTGGCTACGGAGCAGTATGGTTCTGTATCTACCAACCTCCAGAGAGGCA
ACAGACAAGCAGCTACCGCAGATGTCAACACACAAGGCGTTCTTCCAGGCATGG
TCTGGCAGGACAGAGATGTGTACCTTCAGGGGCCCATCTGGGCAAAGATTCCAC
ACACGGACGGACATTTTCACCCCTCTCCCTCATGGGTGGATTCGGACTTAAACA
CCCTCCTCCACAGATTCTCATCAAGAACACCCCGGTACCTGCGAATCCTTCGACC
ACCTTCAGTGCGGCAAAGTTTGCTTCCTTCATCACACAGTACTCCACGGGACAGG
TCAGCGTGGAGATCGAGTGGGAGCTGCAGAAGGAAAACAGCAAACGCTGGAAT
CCCGAAATTCAGTACACTTCCAACTACAACAAGTCTGTTAATGTGGACTTTACTG
TGGACACTAATGGCGTGTATTCAGAGCCTCGCCCCATTGGCACCAGATACCTGAC
TCGTAATCTGTAAGAATTAAACCCGCTGATCAGCCTCGACTGTGCCTTCTAGTTG
CCAGCCATCTGTTGTTTGCCCCTCCCCCGTGCCTTCCTTGACCCTGGAAGGTGCCA
CTCCCACTGTCCTTTCCTAATAAAATGAGGAAATTGCATCGCATTGTCTGAGTAG
GTGTCATTCTATTCTGGGGGGTGGGGTGGGCAGGACAGCAAGGGGGAGGATTG
GGAAGACAATAGCAGGCATGCTGGGGATGCGGTGGGCTCTATGG >SEQ ID NO: 13 Int$_c$-Cas9$_c$-EAAAKx3-VP2
GTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCAT
AGTAACGCCAATAGGGACTTTCCATTGACGTCAATGGGTGGACTATTTACGGTAA
ACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATG
GGACTTTCCTACTTGGCAGTACATCTACGTATTAGTCATCGCTATTACCATGGTGA
TGCGGTTTTGGCAGTACATCAATGGGCGTGGATAGCGGTTTGACTCACGGGGATT -continued

SEQUENCES

```
TCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTA
GGCGTGTACGGTGGGAGGTCTATATAAGCAGAGCTCTCTGGCTAACTAGAGAAC
CCACTGCTTACTGGCTTATCGAAATTAATACGACTCACTATAGGGAGACCCAAGC
TGGCTAGCGCCACCATGATCAAGATTGCCACGCGCAAGTACCTGGGCAAGCAGA
ACGTGTACGACATCGGAGTGGAGCGCGATCACAACTTTGCCCTGAAGAATGGCT
TTATTGCCTCGAACTGTATGCTGGCCTCTGCCGGCGAACTGCAGAAGGGAAACGA
ACTGGCCCTGCCCTCCAAATATGTGAACTTCCTGTACCTGGCCAGCCACTATGAG
AAGCTGAAGGGCTCCCCCGAGGATAATGAGCAGAAACAGCTGTTTGTGGAACAG
CACAAGCACTACCTGGACGAGATCATCGAGCAGATCAGCGAGTTCTCCAAGAGA
GTGATCCTGGCCGACGCTAATCTGGACAAAGTGCTGTCCGCCTACAACAAGCACC
GGGATAAGCCCATCAGAGAGCAGGCCGAGAATATCATCCACCTGTTTACCCTGA
CCAATCTGGGAGCCCCTGCCGCCTTCAAGTACTTTGACACCACCATCGACCGGAA
GAGGTACACCAGCACCAAAGAGGTGCTGGACGCCACCCTGATCCACCAGAGCAT
CACCGGCCTGTACGAGACACGGATCGACCTGTCTCAGCTGGGAGGCGACAGCCC
CAAGAAGAAGAGAAAGGTGGAGGCCAGCGAGGCAGCAGCCAAAGAGGCCGCTG
CCAAGGAGGCAGCGGCTAAAGCTCCGGGAAAAAAGAGGCCGGTAGAGCACTCT
CCTGTGGAGCCAGACTCCTCCTCGGGAACCGGAAAGGCGGGCCAGCAGCCTGCA
AGAAAAAGATTGAATTTTGGTCAGACTGGAGACGCAGACTCAGTACCTGACCCC
CAGCCTCTCGGACAGCCACCAGCAGCCCCTCTGGTCTGGGAACTAATACGATGG
CTACAGGCAGTGGCGCACCAATGGCAGACAATAACGAGGGCGCCGACGGAGTG
GGTAATTCCTCGGGAAATTGGCATTGCGATTCCACATGGATGGGCGACAGAGTC
ATCACCACCAGCACCCGAACCTGGGCCCTGCCCACCTACAACAACCACCTCTACA
AACAAATTTCCAGCCAATCAGGAGCCTCGAACGACAATCACTACTTTGGCTACAG
CACCCCTTGGGGTATTTTGACTTCAACAGATTCCACTGCCACTTTTCACCACGTG
ACTGGCAAAGACTCATCAACAACAACTGGGGATTCCGACCCAAGAGACTCAACT
TCAAGCTCTTTAACATTCAAGTCAAAGAGGTCACGCAGAATGACGGTACGACGA
CGATTGCCAATAACCTTACCAGCACGGTTCAGGTGTTTACTGACTCGGAGTACCA
GCTCCCGTACGTCCTCGGCTCGGCGCATCAAGGATGCCTCCCGCCGTTCCCAGCA
GACGTCTTCATGGTGCCACAGTATGGATACCTCACCCTGAACAACGGGAGTCAG
GCAGTAGGACGCTCTTCATTTTACTGCCTGGAGTACTTTCCTTCTCAGATGCTGCG
TACCGGAAACAACTTTACCTTCAGCTACACTTTTGAGGACGTTCCTTTCCACAGC
AGCTACGCTCACAGCCAGAGTCTGGACCGTCTCATGAATCCTCTCATCGACCAGT
ACCTGTATTACTTGAGCAGAACAAACACTCCAAGTGGAACCACCACGCAGTCAA
GGCTTCAGTTTTCTCAGGCCGGAGCGAGTGACATTCGGGACCAGTCTAGGAACTG
GCTTCCTGGACCCTGTTACCGCCAGCAGCGAGTATCAAAGACATCTGCGGATAAC
AACAACAGTGAATACTCGTGGACTGGAGCTACCAAGTACCACCTCAATGGCAGA
GACTCTCTGGTGAATCCGGGCCCGGCCATGGCAAGCCACAAGGACGATGAAGAA
AAGTTTTTTCCTCAGAGCGGGGTTCTCATCTTTGGGAAGCAAGGCTCAGAGAAAA
CAAATGTGGACATTGAAAAGGTCATGATTACAGACGAAGAGGAAATCAGGACAA
CCAATCCCGTGGCTACGGAGCAGTATGGTTCTGTATCTACCAACCTCCAGAGAGG
CAACAGACAAGCAGCTACCGCAGATGTCAACACACAAGGCGTTCTTCCAGGCAT
GGTCTGGCAGGACAGAGATGTGTACCTTCAGGGGCCCATCTGGGCAAAGATTCC
ACACACGGACGGACATTTTCACCCCTCTCCCCTCATGGGTGGATTCGGACTTAAA
CACCCTCCTCCACAGATTCTCATCAAGAACACCCCGGTACCTGCGAATCCTTCGA
CCACCTTCAGTGCGGCAAAGTTTGCTTCCTTCATCACACAGTACTCCACGGGACA
GGTCAGCGTGGAGATCGAGTGGGAGCTGCAGAAGGAAAACAGCAAACGCTGGA
ATCCCGAAATTCAGTACACTTCCAACTACAACAAGTCTGTTAATGTGGACTTTAC
TGTGGACACTAATGGCGTGTATTCAGAGCCTCGCCCCATTGGCACCAGATACCTG
ACTCGTAATCTGTAAGAATTAAACCCGCTGATCAGCCTCGACTGTGCCTTCTAGT
TGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGT
AGGTGTCATTCTATTCTGGGGGTGGGTGGGCAGGACAGCAAGGGGGAGGAT
TGGGAAGACAATAGCAGGCATGCTGGGGATGCGGTGGGCTCTATGG
```

This disclosure is not limited in its application to the details of construction and the arrangement of components set forth in this description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. An in vitro method comprising administering to a cell a recombinant adeno-associated virus (rAAV) comprising a capsid protein having a terminally grafted Cas-family nuclease.

2. The method of claim 1, wherein the rAAV further comprises a transgene encoding a guide RNA.

3. The method of claim 1 further comprising administering a second rAAV having a transgene encoding a guide RNA.

4. The method of claim 1, wherein the capsid protein is a VP2 capsid protein.

5. The method of claim 4, wherein the terminally grafted nuclease is grafted to the N-terminus of the VP2 capsid protein, or wherein the terminally grafted nuclease is grafted to the C-terminus of the VP2 capsid protein.

6. The method of claim 4, further comprising a linker conjugated to the C-terminus of the terminally grafted nuclease and the N-terminus of the VP2 protein, or further comprising a linker conjugated to the N-terminus of the terminally grafted nuclease and the C-terminus of the VP2 protein.

7. The method of claim 1, wherein the capsid protein having a terminally grafted nuclease is of:
   (i) an AAV1, AAV2, AAV3, AAV4, AAV5, AAV6, AAV7, AAV8, AAV9, AAV10, AAV11, or AAV12 serotype; or
   (ii) a serotype derived from a non-human primate.

8. The method of claim 1, wherein the Cas-family nuclease is a Cas6, Cas7, Cas9, or dCas9.

9. The method of claim 8, wherein the Cas9 is a *Streptococcus pyogenes* Cas9.

10. The method of claim 1, wherein the cell is a mammalian cell.

11. The method of claim 10, wherein the mammalian cell is a human cell.

* * * * *